(12) United States Patent
Masuda et al.

(10) Patent No.: US 7,736,846 B2
(45) Date of Patent: Jun. 15, 2010

(54) METHODS OF ASSAYING FOR MODULATORS OF THE INFLAMMATORY PROCESS USING COMPONENTS OF THE UBIQUITIN LIGATION CASCADE

(75) Inventors: Esteban Masuda, Menlo Park, CA (US); Brian Wong, San Mateo, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 1724 days.

(21) Appl. No.: 10/652,961

(22) Filed: Aug. 28, 2003

(65) Prior Publication Data

US 2004/0116347 A1 Jun. 17, 2004

Related U.S. Application Data

(60) Provisional application No. 60/407,484, filed on Aug. 30, 2002, provisional application No. 60/437,757, filed on Jan. 3, 2003.

(51) Int. Cl.
*C12Q 1/10* (2006.01)
*G01N 33/53* (2006.01)

(52) U.S. Cl. ............................. 435/4; 435/701; 436/63; 436/544

(58) Field of Classification Search .................. None
See application file for complete search history.

(56) References Cited

U.S. PATENT DOCUMENTS

| | | | |
|---|---|---|---|
| 5,968,761 A | 10/1999 | Rolfe et al. | |
| 5,976,849 A | 11/1999 | Hustad et al. | |
| 6,060,262 A | 5/2000 | Beer-Romero et al. | |
| 6,720,181 B1 | 4/2004 | Chiaur et al. | |
| 6,740,495 B1 * | 5/2004 | Issakani et al. | 435/7.92 |

FOREIGN PATENT DOCUMENTS

| | | | |
|---|---|---|---|
| EP | 1487973 A0 | | 12/2004 |
| WO | WO01/75145 | * | 10/2001 |
| WO | WO 2004/020458 A2 | | 3/2004 |

OTHER PUBLICATIONS

Chen et al., Cell, vol. 84, p. 852-862, 1996.*
Swinney et al., J. Biol. Chem, vol. 277, p. 23573-23581, Jun. 2002.*
Nuber et al., J Bio Chem, vol. 271, p. 2795-2800, 1996.*
Sequence search result.*
Coux et al., "Enzymes Catalyzing Ubiquitination and Proteolytic Processing of the p105 Precursor of Nuclear Factor κB1," *Journal of Biological Chemistry*, 273(15):8820-8828 (1998).
D'Andrea et al., "Relieving the Itch," *Nature Genetics*, 18:97-99 (1998).
Fang et el., "Dysregulation of T lymphocyte function in itchy mice: a role for Itch in $T_H2$ differentiation," *Nature Immunology*, 3(3):281-287 (2002).
Handley et al., "Molecular cloning, sequence, and tissue distribution of the human ubiquitin-activating enzyme E1," *Proc. Natl. Acad. Sci. USA*, 88:258-262 (1991).
Karin et al., Phosphorylation Meets Ubiquitination: The Control of NF-κB Activity, *Annual Review of Immunology*, 18:621-663 (2000).
Kwon et al., "Evidence for Involvement of the Proteasome Complex (26S) and NFκB in IL-1β-Induced Nitric Oxide and Prostaglandin Production by Rat Islets and RINm5F Cells," *Diabetes*, 47:583-591 (1998).
Meiners et al., "Ubiquitin-Proteasome Pathway as a New Target for the Prevention of Restenosis," *Circulation, American Heart Association*, 105(4):483-489 (2002).
Perrt et al., "The itchy locus encodes a novel ubiquitin protein ligase that is disrupted in a$^{18H}$ mice," *Nature Genetics*, 18:143-146 (1998).
Yaron et al., "Identification of the receptor component of the IκBα-ubiquitin ligase," *Nature*, 396:590-594 (1998).
Zacksenhaus et al., "Molecular cloning, primary structure and expression of the human X linked A1S9 gene cDNA which complements the ts A1S9 mouse L cell defect in DNA replication," *The EMBO Journal*, 9(9):2923-2929 (1990).
Zhang et al., "The SOCS box of suppressor of cytokine signaling-1 is important for inhibition of cytokine action in vivo," *PNAS* , 98(23):13261-13265 (2001).

* cited by examiner

*Primary Examiner*—Larry R. Helms
*Assistant Examiner*—Lei Yao
(74) *Attorney, Agent, or Firm*—James J. Diehl, J.D.; Travis Young, J.D.; Klarquist Sparkman, LLP

(57) ABSTRACT

The present invention relates to regulation of inflammation. More particularly, the present invention is directed to nucleic acids encoding components of the ubiquitin ligation pathway, e.g., ubiquitin and ubiquitin-like molecules, E1, E2, and E3 proteins and their substrates, which are involved in modulation of the inflammatory process. The invention further relates to methods for identifying and using agents, including small molecule chemical compositions, antibodies, peptides, cyclic peptides, nucleic acids, RNAi, antisense nucleic acids, and ribozymes, that modulate the inflammatory process via modulation of the ubiquitin ligation pathway; as well as to the use of expression profiles and compositions in diagnosis and therapy related to regulation of inflammation and modulation of cytokine signaling involved in inflammation, e.g., for treatment of infection, autoimmune disease and other diseases related to the inflammatory process.

7 Claims, 8 Drawing Sheets

Figure 1

E1: ubiquitin activating enzyme

| E1 | Alias | ORF | Prot | Modifier | siRNA induced cell cycle arrest | ICAM IFNγ siRNA | ICAM IL-1β siRNA | ICAM TNFα siRNA | Notes |
|---|---|---|---|---|---|---|---|---|---|
| E1 | UBA1, UBE1, A1S9 | NM_003334 | NP_003325 | Ub | G1 and G2/M; apoptosis | INH | INH | INH | |
| MOP-4 | MOP-4 | AB014773 | BAB19785 | FAT10 | G2/M; apoptosis | INH | NE | NE | |
| FLJ14657 | | NM_024818 | NP_079094 | unknown | NE | NE | INH | NE | |
| UBA3 | UBE1C, yeast UBA3 homolog | NM_003968 | NP_003959 | Nedd8 | G2/M; apoptosis | INH | INH | INH | |
| UBA3, 1 mismatch | UBA3 | AF046024 | AAC27648 | Nedd8 | ND | - | - | - | Shorter version |
| UBA2 | UBA2, SAE2 | NM_005499 | NP_005490 | SUMO | NE | INH | NE | NE | UBA2 partner |
| SAE1 | AOS1, HSPC140, SUA1 | NM_005500 | NP_005491 | SUMO | G1; G2/M | NE | NE | NE | |
| SAE1 isoform | AOS1, LOC160202 | XM_090110 | XP_090110 | SUMO | G1 | ENH | NE | NE | UBA2 partner |
| UBE1L | UBE1L, UAE2 | NM_003335 | NP_003326 | ISG-15 | G1; G2/M | NE | NE | NE | |
| hAPG7 | hGSA7, hAPG7 | NM_006395 | NP_006386 | Apg8, Apg12 | NE | ENH | ENH | ENH | |
| hAPG7 isoform | MGC:1334 IMAGE:3504204 | BC000091 | AAH00091 | Apg8, Apg12 | G2/M, apoptosis | NE | ENH | INH | |
| APPBP1 | APPBP1 | NM_003905 | NP_003896 | Nedd8 | NE | NE | INH | NE | UBA3 partner |
| MOCS3, molybdopterin synthase sulfurylase | MGC:9252 IMAGE:3908290 | NM_014484 | NP_055299 | | NE | NE | NE | | |
| MOCS3 short | | | | | G2/M | INH | NE | NE | 39aa exon deletion |

Figure 2
E2: ubiquitin conjugating enzyme

| E2 | Alias | ORF | Prot | Previously identified function (Mammals Only) | Modifier | siRNA induced cell cycle arrest | HeLa DN GFP/Cell Tracker | A549 DN GFP/CT | ICAM TNFα siRNA | ICAM IFNγ siRNA | ICAM IL-1β siRNA |
|---|---|---|---|---|---|---|---|---|---|---|---|
| UBE2D1 Hs | UBE2D1, UBCH5A, UBC4/5 homolog | NM_003338.1 | NP_003329.1 | Mediates E6-AP ubiquitylation of p53 | Ub | | NE | | NE | NE | NE |
| FTS homolog Hs +1aa | fused toes homolog, FLJ13258 | NM_022476.1 | NP_071921.1 | Apoptosis, Limb and Thymic Development | unknown | G2/M, apoptosis; S | NE | | NE | NE | NE |
| MGC:10481 Hs | MGC:10481, IMAGE:3838157 | BC004862.1 | AAH04862.1 | unknown | unknown | G2/M | NE | | NE | NE | INH |
| XM_054332 .1 Hs | | XM_054332.1 | XP_054332.1 | unknown | unknown | G2/M | NE | | NE | NE | NE |
| E2-230K homolog Hs | E2-230K ortholog, FLJ12878, KIAA1734 | NM_022066.1 | NP_071349.1 | unknown | unknown | NE | | | NE | NE | NE |
| UBC8 Hs | UBE2H, UBCH, UBCH2, UBC8 homolog | NM_003344.1 | NP_003335.1 | unknown | Ub | G2/M | NE | | ENH | ENH | ENH |
| UBE2E1 Hs | UBE2E1, UBCH6, UBC4/5 homolog | NM_003341.1 | NP_003332.1 | unknown | Ub | NE | | | INH | INH | INH |
| RAD6/UBE2 A Hs | UBE2A, RAD6A, HHR6A, UBC2, RAD6 homolog | NM_003336.1 | NP_003327.1 | spermatogenesis (-/-), DNA Repair | Ub | NE | NE | | NE | NE | NE |

Fig 2 cont'd

| E2 | Alias | ORF | Prot | Previously identified function (Mammals Only) | Modifier | siRNA induced cell cycle arrest | HeLa DN GFP/Cell Tracker | A549 DN GFP/CT | ICAM TNFα siRNA | ICAM IFNγ siRNA | ICAM IL-1β siRNA |
|---|---|---|---|---|---|---|---|---|---|---|---|
| UBE2E3 Hs | UBE2E3, UBCH9, UBC4/5 homolog | NM_006357.1 | NP_006348.1 | unknown | Ub | G2/M | NE | | ENH | NE | NE |
| UBC12/UBE 2M Hs | UBE2M, HUBC12, UBC12 homolog | NM_003969.1 | NP_003960.1 | Regulation of SCF complex/cell cycle/NF-kB | NEDD8 | G2/M | NE | | NE | NE | NE |
| Huntingtin interact prot 2 (HIP2) Hs | HIP2, LIG, E2-25K | NM_005339.2 | NP_005330.1 | unknown | Ub | | | | NE | INH | NE |
| UBC6 Hs | UBC6 | AF296658.1 | AAK52609.1 | ERAD | Ub | G2/M | 374%/1.4 | 38%/1.3 | NE | ENH | NE |
| HBUCE1/U BE2D2 var Hs | HBUCE1, LOC51619 | NM_015983.1 | NP_057067.1 | unknown | unknown | | | | NE | NE | NE |
| NEDD8-conj enzyme 2 (NCE2) Hs | NCE2 | NM_080678.1 | NP_542409.1 | unknown | NEDD8 | | | | | | |
| UBC13/UBE 2N Hs | UBE2N, UBCH-BEN, UBC13 hom., sim to bendless | NM_003348.1 | NP_003339.1 | IKK/NF-kB activation | unknown | NE | | | NE | NE | INH |

Figure 3
E3: ubiquitin ligase

| E3 | Orf | Prot | siRNA induced cell cycle arrest | ICAM-TNFα | ICAM-IFNγ | ICAM-IL1β |
|---|---|---|---|---|---|---|
| APC11 | NM_016476 | NP_057560 | G2 | NE | NE | ENH |
| APC2 | NM_013366 | NP_037498 | G2 | NE | ENH | NE |
| Topo IIa | | | | NE | NE | NE |
| Roc1 | NM_014248 | NP_055063 | S, G2 | ENH | ENH | ENH |
| TRAF6 | NM_145803 | NP_665802 | | NE | NE | INH |

Figure 4
Ubiquitin-like molecule

| Ubl | Alias | ORF | Prot |
|---|---|---|---|
| Ubiquitin | | NM_002954.2 | NP_002945 |
| NEDD-8 | | NM_006156.1 | NP_006147 |
| ISG-15 | UCRP | NM_005101.1 | NP_005092.1 |
| APG12 | APG12L,MAP1_LC3 | NM_004707.1 | NP_004698.1 |
| APG8 | MAP1_LC3, MAP1A, 1BLC3 | NM_022818.2 | NP_073729.1 |
| Fat10 | Diubiquitin | NM_006398.1 | NP_006389.1 |
| Fau, Fubi | FBR-MuSV-associated ubiquitously expressed gene,ubiquitin-like protein fubi,40S ribosomal protein S30,FAU-encoded ubiquitin-like protein | NM_001997.2 | NP_001988.1 |
| SUMO-1 | Sentrin1,SMT3C,GMP1,PIC,SM,SMT3H3 | NM_003352.2 | NP_003343.1 |
| SUMO-2 | Sentrin3,SMT3A,SMT3H1 | NM_006936.1 | NP_008867.1 |
| SUMO-3 | SMT3B,SMT3H2,HSMT3 | NM_006937.2 | NP_008868.2 |

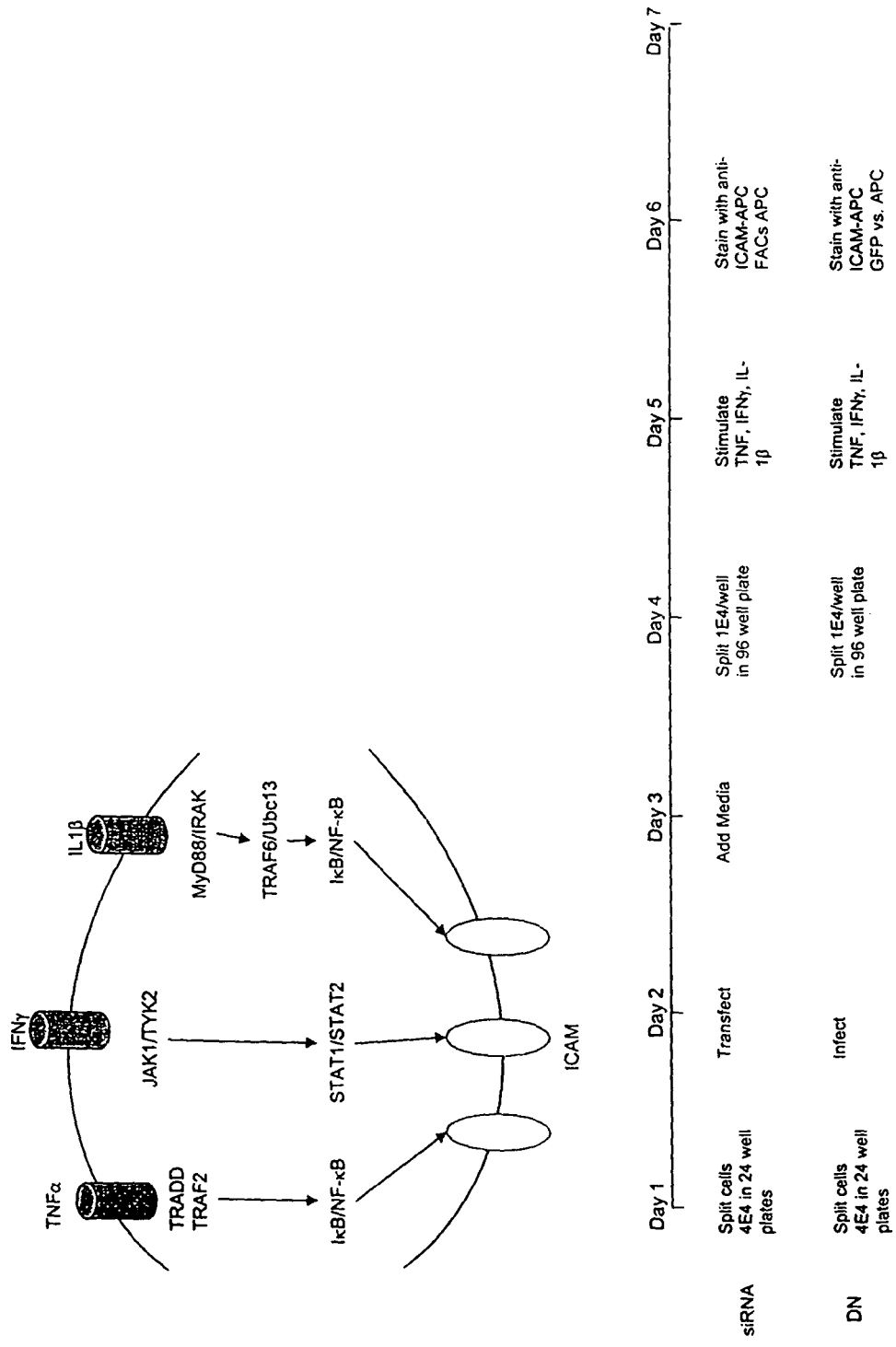

Figure 6

GEOMETRIC MEAN APC-ICAM

| Common | ø | TNFα | IFNγ | IL-1β |
|---|---|---|---|---|
| Ubc8 | 40.4 | 3162 | 1368 | 2350 |
| UbcH6 | 8.35 | 733 | 550 | 588 |
| UbcH9 | 11.4 | 2296 | 718 | 1619 |
| HIP2 | * | * | 511 | 1347 |
| Ubc13 | 12 | 1170 | 1166 | 589 |
| Roc1 | 58.4 | 3028 | 1475 | 1783 |
| TRAF6 | 11.6 | 1417 | 1215 | 686 |
| APC11 | 28.6 | 2011 | 1516 | 1975 |
| APC2 | 98.8 | 1779 | 1872 | 1549 |
| FLJ14657 MoeB E1 | 12.4 | 1364 | 1005 | 734 |
| Uba3 | 23.3 | 795 | 742 | 705 |
| Random | 10.8 | 1589 | 932 | 1247 |
| Mock | 11.9 | 1669 | 960 | 1228 | siRNA PLATE1  Enhanced activity
Strongly inhibited activity
Inhibited activity

*=Data not obtained

Figure 7

GEOMETRIC MEAN APC-ICAM

| Ligase Protein | ø | TNFα | IFNγ | IL-1β |
|---|---|---|---|---|
| MGC10581 | 13.8 | 1035 | 679 | 664 |
| Ubc8 | 41 | 2849 | 1287 | 2181 |
| UbcH6 | 8.63 | 620 | 569 | 648 |
| RAD6A | 11.9 | 1499 | 698 | 620 |
| UbcH9 | 13.3 | 2164 | 757 | 1379 |
| HIP2 | 4.72 | 1592 | 546 | 1308 |
| Ubc6 | 20.3 | 1464 | 1175 | 963 |
| Ubc13 | * | 1201 | 968 | 623 |
| Roc1 | 47.5 | 2759 | 1402 | 1733 |
| TRAF6 | 11.6 | 1325 | 1081 | 627 |
| APC11 | 28.1 | 2020 | 1042 | 1951 |
| APC2 | 95 | 1932 | 1957 | 1651 |
| FLJ14657 MoeB E1 | 10.4 | 1395 | 866 | 680 |
| Uba3 | 19.5 | 769 | 709 | 677 |
| Random | 16.7 | 1543 | 867 | 1192 |
| Mock | 10.6 | 1577 | 861 | 1256 | siRNA PLATE2

Enhanced activity
Strongly inhibited activity
Inhibited acvitity

*=Data not obtained

METHODS OF ASSAYING FOR MODULATORS OF THE INFLAMMATORY PROCESS USING COMPONENTS OF THE UBIQUITIN LIGATION CASCADE

CROSS-REFERENCES TO RELATED APPLICATIONS

The present application claims the benefit of U.S. Ser. No. 60/407,484, filed Aug. 30, 2002, and U.S. Ser. No. 60/437,757, filed Jan. 3, 2003, each herein incorporated by reference in their entirety.

STATEMENT AS TO RIGHTS TO INVENTIONS MADE UNDER FEDERALLY SPONSORED RESEARCH AND DEVELOPMENT

Not applicable.

FIELD OF THE INVENTION

The present invention relates to regulation of inflammation. More particularly, the present invention is directed to nucleic acids encoding components of the ubiquitin ligation pathway, e.g., ubiquitin and ubiquitin-like molecules, E1, E2, and E3 proteins and their substrates, which are involved in modulation of the inflammatory process. The invention further relates to methods for identifying and using agents, including small molecule chemical compositions, antibodies, peptides, cyclic peptides, nucleic acids, RNAi, antisense nucleic acids, and ribozymes, that modulate the inflammatory process via modulation of the ubiquitin ligation pathway; as well as to the use of expression profiles and compositions in diagnosis and therapy related to regulation of inflammation and modulation of cytokine signaling involved in inflammation, e.g., for treatment of infection, autoimmune disease and other diseases related to the inflammatory process.

BACKGROUND OF THE INVENTION

Inflammation is a host defense system that is closely related to the immune response to foreign matter, e.g. infection, and is also a cause of disease and death, e.g., autoimmune disease. The four basic symptoms of inflammation are redness, swelling, heat and pain, which represent the consequence of capillary dilation with edema and the migration of phagocytes to the affected area. Acute inflammation is characterized by neutrophil infiltration. Inflammation can become chronic, and is characterized by infiltration by mononuclear phagocytes and lymphocytes. As inflammation is widely involved as a cause of disease as well as a defense mechanism against disease, there is a need to establish screening for understanding human diseases caused by modulation of the inflammatory process. Identifying proteins, their ligands and substrates, and downstream signal transduction pathways involved in the inflammatory process in humans is important for developing therapeutic regents to treat infection, and to treat other diseases of the inflammatory process, such as autoimmune disease.

BRIEF SUMMARY OF THE INVENTION

The present invention therefore provides nucleic acids encoding protein components of the ubiquitin ligation cascade such as ubiquitin and ubiquitin-like molecules, E1, E2, and E3, and their substrates, which are involved in inflammation modulation, e.g., by modulating cellular response to cytokine signaling (e.g., TNF-α, IL-1β, and INF-γ). The invention provides methods of screening for compounds, e.g., small organic molecules, antibodies, peptides, cyclic peptides, nucleic acids, antisense molecules, RNAi, and ribozymes, that are capable of modulating the inflammatory process, e.g., inhibiting cellular proliferation, or activating apoptosis, or activating ICAM signaling, or modulating cellular response to cytokine signaling. Therapeutic and diagnostic methods and reagents are also provided. Modulators of the ubiquitin ligase cascade are therefore useful in treatment of infection and autoimmune disease.

In one aspect, the present invention provides method for identifying a compound that modulates and the inflammatory process, the method comprising the steps of: (i) contacting a cell comprising a polypeptide from FIG. 1, column 1, FIG. 2, column 1, or FIG. 3, column 1, or a fragment thereof, with the compound, the polypeptide encoded by a nucleic acid that hybridizes under stringent conditions to a nucleic acid encoding a polypeptide having an amino acid sequence as identified in FIG. 1, column 4, FIG. 2, column 4, or FIG. 3, column 3; and (ii) determining the effect of the compound upon the cell comprising the polypeptide or fragment thereof, thereby identifying a compound that modulates the inflammatory process.

In one embodiment, modulation of the inflammatory process is associated with lymphocyte activation. In another embodiment, modulation of the inflammatory process is associated with phagocyte activation. In another embodiment, modulation of the inflammatory process causes cellular proliferation. In another embodiment, modulation of the inflammatory process causes apoptosis. In another embodiment, modulation of the inflammatory process causes cell cycle arrest.

In one embodiment, the effect of the compound on the cell is determined by measuring cell cycle arrest, cellular proliferation, or apoptosis. In another embodiment, the effect of the compound on the cell is determined by measuring ICAM activation via stimulation with IL-1β, TNF-α, or INF-γ, followed by FACS analysis. In another embodiment, modulation is activation of ICAM expression.

In one embodiment, the host cell is a lymphocyte or a phagocyte. In another embodiment, the host cell is a cancer cell. In another embodiment, the cancer cell is a transformed cell line. In another embodiment, the transformed cell line is A549, HUVEC, or HBEC.

In one embodiment, the polypeptide is recombinant. In another embodiment, the polypeptide is encoded by a nucleic acid comprising a sequence selected from FIG. 1, column 3, FIG. 2, column 3, or FIG. 3, column 3.

In one embodiment, the compound is an RNAi molecule, a small organic molecule, an antibody, an antisense molecule, or a peptide, e.g., a circular peptide.

In another aspect, the present invention provides a method for identifying a compound that modulates the inflammatory process, the method comprising the steps of: i) contacting a polypeptide from FIG. 1, column 1, FIG. 2, column 1, or FIG. 3, column 1, or a fragment thereof, with the compound, the polypeptide encoded by a nucleic acid that hybridizes under stringent conditions to a nucleic acid encoding a polypeptide having an amino acid sequence as identified in FIG. 1, column 4, FIG. 2, column 4, or FIG. 3, column 3; (ii) determining the effect of the compound upon the polypeptide or fragment thereof; and (iii) contacting a cell comprising the polypeptide with the compound; and (iv) determining the effect of the compound upon a cell comprising the polypeptide or fragment thereof, thereby identifying a compound that modulates the inflammatory process.

In another aspect, the present invention provides a method for identifying a compound that modulates the inflammatory process, the method comprising the steps of: (i) contacting a polypeptide from FIG. 1, column 1, FIG. 2, column 1, or FIG. 3, column 1, or a fragment thereof, with the compound, the polypeptide encoded by a nucleic acid that hybridizes under stringent conditions to a nucleic acid encoding a polypeptide having an amino acid sequence as identified in FIG. 1, column 4, FIG. 2, column 4, or FIG. 3, column 3; and (ii) determining the effect of the compound upon the polypeptide or fragment thereof in vitro using a ubiquitin ligase assay, thereby identifying a compound that modulates the inflammatory process.

In another aspect, the present invention provides a method of identifying an inflammation modulating compound, comprising: (i) combining (a) a ubiquitin activating agent (E1) selected from the E1s listed in FIG. 1, column 1, (b) a ubiquitin moiety which binds with said E1 in the process of ubiquitin activation and (c) a compound, under conditions in which said E1 normally forms a bond with said ubiquitin moiety and (ii) determining the binding of said E1 and said ubiquitin moiety, wherein an alteration in binding between said E1 and said ubiquitin moiety as compared with binding in the absence of said compound indicates that said compound modulates the inflammatory process.

In another aspect, the present invention provides a method of identifying an inflammation modulating compound, comprising: (i) combining (a) a ubiquitin conjugating agent (E2) selected from the E2s listed in FIG. 2, column 1, (b) a ubiquitin activating agent (E1) capable of transferring an activated ubiquitin moiety to said E2, (c) a ubiquitin moiety capable of being activated by said E1 and subsequently binding said E2 and (d) a compound, under conditions in which said E1 normally transfers an activated ubiquitin moiety to said E2 and (ii) determining the binding of said E2 and said ubiquitin moiety, wherein an alteration in binding between said E2 and said ubiquitin moiety as compared with binding in the absence of said compound indicates that said compound modulates the inflammatory process.

In another aspect, the present invention provides a method of identifying an inflammation modulating compound, comprising: (i) combining (a) a ubiquitin ligating agent (E3) selected from the E3s listed in FIG. 3, column 1, (b) a ubiquitin conjugating agent (E2) capable of transferring an activated ubiquitin moiety to said E3, (c) a ubiquitin activating agent (E1) capable of transferring an activated ubiquitin moiety to said E2, (d) a ubiquitin moiety capable of being activated by said E1 and subsequently transferred, via said E2, and binding said E3 and (e) a compound, under conditions in which said E2 normally transfers an activated ubiquitin moiety to said E3 and (ii) determining the binding of said E3 and said ubiquitin moiety, wherein an alteration in binding between said E3 and said ubiquitin moiety as compared with binding in the absence of said compound indicates that said compound modulates the inflammatory process.

In another aspect, the present invention provides a method for identifying a compound that modulates the inflammatory process, the method comprising the steps of: (i) contacting a cell comprising a polypeptide from FIG. 1, column 1, FIG. 2, column 1, or FIG. 3, column 1, or a fragment thereof, with the compound, the polypeptide encoded by a nucleic acid that hybridizes under stringent conditions to a nucleic acid encoding a polypeptide having an amino acid sequence as identified in FIG. 1, column 4, FIG. 2, column 4, or FIG. 3, column 3; and (ii) determining the effect of the compound upon the cell comprising the polypeptide or fragment thereof using an ICAM induction assay and FACS analysis, thereby identifying a compound that modulates the inflammatory process.

In another aspect, the present invention provides a method of modulating an inflammatory cell comprising, (i) providing a cell comprising a polypeptide, or naturally occurring variant thereof, selected from: a peptide of FIG. 1, column 1, a peptide of FIG. 2, column 2; and a peptide of FIG. 3, column 3; and (ii) contacting said cell with an inhibitor of said polypeptide, whereby said inflammatory cell is modulated.

In one embodiment, the E1 is FLJ14657, the E2 is IMAGE: 3838157, UbcH6, or HIP2, and the ubiquitin moiety is Nedd8.

In another aspect, the present invention provides a method of modulating the inflammatory process in a subject, the method comprising the step of administering to the subject a therapeutically effective amount of a compound identified using the methods described herein.

In one embodiment, modulation of the inflammatory process is associated with lymphocyte activation. In another embodiment, the modulation of the inflammatory process is associated with phagocyte activation. In another embodiment, the subject is a human. In another embodiment, the subject has an infection. In another embodiment, the subject has an autoimmune disease.

In another embodiment, the compound inhibits phagocyte proliferation or lymphocyte proliferation. In another embodiment, the compound activates phagocyte proliferation or lymphocyte proliferation.

In one aspect, the present invention provides a method of modulating the inflammatory process in a subject, the method comprising the step of administering to the subject a therapeutically effective amount of a polypeptide from FIG. 1, column 1, FIG. 2, column 1, or FIG. 3, column 1, the polypeptide encoded by a nucleic acid that hybridizes under stringent conditions to a nucleic acid encoding a polypeptide having an amino acid sequence as identified in FIG. 1, column 4, FIG. 2, column 4, or FIG. 3, column 3.

In another aspect, the present invention provides method of modulating the inflammatory process in a subject, the method comprising the step of administering to the subject a therapeutically effective amount of a nucleic acid encoding a polypeptide from FIG. 1, column 1, FIG. 2, column 1, or FIG. 3, column 1, the polypeptide encoded by a nucleic acid that hybridizes under stringent conditions to a nucleic acid encoding a polypeptide having an amino acid sequence as identified in FIG. 1, column 4, FIG. 2, column 4, or FIG. 3, column 3.

In another aspect, the present invention provides a method for identifying a compound capable of interfering with binding of a component of the ubiquitin ligation pathway or fragment thereof, the method comprising the steps of: (i) combining a first polypeptide of FIG. 1, column 1, with a second polypeptide of FIG. 2, column 1, or fragment thereof; and (ii) determining the binding of the first polypeptide or fragment thereof to the second polypeptide.

In one embodiment, the first polypeptide or fragment thereof and the second polypeptide are combined first. In another embodiment, the first polypeptide or fragment thereof and the second polypeptide are expressed in a cell. In another embodiment, the cell is a yeast cell or a mammalian cell. In another embodiment, the first polypeptide or fragment thereof is fused to a heterologous polypeptide. In another embodiment, the binding of the first polypeptide or fragment thereof to the second polypeptide is determined by measuring reporter gene expression.

In another aspect, the present invention provides a method for identifying a compound capable of interfering with binding of a component of the ubiquitin ligation pathway or fragment thereof, the method comprising the steps of: (i) combining a first polypeptide of FIG. 1, column 1, with a second polypeptide of FIG. 4, column 1, or fragment thereof; and (ii) determining the binding of the first polypeptide or fragment thereof to the second polypeptide.

In one aspect, the present invention provides methods of ubiquitinating a substrate in vitro or in vivo by providing a ubiquitin ligation cascade molecule. In another aspect, the present invention provides methods of modulating a protein by ubiquitination, e.g., by overexpression of a ubiquitin ligation cascade molecule or by modulation of a ubiquitin ligation cascade molecule.

In one aspect, the present invention provides a method of modulating inflammation, the method comprising the step of administering to a cell a vector expressing an siRNA molecule, wherein the siRNA molecule is from 21 to 30 nucleotide base pairs in length and wherein the siRNA molecule is specific for a nucleic acid encoding a polypeptide having an amino acid sequence as identified in FIG. 1, column 4, FIG. 2, column 4, or FIG. 3, column 3.

BRIEF DESCRIPTION OF THE DRAWINGS

FIG. 1 provides a list of E1 ubiquitin activating enzyme genes and the proteins encoded by the genes that are involved in modulation of the inflammatory process. NE: no effect. INH: inhibition. ENH: enhanced. DN: dominant negative cDNA.

FIG. 2 provides a list of E2 ubiquitin conjugating enzyme genes and the proteins encoded by the genes that are involved in modulation of the inflammatory process. NE: no effect. INH: inhibition. ENH: enhanced. DN: dominant negative cDNA.

FIG. 3 provides a list of E3 ubiquitin ligase genes and the proteins encoded by the genes that are involved in modulation of the inflammatory process. NE: no effect. INH: inhibition. ENH: enhanced. DN: dominant negative cDNA.

FIG. 4 provides a list of ubiquitin moieties, including ubiquitin-like molecules (ubl), ubiquitin, and fragments thereof.

FIG. 5 provides an diagram of an inflammation assay that detects ICAM induction in A549 cells.

FIG. 6 provides the results of ICAM inflammation assays using siRNA to inhibit selected members of the ubiquitin ligation cascade.

FIG. 7 provides the results of ICAM inflammation assays using siRNA to inhibit selected members of the ubiquitin ligation cascade.

DETAILED DESCRIPTION OF THE INVENTION

Introduction

The ubiquitin ligase cascade functions to regulate protein turnover in a cell by closely regulating the degradation of specific proteins. By regulating protein degradation, cells can quickly eliminate a protein that in turn regulates another function (e.g., a transcription factor that is needed to express a particular gene). Furthermore, this form of control is very effective, as the elimination of a particular protein ensures that the process governed by the protein is shut-down. In this process, ubiquitin or a ubiquitin-like protein (see FIG. 4) is covalently ligated to a target or substrate protein, resulting in a poly-ubiquitinated target protein that is rapidly detected a degraded by the 26S proteasome. E1 enzymes of the ubiquitin ligation cascade are known as "ubiquitin-activating enzymes." These enzymes activate ubiquitin in an ATP-dependent manner so that the ubiquitin is in a reactive state. E2 enzymes are known as "ubiquitin conjugating enzymes." These enzymes are involved in catalyzing the attachment of ubiquitin to the substrate protein. E3 enzymes are known as "ubiquitin ligases." E3s function in concert with E2 enzymes, sometimes in preferred pairs, and link the ubiquitin to the substrate molecule to form polyubiquitinated substrates. E3s are thought to play a role in recognizing the substrate protein. E3 molecules can have a single subunit responsible for the ligase activity, or can act as a multi-subunit complex. For a review of the ubiquitin ligation cascade and its components, see Weissman, *Nature Reviews* 2:169-178 (2001); Hans & Siepmann, *FASEB J.* 11:1257-1268 (1997). Identification of ubiquitin, ubiquitin-like molecules, E1, E2, and E3 enzymes is well known to those of skill in the art.

As described below, the present inventors for the first time have identified E1, E2, and E3 members of the ubiquitin ligase cascade as regulators of the inflammatory process (see FIGS. 1, 2, and 3). These proteins were identified by functional knock-out studies, using, e.g., cDNA, peptide, and siRNA molecules. cDNA, peptide and siRNA molecules act, e.g., transdominant effectors (activator or inhibitor molecules such as peptides, siRNA, antisense molecules, ribozymes, antibodies, small organic molecules, etc.), or dominant negative mutants (e.g., cDNA encoding a dominant negative protein), and can be used in functional assays for inflammation phenotype to validate members of the ubiquitin ligation cascade such as E1, E2, and E3 proteins as inflammatory process modulators. It should be noted that some but not all effector molecules can produce an effect for any specific target. Therefore, a finding of "no effect" for a particular effector, such as a specific siRNA or cDNA, is not necessarily an indicator that a particular target is not responsible for a given phenotype. These proteins were also identified using yeast-two hybrid studies with baits having known disease associations.

The identified components of the ubiquitin ligation cascade therefore represent a drug target for compounds that suppress or activate the inflammatory process, e.g., by modulating cellular response to cytokine signaling, activating ICAM expression, causing cell cycle arrest, causing release from cell cycle arrest, inhibiting or activating cellular proliferation, and activating or inhibiting apoptosis. Agents identified in these assays, including small organic molecules, peptides, cyclic peptides, nucleic acids, antibodies, antisense nucleic acids, RNAi, and ribozymes, that modulate inflammation, can be used to treat diseases related to the inflammatory process. In particular, inflammation modulators are useful for treatment of infections, e.g., viral, bacterial, parasitic, and fungal infections, as well as diseases of chronic inflammation such as autoimmune disease.

Definitions

"Ubiquitin ligation pathway or component" refers to ubiquitin and ubiquitin-like molecules (see FIG. 4), and E1, E2, and E3 proteins and their substrates, which are involved in the ubiquitination process (see, e.g., Weissman, *Nature Reviews* 2:169-178 (2001); see also WO 01/75145)).

"Phagocyte" or "phagocytic leukocyte" refers to both polymorphonuclear leukocytes or granulocytes (e.g., neutrophils, eosinophils, and basophils) and mononuclear phagocytes (e.g., macrophages and monocytes) (see, e.g., Paul, *Immunology*, chapter 27, page 941-942 (3rd ed., 1993)). Phagocytosis, the engulfment and elimination of foreign cell and foreign particulate materials, is a characteristic of antigen elimination in inflammation, carried out by phagocytes.

"Inflammation" or the "inflammatory process" refers to inflammation as characterized by four basic symptoms: redness, swelling, heat, and pain. Inflammation can be acute or chronic, with chronic inflammation characterized further by infiltration of T lymphocytes and mononuclear phagocytes, while acute inflammation is characterized by neutrophil infiltration and edema (see, e.g., Paul, *Immunology*, chapters 27 and 29 (3rd ed., 1993)). In the inflammatory process, presentation to or recognition of foreign antigen by B and T cells leads to activation an amplification system, including the complement cascade, lipid mediator, coagulation cascade, antibody production, cytokine release, recruitment of phagocytes, etc. Cytokine signaling, e.g., by Il-1β, TNF-α, and IFN-γ, is an important component of the inflammatory process for recruitment of phagocytes and T lymphocytes. Cytokines are produced by immune cells such as T cells (IFN-γ) and macrophages (Il-1β, TNF-α). Immediate and delayed type hypersensitivity are acute and chronic inflammation, respectively, that occur in the skin.

By "disorder associated with inflammation or the inflammatory process" or "disease associated with cytokine signaling" herein is meant a disease state which is marked by either an excess or a deficit of inflammation, or improper modulation of inflammation, e.g., improper modulation of cellular proliferation or apoptosis in cells of the inflammatory process. Such disorders associated with the inflammatory process include, but are not limited to, infections (e.g., viral, bacterial, fungal, and parasitic), allergic reactions (e.g., asthma), autoimmune disease (e.g., rheumatoid arthritis, systemic lupus erythematosis, osteoarthritis, and spondyloarthropathies), GVHD, cardiac disease (e.g., ischemia, myocarditis, atherosclerosis, reperfusion injury, hypertrophy, and heart failure), cancer (e.g. hematologic malignancies such as MM, MDS, and AML, and renal cell carcinoma), COPD, etc. (see, e.g., *Harrison's Principles of Internal Medicine* (14th ed., 1998), Paul, *Immunology* (3rd ed. 1993), Sack, *Pharmacol. Ther.* 94:123 (2002); Sharma & Anker, *Int. J. Cardiol.* 85:161 (2002); Tsimberidou & Giles, *Expert. Rev. Anticancer* 2:277-286 (2002); Lorenz & Kalden, *Arthritis Res.* 4 Suppl 3:S17-24 (2002); Khan, *Ann. Intern. Med.* 136:896-907 (2002); De Boer, *Chest* 121 (5 Suppl):209S-218S (2002); Glaspy, *Semin. Oncol.* 29 (3 Suppl):41-46 (2002); Hubel et al., *J. Infect. Dis.* 185:1490-1501 (2002); Ikeda et al., *Cytokine Growth Factor Rev.* 13:95-109 (2002); and Egermayer et al., *Expert Opin. Pharmacother.* 2:1093-1097 (2001)).

The terms "ubiquitin ligation cascade component" or a nucleic acid encoding "a ubiquitin ligation cascade component" refer to nucleic acids and polypeptide polymorphic variants, alleles, mutants, and interspecies homologs that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of over a region of at least about 25, 50, 100, 200, 500, 1000, or more amino acids, to an amino acid sequence encoded by an nucleic acid that encodes a protein as shown in column 1 of FIGS. 1, 2, or 3; (2) bind to antibodies, e.g., polyclonal antibodies, raised against an immunogen comprising an amino acid sequence of a protein as shown in column 1 of FIGS. 1, 2, and 3, and conservatively modified variants thereof; (3) specifically hybridize under stringent hybridization conditions to an anti-sense strand corresponding to a nucleic acid sequence encoding an protein of column 1, FIGS. 1, 2, and 3, and conservatively modified variants thereof; (4) have a nucleic acid sequence that has greater than about 95%, preferably greater than about 96%, 97%, 98%, 99%, or higher nucleotide sequence identity, preferably over a region of at least about 25, 50, 100, 200, 500, 1000, or more nucleotides, to a nucleic acid encoding a protein of column 1, FIGS. 1, 2, and 3. A polynucleotide or polypeptide sequence is typically from a mammal including, but not limited to, primate, e.g., human; rodent, e.g., rat, mouse, hamster; cow, pig, horse, sheep, or any mammal. The nucleic acids and proteins of the invention include both naturally occurring or recombinant molecules. A protein of the invention typically has activity in a ubiquitin ligase assay (see, e.g., WO 01/17145).

The phrase "functional effects" in the context of assays for testing compounds that modulate activity of a ubiquitin ligation cascade protein includes the determination of a parameter that is indirectly or directly under the influence of a ubiquitin ligation cascade protein, e.g., a phenotypic or chemical effect, such as the ability to increase or decrease the inflammatory response, response to cytokine signaling, e.g., ICAM activation, cellular proliferation, apoptosis, cell cycle arrest, chemotaxis, phagocytosis, or e.g., a physical effect such as ligand or substrate binding or inhibition of ligand or substrate binding. "Functional effects" include in vitro, in vivo, and ex vivo activities.

By "determining the functional effect" is meant assaying for a compound that increases or decreases a parameter that is indirectly or directly under the influence of a ubiquitin ligation cascade protein, e.g., measuring physical and chemical or phenotypic effects. Such functional effects can be measured by any means known to those skilled in the art, e.g., changes in spectroscopic characteristics (e.g., fluorescence, absorbance, refractive index); hydrodynamic (e.g., shape); chromatographic; or solubility properties for the protein; measuring inducible markers or transcriptional activation of the protein; measuring binding activity or binding assays, e.g. binding to antibodies; measuring changes in ligand or substrate binding activity; measuring ICAM activation; measuring cellular proliferation; measuring apoptosis; measuring cell surface marker expression; measurement of changes in protein levels for ubiquitin ligation cascade-associated sequences; measurement of RNA stability; phosphorylation or dephosphorylation; ligase activity; identification of downstream or reporter gene expression (CAT, luciferase, β-gal, GFP and the like), e.g., via chemiluminescence, fluorescence, colorimetric reactions, antibody binding, and inducible markers. In one embodiment, the function effect is determined using an in vitro ubiquitin ligase assay or a ubiquitin conjugation assay as described in Examples 2 and 3 of WO 01/17145, using recombinant ubiquitin and ubiquitin-like molecules, E1, E2, and E3 molecules of choice, e.g., those listed in FIGS. 1-4. In another embodiment, the functional effect is determined by assaying ICAM activation followed by FACS analysis.

"Inhibitors", "activators", and "modulators" of ubiquitin ligation cascade polynucleotide and polypeptide sequences are used to refer to activating, inhibitory, or modulating molecules identified using in vitro and in vivo assays of ubiquitin ligation cascade polynucleotide and polypeptide sequences. Inhibitors are compounds that, e.g., bind to, partially or totally block activity, decrease, prevent, delay activation, inactivate, desensitize, or down regulate the activity or expression of ubiquitin ligation cascade proteins, e.g., antagonists. "Activators" are compounds that increase, open, activate, facilitate, enhance activation, sensitize, agonize, or up regulate ubiquitin ligation cascade protein activity, e.g., agonists. Inhibitors, activators, or modulators also include genetically modified versions of ubiquitin ligation cascade proteins, e.g., versions with altered activity, as well as naturally occurring and synthetic ligands, substrates, antagonists, agonists, antibodies, peptides, cyclic peptides, nucleic acids, antisense molecules, ribozymes, small chemical molecules and the like. Such assays for inhibitors and activators include, e.g., expressing ubiquitin ligation cascade protein in vitro, in cells, or cell membranes, applying putative modulator compounds, and then determining the functional effects on activity, as described above.

Samples or assays comprising ubiquitin ligation cascade proteins that are treated with a potential activator, inhibitor, or modulator are compared to control samples without the inhibitor, activator, or modulator to examine the extent of inhibition. Control samples (untreated with inhibitors) are assigned a relative protein activity value of 100%. Inhibition of ubiquitin ligation cascade proteins is achieved when the activity value relative to the control is about 80%, preferably 50%, more preferably 25-0%. Activation of ubiquitin ligation cascade proteins is achieved when the activity value relative to the control (untreated with activators) is 110%, more preferably 150%, more preferably 200-500% (i.e., two to five fold higher relative to the control), more preferably 1000-3000% higher.

The term "test compound" or "drug candidate" or "modulator" or grammatical equivalents as used herein describes any molecule, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, lipid, fatty acid, polynucleotide, oligonucleotide, etc., to be tested for the capacity to directly or indirectly modulation tumor cell proliferation. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 daltons and less than about 2500 daltons, preferably less than about 2000 daltons, preferably between about 100 to about 1000 daltons, more preferably between about 200 to about 500 daltons.

An "siRNA" molecule or an "RNAi molecule refers to a nucleic acid that forms a double stranded RNA, which double stranded RNA has the ability to reduce or inhibit expression of a gene or target gene when the siRNA expressed in the same cell as the gene or target gene. "siRNA" thus refers to the double stranded RNA formed by the complementary strands. The complementary portions of the siRNA that hybridize to form the double stranded molecule typically have substantial or complete identity. In one embodiment, an siRNA refers to a nucleic acid that has substantial or complete identity to a target gene and forms a double stranded siRNA. The sequence of the siRNA can correspond to the full length target gene, or a subsequence thereof. Typically, the siRNA is at least about 15-50 nucleotides in length (e.g., each complementary sequence of the double stranded siRNA is 15-50 nucleotides in length, and the double stranded siRNA is about 15-50 base pairs in length, preferable about preferably about 20-30 base nucleotides, preferably about 20-25 or about 24-29 nucleotides in length, e.g., 20, 21, 22, 23, 24, 25, 26, 27, 28, 29, or 30 nucleotides in length. See also PCT/US03/07237, herein incorporated by reference in its entirety.

An siRNA molecule or RNAi molecule is "specific" for a target nucleic acid if it reduces expression of the nucleic acid by at least about 10% when the siRNA or RNAi is expressed in a cell that expresses the target nucleic acid.

"Biological sample" include sections of tissues such as biopsy and autopsy samples, and frozen sections taken for histologic purposes. Such samples include blood, sputum, tissue, cultured cells, e.g., primary cultures, explants, and transformed cells, stool, urine, etc. A biological sample is typically obtained from a eukaryotic organism, most preferably a mammal such as a primate e.g., chimpanzee or human; cow; dog; cat; a rodent, e.g., guinea pig, rat, mouse; rabbit; or a bird; reptile; or fish.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region (e.g., nucleotide sequence or amino acid sequence of FIGS. 1-3), when compared and aligned for maximum correspondence over a comparison window or designated region) as measured using a BLAST or BLAST 2.0 sequence comparison algorithms with default parameters described below, or by manual alignment and visual inspection (see, e.g., NCBI web site www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. An example of potassium channel splice variants is discussed in Leicher, et al., *J. Biol. Chem.* 273(52):35095-35101 (1998).

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

Macromolecular structures such as polypeptide structures can be described in terms of various levels of organization. For a general discussion of this organization, see, e.g., Alberts et al., *Molecular Biology of the Cell* (3rd ed., 1994) and Cantor and Schimmel, *Biophysical Chemistry Part I: The Conformation of Biological Macromolecules* (1980). "Primary structure" refers to the amino acid sequence of a particular peptide. "Secondary structure" refers to locally ordered, three dimensional structures within a polypeptide. These structures are commonly known as domains, e.g., enzymatic domains (RING, ligase), extracellular domains, transmembrane domains, pore domains, and cytoplasmic tail domains. Domains are portions of a polypeptide that form a compact unit of the polypeptide and are typically 15 to 350 amino acids long. Exemplary domains include domains with enzymatic activity, e.g., a ligase or RING domain. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) *PCR Protocols, A Guide to Methods and Applications*, Academic Press, Inc. N.Y.).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990))

For preparation of antibodies, e.g., recombinant, monoclonal, or polyclonal antibodies, many technique known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* ($3^{rd}$ ed. 1997)). Techniques for the production of single chain antibodies or recombinant antibodies (U.S. Pat. Nos. 4,946,778, 4,816,567) can be adapted to produce antibodies to polypeptides of this invention. Also, transgenic mice, or other organisms such as other mammals, may be used to express human-ized or human antibodies (see, e.g., U.S. Pat. Nos. 5,545,807; 5,545,806; 5,569,825; 5,625,126; 5,633,425; 5,661,016, Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., *Nature* 321:522-525 (1986); Riechmann et al., *Nature* 332: 323-327 (1988); Verhoeyen et al., *Science* 239:1534-1536 (1988) and Presta, *Curr. Op. Struct. Biol.* 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

In one embodiment, the antibody is conjugated to an "effector" moiety. The effector moiety can be any number of molecules, including labeling moieties such as radioactive labels or fluorescent labels, or can be a therapeutic moiety. In one aspect the antibody modulates the activity of the protein.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies raised to a ubiquitin ligation cascade protein, polymorphic variants, alleles, orthologs, and conservatively modified variants, or splice variants, or portions thereof, can be selected to obtain only those polyclonal antibodies that are specifically immunoreactive with ubiquitin ligation cascade proteins and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity).

By "therapeutically effective dose" herein is meant a dose that produces effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); and Pickar, *Dosage Calculations* (1999)).

Assays for Proteins that Modulation the Inflammatory Process

High throughput functional genomics assays can be used to identify modulators of the inflammatory process. Such assays can monitor changes in cell surface marker expression, proliferation and differentiation, cell surface marker activation, response to cytokine signaling, and apoptosis, using either cell lines or primary cells. Typically, the cells are contacted with a cDNA library, an siRNA library, small molecules, antisense molecules, or a random peptide library (encoded by nucleic acids). In one embodiment, the peptides are cyclic or circular. The cDNA library can comprise sense, antisense, full length, and truncated cDNAs. The peptide library is encoded by nucleic acids. The effect of the cDNA, siRNA, or peptide library on the inflammatory process is then monitored, using an assay as described above. The effect of the cDNA, siRNA, or peptide can be validated and distinguished from somatic mutations, using, e.g., regulatable expression of the nucleic acid such as expression from a tetracycline promoter. cDNAs, siRNA and nucleic acids encoding peptides can be rescued using techniques known to those of skill in the art, e.g., using a sequence tag. Specific siRNA, cDNA, and peptide sequences can further be used for validation of specific target molecules.

Proteins interacting with the peptide or with the protein encoded by the cDNA can be isolated using a yeast two-hybrid system, mammalian two hybrid system, immunoprecipitation or affinity chromatography of complexed proteins followed by mass spectrometry, or phage display screen, etc. Association with a particular bait provides a disease association for the ubiquitin ligation cascade component. Association of a ubiquitin ligation cascade component with a specific bait indicates that the component is involved in ubiquitination of the bait. Targets so identified can be further used as bait in these assays to identify additional members of the inflammatory process, which members are also targets for drug development (see, e.g., Fields et al., *Nature* 340:245 (1989); Vasavada et al., *Proc. Nat'l Acad. Sci. USA* 88:10686 (1991); Fearon et al., *Proc. Nat'l Acad. Sci. USA* 89:7958 (1992); Dang et al., *Mol. Cell. Biol.* 11:954 (1991); Chien et al., *Proc. Nat'l Acad. Sci. USA* 9578 (1991); and U.S. Pat. Nos. 5,283,173, 5,667,973, 5,468,614, 5,525,490, and 5,637,463).

Suitable cell lines include A549, HeLa, Colo205, H1299, MCF7, MDA-MB-231, PC3, HUVEC, HMEC, PrEC, Jurkat, BJAB, HCT116, and cultured mast cells. Activation or inhibition of cell surface markers, e.g., ICAM, can be assayed using fluorescently labeled antibodies and FACS. Cell proliferation can be measured using $^3$H-thymidine incorporation, cell count by vital dye inclusion, MTT assay, BrdU incorporation, Cell Tracker assay. Apoptosis can be measured using dye inclusion, or by assaying for DNA laddering, increases in intracellular calcium, or caspase activation. Growth factor production can be measured using an immunoassay such as ELISA.

cDNA libraries are made from any suitable source. Libraries encoding random peptides are made according to techniques well known to those of skill in the art (see, e.g., U.S. Pat. Nos. 6,153,380, 6,114,111, and 6,180,343). Any suitable vector can be used for the cDNA and peptide libraries, including, e.g., retroviral vectors.

Isolation of Nucleic Acids Encoding Ubiquitin Ligation Cascade Components

This invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

Ubiquitin ligation cascade nucleic acids, polymorphic variants, orthologs, and alleles that are substantially identical to an amino acid sequence encoded by nucleic acids of FIGS. 1-3 can be isolated using nucleic acid probes and oligonucleotides under stringent hybridization conditions, by screening libraries. Alternatively, expression libraries can be used to clone the ubiquitin ligation cascade protein, polymorphic variants, orthologs, and alleles by detecting expressed homologs immunologically with antisera or purified antibodies made against human ubiquitin ligation cascade proteins or portions thereof.

To make a cDNA library, one should choose a source that is rich in the RNA of choice. The mRNA is then made into cDNA using reverse transcriptase, ligated into a recombinant vector, and transfected into a recombinant host for propagation, screening and cloning. Methods for making and screening cDNA libraries are well known (see, e.g., Gubler & Hoffman, *Gene* 25:263-269 (1983); Sambrook et al., supra; Ausubel et al., supra).

For a genomic library, the DNA is extracted from the tissue and either mechanically sheared or enzymatically digested to yield fragments of about 12-20 kb. The fragments are then separated by gradient centrifugation from undesired sizes and are constructed in bacteriophage lambda vectors. These vectors and phage are packaged in vitro. Recombinant phage are analyzed by plaque hybridization as described in Benton & Davis, *Science* 196:180-182 (1977). Colony hybridization is carried out as generally described in Grunstein et al., *Proc. Natl. Acad. Sci. USA.*, 72:3961-3965 (1975).

A preferred method of isolating ubiquitin ligation cascade nucleic acids and orthologs, alleles, mutants, polymorphic variants, splice variants, and conservatively modified variants combines the use of synthetic oligonucleotide primers and amplification of an RNA or DNA template (see U.S. Pat. Nos. 4,683,195 and 4,683,202; *PCR Protocols: A Guide to Methods and Applications* (Innis et al., eds, 1990)). Methods such as polymerase chain reaction (PCR and RT-PCR) and ligase chain reaction (LCR) can be used to amplify nucleic acid sequences directly from mRNA, from cDNA, from genomic libraries or cDNA libraries. Degenerate oligonucleotides can be designed to amplify homologs using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of ubiquitin ligation cascade component encoding mRNA in physiological samples, for nucleic acid sequencing, or for other purposes. Genes amplified by the PCR reaction can be purified from agarose gels and cloned into an appropriate vector.

Gene expression of ubiquitin ligation cascade components can also be analyzed by techniques known in the art, e.g., reverse transcription and amplification of mRNA, isolation of total RNA or poly $A^+$ RNA, northern blotting, dot blotting, in situ hybridization, RNase protection, high density polynucleotide array technology, e.g., and the like.

Nucleic acids encoding ubiquitin ligation cascade proteins can be used with high density oligonucleotide array technology (e.g., GeneChip™) to identify ubiquitin ligation cascade proteins, orthologs, alleles, conservatively modified variants, and polymorphic variants in this invention. In the case where the homologs being identified are linked to modulation of the inflammatory process, they can be used with GeneChip™ as a diagnostic tool in detecting the disease in a biological sample, see, e.g., Gunthand et al., *AIDS Res. Hum. Retroviruses* 14: 869-876 (1998); Kozal et al., *Nat. Med.* 2:753-759 (1996); Matson et al., *Anal. Biochem.* 224:110-106 (1995); Lockhart et al., *Nat. Biotechnol.* 14:1675-1680 (1996); Gingeras et al., *Genome Res.* 8:435-448 (1998); Hacia et al., *Nucleic Acids Res.* 26:3865-3866 (1998).

The gene of choice is typically cloned into intermediate vectors before transformation into prokaryotic or eukaryotic cells for replication and/or expression. These intermediate vectors are typically prokaryote vectors, e.g., plasmids, or shuttle vectors.

Expression in Prokaryotes and Eukaryotes

To obtain high level expression of a cloned gene, such as those cDNAs encoding ubiquitin ligation cascade proteins, one typically subclones the nucleic acid into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al., and Ausubel et al, supra. Bacterial expression systems for expressing the protein are available in, e.g., *E. coli, Bacillus sp.,* and *Salmonella* (Palva et al., *Gene* 22:229-235 (1983); Mosbach et al., *Nature* 302:543-545 (1983). Kits for such expression systems are commercially available. Eukaryotic expression systems for mammalian cells, yeast, and insect cells are well known in the art and are also commercially available. In one preferred embodiment, retroviral expression systems are used in the present invention.

Selection of the promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the nucleic acid in host cells. A typical expression cassette thus contains a promoter operably linked to the nucleic acid sequence encoding the nucleic acid of choice and signals required for efficient polyadenylation of the transcript, ribosome binding sites, and translation termination. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as MBP, GST, and LacZ. Epitope tags can also be added to recombinant proteins to provide convenient methods of isolation, e.g., c-myc. Sequence tags may be included in an expression cassette for nucleic acid rescue. Markers such as fluorescent proteins, green or red fluorescent protein, β-gal, CAT, and the like can be included in the vectors as markers for vector transduction.

Expression vectors containing regulatory elements from eukaryotic viruses are typically used in eukaryotic expression vectors, e.g., SV40 vectors, papilloma virus vectors, retroviral vectors, and vectors derived from Epstein-Barr virus. Other exemplary eukaryotic vectors include pMSG, pAV009/ $A^+$, pMTO10/$A^+$, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Expression of proteins from eukaryotic vectors can be also be regulated using inducible promoters. With inducible promoters, expression levels are tied to the concentration of inducing agents, such as tetracycline or ecdysone, by the incorporation of response elements for these agents into the promoter. Generally, high level expression is obtained from inducible promoters only in the presence of the inducing agent; basal expression levels are minimal.

In one embodiment, the vectors of the invention have a regulatable promoter, e.g., tet-regulated systems and the RU-486 system (see, e.g., Gossen & Bujard, *PNAS* 89:5547 (1992); Oligino et al., *Gene Ther.* 5:491-496 (1998); Wang et al., *Gene Ther.* 4:432-441 (1997); Neering et al., *Blood* 88:1147-1155 (1996); and Rendahl et al., *Nat. Biotechnol.* 16:757-761 (1998)). These impart small molecule control on the expression of the candidate target nucleic acids. This beneficial feature can be used to determine that a desired phenotype is caused by a transfected cDNA rather than a somatic mutation.

Some expression systems have markers that provide gene amplification such as thymidine kinase and dihydrofolate reductase. Alternatively, high yield expression systems not involving gene amplification are also suitable, such as using a baculovirus vector in insect cells, with a sequence of choice under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection methods are used to produce bacterial, mammalian, yeast or insect cell lines that express large quantities of protein, which are then purified using standard techniques (see, e.g., Colley et al., *J. Biol. Chem.* 264:17619-17622 (1989); *Guide to Protein Purification*, in *Methods in Enzymology*, vol. 182 (Deutscher, ed., 1990)). Transformation of eukaryotic and prokaryotic cells are performed according to standard techniques (see, e.g., Morrison, *J. Bact.* 132:349-351 (1977); Clark-Curtiss & Curtiss, *Methods in Enzymology* 101:347-362 (Wu et al., eds, 1983).

Any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing ubiquitin ligation cascade components.

After the expression vector is introduced into the cells, the transfected cells are cultured under conditions favoring expression of the protein of choice, which is recovered from the culture using standard techniques identified below.

Purification of Polypeptides

Either naturally occurring or recombinant ubiquitin ligation cascade components can be purified for use in functional assays. Naturally occurring protein can be purified, e.g., from human tissue. Recombinant protein can be purified from any suitable expression system.

The protein may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra, and Sambrook et al., supra).

A number of procedures can be employed when recombinant protein is being purified. For example, proteins having established molecular adhesion properties can be reversible fused to the protein. With the appropriate ligand or substrate, a specific protein can be selectively adsorbed to a purification column and then freed from the column in a relatively pure form. The fused protein is then removed by enzymatic activity. Finally, protein could be purified using immunoaffinity columns. Recombinant protein can be purified from any suitable source, include yeast, insect, bacterial, and mammalian cells.

A. Purification of Protein from Recombinant Bacteria

Recombinant proteins are expressed by transformed bacteria in large amounts, typically after promoter induction; but expression can be constitutive. Promoter induction with IPTG is one example of an inducible promoter system. Bacteria are grown according to standard procedures in the art. Fresh or frozen bacteria cells are used for isolation of protein.

Proteins expressed in bacteria may form insoluble aggregates ("inclusion bodies"). Several protocols are suitable for purification of protein inclusion bodies. For example, purification of inclusion bodies typically involves the extraction, separation and/or purification of inclusion bodies by disruption of bacterial cells, e.g., by incubation in a buffer of 50 mM TRIS/HCL pH 7.5, 50 mM NaCl, 5 mM $MgCl_2$, 1 mM DTT, 0.1 mM ATP, and 1 mM PMSF. The cell suspension can be lysed using 2-3 passages through a French Press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. Human proteins are separated from other bacterial proteins by standard separation techniques, e.g., with Ni-NTA agarose resin.

Alternatively, it is possible to purify recombinant protein from bacteria periplasm. After lysis of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

B. Standard Protein Separation Techniques for Purifying Proteins

Solubility Fractionation

Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size Differential Filtration

The molecular weight of the protein can be used to isolate it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatography

The protein can also be separated from other proteins on the basis of its size, net surface charge, hydrophobicity, and affinity for ligands or substrates. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

Assays for Modulators of Ubiquitin Ligation Cascade Proteins

A. Assays

Modulation of a ubiquitin ligation cascade protein, and corresponding modulation of the inflammatory process, e.g., lymphocyte and phagocyte proliferation, response to cytokine signaling, cell surface marker activation, etc., can be assessed using a variety of in vitro and in vivo assays, including cell-based models. Such assays can be used to test for inhibitors and activators of ubiquitin ligation cascade protein, and, consequently, inhibitors and activators of the inflammatory process. Such modulators of ubiquitin ligation cascade protein are useful for treating disorders related to the inflammatory process, e.g., infection and autoimmune disease. Modulators of ubiquitin ligation cascade protein are tested using either recombinant or naturally occurring protein of choice, preferably human ubiquitin ligation cascade protein.

Preferably, the ubiquitin ligation cascade protein will have the sequence as encoded by a sequence as shown in FIGS. 1-3 or a conservatively modified variant thereof. Alternatively, the ubiquitin ligation cascade protein of the assay will be derived from a eukaryote and include an amino acid subsequence having substantial amino acid sequence identity to a sequence as shown in FIGS. 1-3. Generally, the amino acid sequence identity will be at least 60%, preferably at least 65%, 70%, 75%, 80%, 85%, or 90%, most preferably at least 95%.

Measurement of inflammation modulation with ubiquitin ligation cascade protein or a cell expressing ubiquitin ligation cascade protein, either recombinant or naturally occurring, can be performed using a variety of assays, in vitro, in vivo, and ex vivo, as described herein. A suitable physical, chemical or phenotypic change that affects activity, e.g., enzymatic activity such as ligase activity, cell surface marker expression, cell proliferation, cell cycle perturbation or arrest, or ligand or substrate binding can be used to assess the influence of a test compound on the polypeptide of this invention. When the functional effects are determined using intact cells or animals, one can also measure a variety of effects, such as, ligand binding, ligase activity, transcriptional changes to both known and uncharacterized genetic markers (e.g., northern blots), response to cytokine signaling, changes in cell metabolism, changes related to cellular proliferation, cell surface marker expression (ICAM), DNA synthesis, marker and dye dilution assays (e.g., GFP and cell tracker assays), etc.

In Vitro Assays

Assays to identify compounds with ubiquitin ligation cascade protein modulating activity can be performed in vitro. Such assays can used full length ubiquitin ligation cascade protein or a variant thereof, or a mutant thereof, or a fragment thereof, such as a RING domain. Purified recombinant or naturally occurring protein can be used in the in vitro methods of the invention. In addition to purified ubiquitin ligation cascade protein, the recombinant or naturally occurring protein can be part of a cellular lysate or a cell membrane. As described below, the binding assay can be either solid state or soluble. Preferably, the protein or membrane is bound to a solid support, either covalently or non-covalently. Often, the in vitro assays of the invention are substrate or ligand binding or affinity assays, either non-competitive or competitive. Other in vitro assays include measuring changes in spectroscopic (e.g., fluorescence, absorbance, refractive index), hydrodynamic (e.g., shape), chromatographic, or solubility properties for the protein.

In a preferred assay, a ubiquitin conjugation or ligase assay is performed as described in WO 01/75145 (incorporated by referenced in its entirety), Examples 2 and 3, using a recombinant E1, E2, or E3 of choice, as listed in FIGS. 1-3, as well as complementary members of the ubiquitin ligation cascade (see also U.S. Ser. Nos. 09/542,497, 09/826,312, and 10/108,767, herein incorporated by reference in their entirety). A substrate is optional.

In one embodiment, a high throughput binding assay is performed in which the protein or a fragment thereof is contacted with a potential modulator and incubated for a suitable amount of time. In one embodiment, the potential modulator is bound to a solid support, and the protein is added. In another embodiment, the protein is bound to a solid support. A wide variety of modulators can be used, as described below, including small organic molecules, peptides, antibodies, and ubiquitin ligation cascade component ligand or substrate analogs. A wide variety of assays can be used to identify ubiquitin ligation cascade component-modulator binding, including labeled protein-protein binding assays, electrophoretic mobility shifts (e.g., measuring ubiquitination of a substrate), immunoassays, enzymatic assays such as ligase assays, and the like. In some cases, the binding of the candidate modulator is determined through the use of competitive binding assays, where interference with binding of a known ligand or substrate is measured in the presence of a potential modulator. Either the modulator or the known ligand or substrate is bound first, and then the competitor is added. After the ubiquitin ligation cascade component protein is washed, interference with binding, either of the potential modulator or of the known ligand or substrate, is determined. Often, either the potential modulator or the known ligand or substrate is labeled.

Cell-Based In Vivo Assays

In another embodiment, the ubiquitin ligation cascade protein is expressed in a cell, and functional, e.g., physical and chemical or phenotypic, changes are assayed to identify modulators of the inflammatory process. Cells expressing ubiquitin ligation cascade proteins can also be used in enzymatic assays. Any suitable functional effect can be measured, as described herein. For example, cellular morphology (e.g., cell volume, nuclear volume, cell perimeter, nuclear perimeter, DNA replication), ligand binding, ligase activity, apoptosis, cell surface marker expression (e.g., ICAM), cellular proliferation, GFP positivity and dye dilution assays (e.g., cell tracker assays with dyes that bind to cell membranes), DNA synthesis or content assays (e.g., $^3$H-thymidine and fluorescent DNA-binding dyes such as DAPI, BrdU or Hoescht dye with FACS analysis), are all suitable assays to identify potential modulators using a cell based system. Suitable cells for such cell based assays include both primary cancer or tumor cells, lymphocytes, phagocytic cells, PBMC, and cell lines, as described herein, e.g., A549 (lung), MCF7 (breast, p53 wild-type), H1299 (lung, p53 null), Hela (cervical), PC3 (prostate, p53 mutant), MDA-MB-231 (breast, p53 wild-type), Jurkat (T cell), BJAB (B cell), HUVEC, HMEC, RAMOS, LanCap, and HCT116. The ubiquitin ligation cascade protein can be naturally occurring or recombinant. Also, fragments of the ubiquitin ligation cascade protein or chimeric proteins can be used in cell based assays. In addition, point mutants in the catalytic site or in essential residues required by the catalytic site can be used in these assays.

Cellular ubiquitin ligation cascade polypeptide levels can be determined by measuring the level of protein or mRNA. The level of protein or proteins related to the ubiquitin ligation cascade protein is measured using immunoassays such as western blotting, ELISA and the like with an antibody that selectively binds to the ubiquitin ligation cascade polypeptide or a fragment thereof. For measurement of mRNA, amplification, e.g., using multiplex RT-PCR, PCR, LCR, or hybridization assays, e.g., northern hybridization, RNAse protection, dot blotting, are preferred. The level of protein or mRNA is detected using directly or indirectly labeled detection agents, e.g., fluorescently or radioactively labeled nucleic acids, radioactively or enzymatically labeled antibodies, and the like, as described herein.

Alternatively, regulation of ubiquitin ligation cascade protein expression can be measured using a reporter gene system. Such a system can be devised using a promoter operably linked to a reporter gene such as chloramphenicol acetyltransferase, firefly luciferase, bacterial luciferase, β-galactosidase and alkaline phosphatase. In one embodiment, the ubiquitin substrate level is measured using the reporter. Furthermore, the protein of interest can be used as an indirect reporter via attachment to a second reporter such as red or green fluorescent protein (see, e.g., Mistili & Spector, *Nature Biotechnology* 15:961-964 (1997)). The reporter construct is typically transfected into a cell. After treatment with a potential modulator, the amount of reporter gene transcription, translation, or activity is measured according to standard techniques known to those of skill in the art.

In a preferred embodiment, ICAM activation is measured after stimulation by TNF-α, IL-1β, and INF-γ, followed by FACS analysis (see Example 3).

Animal Models

Animal models of cellular proliferation also find use in screening for modulators of inflammation. Similarly, transgenic animal technology including gene knockout technology, for example as a result of homologous recombination with an appropriate gene targeting vector, or gene overexpression, will result in the absence or increased expression of the ubiquitin ligation cascade protein. The same technology can also be applied to make knock-out cells. When desired, tissue-specific expression or knockout of the ubiquitin ligation cascade protein may be necessary. Transgenic animals generated by such methods find use as animal models of inflammation and are additionally useful in screening for modulators of inflammation.

Knock-out cells and transgenic mice can be made by insertion of a marker gene or other heterologous gene into an endogenous ubiquitin ligation cascade gene site in the mouse genome via homologous recombination. Such mice can also be made by substituting an endogenous ubiquitin ligation cascade protein with a mutated version of the gene, or by mutating an endogenous ubiquitin ligation cascade protein, e.g., by exposure to carcinogens.

A DNA construct is introduced into the nuclei of embryonic stem cells. Cells containing the newly engineered genetic lesion are injected into a host mouse embryo, which is re-implanted into a recipient female. Some of these embryos develop into chimeric mice that possess germ cells partially derived from the mutant cell line. Therefore, by breeding the chimeric mice it is possible to obtain a new line of mice containing the introduced genetic lesion (see, e.g., Capecchi et al., *Science* 244:1288 (1989)). Chimeric targeted mice can be derived according to Hogan et al., *Manipulating the Mouse Embryo: A Laboratory Manual*, Cold Spring Harbor Laboratory (1988) and *Teratocarcinomas and Embryonic Stem Cells: A Practical Approach*, Robertson, ed., IRL Press, Washington, D.C., (1987).

Exemplary Cell Cycle Assays

Apoptosis Analysis

Apoptosis analysis can be used as an assay to identify ubiquitin ligation cascade modulators. In this assay, cell lines, such as RKO or HCT116, can be used to screen for inflammation modulators. Cells are contacted with a putative modulator. The cells can be co-transfected with a construct comprising a marker gene, such as a gene that encodes green fluorescent protein, or a cell tracker dye, or BRDU. The apoptotic change can be determined using methods known in the art, such as DAPI staining and TUNEL assay using fluorescent microscope. For TUNEL assay, commercially available kit can be used (e.g., Fluorescein FragEL DNA Fragmentation Detection Kit (Oncogene Research Products, Cat.#QIA39)+Tetramethyl-rhodamine-5-dUTP (Roche, Cat. #1534 378)). Cells contacted with modulators would exhibit, e.g., an increased apoptosis compared to control.

Cell Cycle Arrest Analysis

Cell cycle arrest can be used as an assay to identify ubiquitin ligation cascade modulators. Any phase of the cell cycle can be measured in this assay, e.g., $G_1$, S, $G_2$, and M, also the $G_0$ state, as well as apoptosis. In this assay, cell lines, such as A549, HeLa, HTVEC, HMEC, prostate cells, RKO or HCT116, can be used to screen ubiquitin ligation cascade modulators. The cells can be co-transfected with a construct comprising a marker gene, such as a gene that encodes green fluorescent protein, or the cells can be contacted with a dye such as a cell tracker dye or BRDU. Methods known in the art can be used to measure the degree of cell cycle arrest. For example, a propidium iodide signal or other dye can be used as a measure for DNA content or synthesis to determine cell cycle profiles on a flow cytometer using FACS. The percent of the cells in each cell cycle can be calculated. Cells contacted with a ubiquitin ligation cascade modulator would exhibit, e.g., a higher number of cells that are arrested in the selected cell cycle phase ($G_1$, S, $G_2$, and M, also the $G_0$ state) compared to control phases of the cell cycle.

B. Modulators

The compounds tested as modulators of ubiquitin ligation cascade protein can be any small organic molecule, or a biological entity, such as a protein, e.g., an antibody or peptide, a sugar, a nucleic acid, e.g., an antisense oligonucleotide or a ribozyme or RNAi, or a lipid. Alternatively, modulators can be genetically altered versions of a ubiquitin ligation cascade protein. Typically, test compounds will be small organic molecules, peptides, circular peptides, RNAi, antisense molecules, ribozymes, and lipids.

Essentially any chemical compound can be used as a potential modulator or ligand in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods involve providing a combinatorial small organic molecule or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology,* 14(3):309-314 (1996) and PCT/US96/10287), carbohydrate libraries (see, e.g., Liang et al., *Science,* 274:1520-1522 (1996) and U.S. Pat. No. 5,593,853), small organic molecule libraries (see, e.g., benzodiazepines, Baum C&EN, Jan 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

C. Solid State and Soluble High Throughput Assays

In one embodiment the invention provides soluble assays using a ubiquitin ligation cascade protein, or a cell or tissue expressing an ubiquitin ligation cascade protein, either naturally occurring or recombinant. In another embodiment, the invention provides solid phase based in vitro assays in a high throughput format, where the ubiquitin ligation cascade protein or ubiquitin ligation cascade substrate is attached to a solid phase. Any one of the assays described herein can be adapted for high throughput screening.

In the high throughput assays of the invention, either soluble or solid state, it is possible to screen up to several thousand different modulators or ligands in a single day. This methodology can be used for ubiquitin ligation cascade proteins in vitro, or for cell-based or membrane-based assays comprising a ubiquitin ligation cascade protein. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100- about 1500 different compounds. It is possible to assay many plates per day; assay screens for up to about 6,000, 20,000, 50,000, or more than 100,000 different compounds are possible using the integrated systems of the invention.

For a solid state reaction, the protein of interest or a fragment thereof, e.g., an extracellular domain, or a cell or membrane comprising the protein of interest or a fragment thereof as part of a fusion protein can be bound to the solid state component, directly or indirectly, via covalent or non covalent linkage. A tag for covalent or non-covalent binding can be any of a variety of components. In general, a molecule which binds the tag (a tag binder) is fixed to a solid support, and the tagged molecule of interest is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.) Antibodies to molecules with natural binders such as biotin are also widely available and appropriate tag binders; see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherein family, the integrin family, the selectin family, and the like; see, e.g., Pigott & Power, *The Adhesion Molecule Facts Book I* (1993). Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly gly sequences of between about 5 and 200 amino acids. Such flexible linkers are known to persons of skill in the art. For example, poly(ethelyne glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.* 85:2149-2154 (1963) (describing solid phase synthesis of, e.g., peptides); Geysen et al., *J. Immun. Meth.* 102:259-274 (1987) (describing synthesis of solid phase components on pins); Frank & Doring, *Tetrahedron* 44:60316040 (1988) (describing synthesis of various peptide sequences on cellulose disks); Fodor et al., *Science,* 251:767-777 (1991); Sheldon et al., *Clinical Chemistry* 39(4):718-719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

Immunological Detection of Polypeptides

In addition to the detection of a ubiquitin ligation cascade gene and gene expression using nucleic acid hybridization technology, one can also use immunoassays to detect ubiquitin ligation cascade proteins of the invention. Such assays are useful for screening for modulators of ubiquitin ligation cascade proteins, as well as for therapeutic and diagnostic applications. Immunoassays can be used to qualitatively or quantitatively analyze ubiquitin ligation cascade protein. A general overview of the applicable technology can be found in Harlow & Lane, *Antibodies: A Laboratory Manual* (1988).

A. Production of Antibodies

Methods of producing polyclonal and monoclonal antibodies that react specifically with ubiquitin ligation cascade proteins are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature* 256: 495-497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275-1281 (1989); Ward et al., *Nature* 341:544-546 (1989)).

A number of immunogens comprising portions of a ubiquitin ligation cascade protein may be used to produce antibodies specifically reactive with the ubiquitin ligation cascade protein. For example, a recombinant ubiquitin ligation cascade protein or an antigenic fragment thereof, can be isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the beta subunits. When appropriately high titers of antibody to the immunogen are obtained, blood is collected from the animal and antisera are prepared. Further fractionation of the antisera to enrich for antibodies reactive to the protein can be done if desired (see, Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see, Kohler & Milstein, *Eur. J. Immunol.* 6:511-519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse, et al., *Science* 246:1275-1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-ubiquitin ligation cascade proteins, using a competitive binding immunoassay. Specific polyclonal antisera and monoclonal antibodies will usually bind with a $K_d$ of at least about 0.1 mM, more usually at least about 1 µM, preferably at least about 0.1 µM or better, and most preferably, 0.01 µM or better. Antibodies specific only for a particular ubiquitin ligation cascade protein ortholog, such as a human ortholog, can also be made, by subtracting out other cross-reacting orthologs from a species such as a non-human mammal. In this manner, antibodies that bind only to the protein of choice may be obtained.

Once the specific antibodies against a ubiquitin ligation cascade protein are available, the protein can be detected by a variety of immunoassay methods. In addition, the antibody can be used therapeutically as a ubiquitin ligation cascade protein modulators. For a review of immunological and immunoassay procedures, see *Basic and Clinical Immunology* (Stites & Terr eds., 7$^{th}$ ed. 1991). Moreover, the immunoassays of the present invention can be performed in any of several configurations, which are reviewed extensively in Enzyme Immunoassay (Maggio, ed., 1980); and Harlow & Lane, supra.

B. Immunological Binding Assays

Protein can be detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology: Antibodies in Cell Biology*, volume 37 (Asai, ed. 1993); *Basic and Clinical Immunology* (Stites & Terr, eds., 7th ed. 1991). Immunological binding assays (or immunoassays) typically use an antibody that specifically binds to a protein or antigen of choice (in this case the ubiquitin ligation cascade protein or antigenic subsequence thereof). The antibody (e.g., anti-ubiquitin ligation cascade protein) may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled ubiquitin ligation cascade protein or a labeled anti-ubiquitin ligation cascade protein antibody. Alternatively, the labeling agent may be a third moiety, such a secondary antibody, that specifically binds to the antibody/antigen complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see, e.g., Kronval et al., *J. Immunol.* 111:1401-1406 (1973); Akerstrom et al., *J. Immunol.* 135:2589-2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, optionally from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

Non-Competitive Assay Formats

Immunoassays for detecting ubiquitin ligation cascade protein in samples may be either competitive or noncompetitive. Noncompetitive immunoassays are assays in which the amount of antigen is directly measured. In one preferred "sandwich" assay, for example, the anti-ubiquitin ligation cascade protein antibodies can be bound directly to a solid substrate on which they are immobilized. These immobilized antibodies then capture the ubiquitin ligation cascade protein present in the test sample. Proteins thus immobilized are then bound by a labeling agent, such as a second ubiquitin ligation cascade protein antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

Competitive Assay Formats

In competitive assays, the amount of ubiquitin ligation cascade protein present in the sample is measured indirectly by measuring the amount of a known, added (exogenous) ubiquitin ligation cascade protein displaced (competed away) from an anti-ubiquitin ligation cascade protein antibody by the unknown ubiquitin ligation cascade protein present in a sample. In one competitive assay, a known amount of ubiquitin ligation cascade protein is added to a sample and the sample is then contacted with an antibody that specifically binds to ubiquitin ligation cascade protein. The amount of exogenous ubiquitin ligation cascade protein bound to the antibody is inversely proportional to the concentration of ubiquitin ligation cascade protein present in the sample. In a particularly preferred embodiment, the antibody is immobilized on a solid substrate. The amount of ubiquitin ligation cascade protein bound to the antibody may be determined either by measuring the amount of ubiquitin ligation cascade protein present in ubiquitin ligation cascade protein/antibody complex, or alternatively by measuring the amount of remaining uncomplexed protein. The amount of ubiquitin ligation cascade protein may be detected by providing a labeled ubiquitin ligation cascade molecule.

A hapten inhibition assay is another preferred competitive assay. In this assay the known ubiquitin ligation cascade protein is immobilized on a solid substrate. A known amount of anti-ubiquitin ligation cascade protein antibody is added to the sample, and the sample is then contacted with the immobilized ubiquitin ligation cascade protein. The amount of anti-ubiquitin ligation cascade protein antibody bound to the known immobilized ubiquitin ligation cascade protein is inversely proportional to the amount of ubiquitin ligation cascade protein present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Cross-Reactivity Determinations

Immunoassays in the competitive binding format can also be used for crossreactivity determinations. For example, a ubiquitin ligation cascade protein can be immobilized to a solid support. Proteins are added to the assay that compete for binding of the antisera to the immobilized antigen. The ability of the added proteins to compete for binding of the antisera to the immobilized protein is compared to the ability of the ubiquitin ligation cascade protein to compete with itself. The percent crossreactivity for the above proteins is calculated, using standard calculations. Those antisera with less than 10% crossreactivity with each of the added proteins listed above are selected and pooled. The cross-reacting antibodies are optionally removed from the pooled antisera by immunoabsorption with the added considered proteins, e.g., distantly related homologs.

The immunoabsorbed and pooled antisera are then used in a competitive binding immunoassay as described above to compare a second protein, thought to be perhaps an allele or polymorphic variant of a ubiquitin ligation cascade protein, to the immunogen protein. In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the ubiquitin ligation cascade protein that is required to inhibit 50% of binding, then the second protein is said to specifically bind to the polyclonal antibodies generated to ubiquitin ligation cascade immunogen.

Other Assay Formats

Western blot (immunoblot) analysis is used to detect and quantify the presence of ubiquitin ligation cascade protein in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind the ubiquitin ligation cascade protein. The anti-ubiquitin ligation cascade protein antibodies specifically bind to the ubiquitin ligation cascade protein on the solid support. These antibodies may be directly labeled or alternatively may be subsequently detected using labeled antibodies (e.g., labeled sheep anti-mouse antibodies) that specifically bind to the anti-ubiquitin ligation cascade protein antibodies.

Other assay formats include liposome immunoassays (LIA), which use liposomes designed to bind specific molecules (e.g., antibodies) and release encapsulated reagents or markers. The released chemicals are then detected according to standard techniques (see Monroe et al., *Amer. Clin. Prod. Rev.* 5:34-41 (1986)).

Reduction of Non-Specific Binding

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize ubiquitin ligation cascade protein, or secondary antibodies that recognize anti-ubiquitin ligation cascade protein.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by the use of electronic detectors such as charge coupled devices (CCDs) or photomultipliers and the like. Similarly, enzymatic labels may be detected by providing the appropriate substrates for the enzyme and detecting the resulting reaction product. Colorimetric or chemiluminescent labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

Cellular Transfection and Gene Therapy

The present invention provides the nucleic acids of ubiquitin ligation cascade protein for the transfection of cells in vitro and in vivo. These nucleic acids can be inserted into any of a number of well-known vectors for the transfection of target cells and organisms as described below. The nucleic acids are transfected into cells, ex vivo or in vivo, through the interaction of the vector and the target cell. The nucleic acid, under the control of a promoter, then expresses a ubiquitin ligation cascade protein of the present invention, thereby mitigating the effects of absent, partial inactivation, or abnormal expression of a ubiquitin ligation cascade gene, particularly as it relates to inflammation. The compositions are administered to a patient in an amount sufficient to elicit a therapeutic response in the patient. An amount adequate to accomplish this is defined as "therapeutically effective dose or amount."

Such gene therapy procedures have been used to correct acquired and inherited genetic defects, cancer, and other diseases in a number of contexts. The ability to express artificial genes in humans facilitates the prevention and/or cure of many important human diseases, including many diseases which are not amenable to treatment by other therapies (for a review of gene therapy procedures, see Anderson, *Science* 256:808-813 (1992); Nabel & Felgner, TIBTECH 11:211-217 (1993); Mitani & Caskey, TIBTECH 11:162-166 (1993); Mulligan, *Science* 926-932 (1993); Dillon, TIBTECH 11:167-175 (1993); Miller, *Nature* 357:455-460 (1992); Van Brunt, *Biotechnology* 6(10):1149-1154 (1998); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* (Doerfler & Böhm eds., 1995); and Yu et al., *Gene Therapy* 1:13-26 (1994)).

Pharmaceutical Compositions and Administration

Pharmaceutically acceptable carriers are determined in part by the particular composition being administered (e.g., nucleic acid, protein, modulatory compounds or transduced cell), as well as by the particular method used to administer the composition. Accordingly, there are a wide variety of suitable formulations of pharmaceutical compositions of the present invention (see, e.g., *Remington's Pharmaceutical Sciences*, 17$^{th}$ ed., 1989). Administration can be in any convenient manner, e.g., by injection, oral administration, inhalation, transdermal application, or rectal administration.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration and intravenous administration are the preferred methods of administration. The formulations of commends can be presented in unit-dose or multi-dose sealed containers, such as ampules and vials.

Injection solutions and suspensions can be prepared from sterile powders, granules, and tablets of the kind previously described. Cells transduced by nucleic acids for ex vivo therapy can also be administered intravenously or parenterally as described above.

The dose administered to a patient, in the context of the present invention should be sufficient to effect a beneficial therapeutic response in the patient over time. The dose will be determined by the efficacy of the particular vector employed and the condition of the patient, as well as the body weight or surface area of the patient to be treated. The size of the dose also will be determined by the existence, nature, and extent of any adverse side-effects that accompany the administration of a particular vector, or transduced cell type in a particular patient.

In determining the effective amount of the vector to be administered in the treatment or prophylaxis of conditions owing to diminished or aberrant expression of the protein, the physician evaluates circulating plasma levels of the vector, vector toxicities, progression of the disease, and the production of anti-vector antibodies. In general, the dose equivalent of a naked nucleic acid from a vector is from about 1 µg to 100 µg for a typical 70 kilogram patient, and doses of vectors which include a retroviral particle are calculated to yield an equivalent amount of therapeutic nucleic acid.

For administration, compounds and transduced cells of the present invention can be administered at a rate determined by the LD-50 of the inhibitor, vector, or transduced cell type, and the side-effects of the inhibitor, vector or cell type at various concentrations, as applied to the mass and overall health of the patient. Administration can be accomplished via single or divided doses.

EXAMPLES

The following examples are offered to illustrate, but not to limit the claimed invention.

Example 1

Yeast Two-Hybrid Assays

Members of the ubiquitin ligation cascade identified herein were isolated in a yeast two-hybrid screen baited with known proteins such as FRIP/DOK2, a ras GAP binding adaptor protein that plays a role in IL-4 and EGF receptor signaling; MYT1, which is a Wee1 family member that regulates cdc2 and G-S transitions during cell cycle progression; and XIAP, which is an IAP family member that inhibits pro-apoptotic caspase pathways (for other baits, see FIG. 1, column 6, and FIG. 2, column 7. UBcH6 and FLJ25157 bound to FRIP, MMS, UEV1, and CDC34 bound to Myt1, and Ubc13 bound to XIAP (for other baits and hits, see FIG. 1, column 1 and FIG. 2, column 1). Proteins interacting with the bait peptide are isolated using yeast two-hybrid systems or mammalian two hybrid systems known to those of skill in the art (see, e.g., Fields et al., *Nature* 340:245 (1989); Vasavada et al., *PNAS USA* 88:10686 (1991); Fearon et al., *PNAS USA* 89:7958 (1992); Dang et al., *Mol. Cell. Biol.* 11:954 (1991); Chien et al., *PNAS USA* 9578 (1991); and U.S. Pat. Nos. 5,283,173, 5,667,973, 5,468,614, 5,525,490, and 5,637,463).

Example 2

Selection of siRNA Target Sites for Phenotype Assays siRNA was used to inhibit selected target molecules, whose function was then examined in phenotype assays, e.g., inflammation assays such as ICAM induction assays.

Begin with the AUG start codon of the mRNA to be targeted, skip the first 75 bases and scan downstream for AA dinucleotide sequences. Record the occurrence of each AA and the 3' adjacent 19 nucleotides as potential siRNA target sites (the two base pair sequences 3' to the 19 mer do not seem to matter). There is no indication that a longer siRNA will do better than the current 21 mer used herein, however, longer siRNA molecules can be designed.

Tuschl, et al. recommend against designing siRNA to the 5' and 3' untranslated regions (UTRs) and regions near the start codon (within 75 bases) as these may be richer in regulatory protein binding sites. UTR-binding proteins and/or translation initiation complexes may interfere with binding of the siRNA endonuclease complex.

Check each potential target sites and make sure its GC content is between 30-70% and it does not have a stretch of more than 4 Gs or Cs.

Check each potential target sites (using BLAST search for human genes) and make sure it does not sit on an intron/exon boundary.

Check and make sure each potential target site does not contain a SNP.

Compare the potential target sites to the appropriate database and eliminate from consideration any target sequences with significant homology (with a stretch of bases>=16 nucleotides or so identical) to other coding sequences.

Select 3 to 4 target sequences along the length of the gene to evaluate whether the 5', 3', or medial portions of mRNAs are more susceptible to siRNA induced degradation.

Example 3

ICAM (CD54) Induction Assay for Identification of Molecules Involved in the Inflammatory Process The ICAM upregulation assay models the inflammatory process and cytokine signaling. ICAM is an adhesion molecule that is expressed on the surface of cells at local sites of inflammation. ICAM expression is induced in the presence of various cytokines such as IL-1β, TNFα, and IFNγ. Each cytokine acts through different signaling molecules therefore this assay can delineate the specificity of a particular genetic effector (e.g., trans dominant effectors such as siRNA, nucleic acids encoding peptides, antisense molecules, small organic molecules, or cDNA, or a dominant negative mutant cDNA).

Day 1: Split cells (A549, HBEC, or HUVEC) cells $4.5 \times 10^4$ in a 24 well plate in the appropriate media and incubate at 37° C., 5% C02.

Day 2: Cells should be 40-50% confluent siRNA: Transfect siRNA into cells with oligofectamine. Pipet out the media and replace it with 500 uL of fresh media. Mix 3 uL of 20 uM siRNA duplexes with 50 uL of Optimem media. Add 3 uL of oligofectamine to 12 uL Optimen. Wait 7-10 minutes. Combine the two solutions and pipet up and gently pipet up and down 3 times. Wait 20-25 minutes. Add 32 uL of Optimen to adjust the volume to 100 uL. Add the entire mixture to the cells.

Retroviral: Infect cells using a standard spin infection protocol.

Day 3: Add 0.5 mL of fresh media.

Day 4: Wash cells in 1 mL PBS, remove PBS and add 100 uL of Trypsin/EDTA. 5 min later add 100 uL of FK12. Pipet 4x up and down then transfer the cells to a V-bottom 96 well plate. Spin down at 1200 rpm for 3 min. Resuspend in 200 uL of fresh media. Count representative wells by hemocytometer then compute the average cells/mi. Plate $1.5 \times 10^4$ cells/well in a 96 well plate, the total final volume is 50 uL.

Day 5: Add 50 uL of a 2x cytokine mixture; the final concentrations of recombinant IL-1β, TNFα, and IFNγ should be 75 ng/mL. All cytokines can be purchased from Peprotech as a lyophilized powder.

Day 6: Stain cells and FACs analysis. Rinse the cells 1×200 uL PBS. Add 50 uL of Trypsin/EDTA-Incubate 5 min at 37° C. Add 150 uL of PBS-2% FCS—Pipet up and down 5x and transfer to a V-bottom 96 well plate. Spin down and wash 1x in 200 uL PBS-EDTA, flick out solution. Add 25 uL of a 1:7 dilution of ICAM-APC (Pharmingen). Pipet up and down gently 4x to resuspend the cells. Incubate in the dark for 15 min at 4° C. Add 175 uL of PBS-2% FCS. Spin down at 2000 rpm for 30 sec. Wash once with 200 uL PBS-2% FCS. Add 150 uL of PBS-2%, resuspend the cells, then transfer to cluster tubes. Perform FACS analysis on FL4-APC for siRNA analysis, FL4-APC vs. FL1-GFP for retroviral IRES or GFP-fusion analysis.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

We claim:

1. A method for identifying a compound that modulates the inflammatory process, the method comprising:
   (i) contacting the compound with a polypeptide having a sequence at least 95% identical to a full length E2 protein of SEQ ID NO: 38, said polypeptide having ubiquitin conjugation activity; and
   (ii) identifying a candidate modulator of the inflammatory process by determining the effect of the compound on the polypeptide in a ubiquitin ligase assay, wherein differential ubiquitin conjugating activity in the absence and presence of the compound indicates that the compound is a modulator of the inflammatory process.

2. The method of claim 1, wherein the polypeptide is recombinant.

3. The method of claim 1, wherein the compound is an antibody.

4. The method of claim 1, wherein the compound is a small organic molecule.

5. The method of claim 1, wherein the compound is a peptide.

6. The method of claim 5, wherein the peptide is circular.

7. The method of claim 1, further comprising;
   (iii) contacting said candidate modulator with a lymphocyte cell; and
   (iv) determining the effect of the candidate modulator upon an indicator of lymphocyte function selected from the group consisting of lymphocyte activation, lymphocyte proliferation, lymphocyte apoptosis, activation of ICAM, and induction of ICAM expression, wherein an increase or decrease of said indicator as compared to an untreated control identifies the compound as a modulator of the inflammatory process.

* * * * *

SEQUENCE LISTING

<160> NUMBER OF SEQ ID NOS: 82

<210> SEQ ID NO 1
<211> LENGTH: 3504
<212> TYPE: DNA
<213> ORGANISM: Homo sapiens
<220> FEATURE:
<221> NAME/KEY: misc_feature
<223> OTHER INFORMATION: GenBank Accession No.: NM_003334

<400> SEQUENCE: 1

| | | | | | |
|---|---|---|---|---|---|
| gagaaggcgg | cagcggcgat | tctaggcggc | ccaggcggcg | ggaggagga | gaaggaggag | 60 |
| ggtggcggcc | gggcttggct | tcggctcctt | gaggagttgg | cggcggcgcg | acccggggaa | 120 |
| ccggcattga | tgtccagctc | gccgctgtcc | aagaaacgtc | gcgtgtccgg | gcctgatcca | 180 |
| aagccgggtt | ctaactgctc | ccctgcccag | tccgtgttgt | ccgaagtgcc | ctcggtgcca | 240 |
| accaacggaa | tggccaagaa | cggcagtgaa | gcagacatag | acgagggcct | ttactcccgg | 300 |
| cagctgtatg | tgttgggcca | tgaggcaatg | aagcggctcc | agacatccag | tgtcctggta | 360 |
| tcaggcctgc | ggggcctggg | cgtggagatc | gctaagaaca | tcatccttgg | tggggtcaag | 420 |
| gctgttaccc | tacatgacca | gggcactgcc | cagtgggctg | atctttcctc | ccagttctac | 480 |
| ctgcggggag | aggacatcgg | taaaaaccgg | gccgaggtat | cacagccccg | cctcgctgag | 540 |
| ctcaacagct | atgtgcctgt | cactgcctac | actggacccc | tcgttgagga | cttccttagt | 600 |
| ggtttccagg | tggtggtgct | caccaacacc | cccctggagg | accagctgcg | agtgggtgag | 660 |
| ttctgtcaca | accgtggcat | caagctggtg | gtggcagaca | cgcggggcct | gtttgggcag | 720 |
| ctcttctgtg | actttggaga | ggaaatgatc | ctcacagatt | ccaatgggga | gcagccactc | 780 |
| agtgctatgg | tttctatggt | taccaaggac | aaccccggtg | tggttacctg | cctggatgag | 840 |
| gcccgacacg | ggtttgagag | cggggacttt | gtctcctttt | cagaagtaca | gggcatggtt | 900 |
| gaactcaacg | gaaatcagcc | catggagatc | aaagtcctgg | gtccttatac | ctttagcatc | 960 |
| tgtgacacct | ccaacttctc | cgactacatc | cgtggaggca | tcgtcagtca | ggtcaaagta | 1020 |
| cctaagaaga | ttagctttaa | atccttggtg | gcctcactgg | cagaacctga | ctttgtggtg | 1080 |
| acggacttcg | ccaagttttc | tcgccctgcc | cagctgcaca | ttggcttcca | ggccctgcac | 1140 |
| cagttctgtg | ctcagcatgg | ccggccacct | cggccccgca | atgaggagga | tgcagcagaa | 1200 |
| ctggtagcct | tagcacaggc | tgtgaatgct | cgagccctgc | cagcagtgca | gcaaaataac | 1260 |
| ctggacgagg | acctcatccg | gaagctggca | tatgtggctg | ctggggatct | ggcacccata | 1320 |
| aacgccttca | ttgggggcct | ggctgcccag | gaagtcatga | aggcctgctc | cgggaagttc | 1380 |
| atgcccatca | tgcagtggct | atactttgat | gcccttgagt | gtctccctga | ggacaaagag | 1440 |
| gtcctcacag | aggacaagtg | cctccagcgc | cagaaccgtt | atgacgggca | agtggctgtg | 1500 |
| tttggctcag | acctgcaaga | gaagctgggc | aagcagaagt | atttcctggt | gggtgcgggg | 1560 |
| gccattggct | gtgagctgct | caagaacttt | gccatgattg | ggctgggctg | cggggagggt | 1620 |
| ggagaaatca | tcgttacaga | catggacacc | attgagaagt | caaatctgaa | tcgacagttt | 1680 |
| cttttccggc | cctgggatgt | cacgaagtta | aagtctgaca | cggctgctgc | agctgtgcgc | 1740 |
| caaatgaatc | cacatatccg | ggtgacaagc | caccagaacc | gtgtgggtcc | tgacacggag | 1800 |
| cgcatctatg | atgacgattt | tttccaaaac | ctagatggcg | tggccaatgc | cctggacaac | 1860 |
| gtggatgccc | gcatgtacat | ggaccgccgc | tgtgtctact | accggaagcc | actgctggag | 1920 |
| tcaggcacac | tgggcaccaa | aggcaatgtg | caggtggtga | tccccttcct | gacagagtcg | 1980 |
| tacagttcca | gccaggaccc | acctgagaag | tccatcccca | tctgtacccc | gaagaacttc | 2040 |
| cctaatgcca | tcgagcacac | cctgcagtgg | gctcgggatg | agtttgaagg | cctcttcaag | 2100 |
| cagccagcag | aaaatgtcaa | ccagtacctc | acagaccca | agtttgtgga | gcgaacactg | 2160 |
| cggctggcag | gcactcagcc | cttggaggtg | ctggaggctg | tgcagcgcag | cctggtgctg | 2220 |

-continued

```
cagcgaccac agacctgggc tgactgcgtg acctgggcct gccaccactg gcacacccag    2280
tactcgaaca acatccggca gctgctgcac aacttccctc ctgaccagct cacaagctca    2340
ggagcgccgt tctggtctgg gcccaaacgc tgtccacacc cgctcacctt tgatgtcaac    2400
aatcccctgc atctggacta tgtgatggct gctgccaacc tgtttgccca gacctacggg    2460
ctgacaggct ctcaggaccg agctgctgtg ccacattcc tgcagtctgt gcaggtcccc    2520
gaattcaccc ccaagtctgg cgtcaagatc catgtttctg accaggagct gcagagcgcc    2580
aatgcctctg ttgatgacag tcgtctagag gagctcaaag ccactctgcc cagcccagac    2640
aagctccctg gattcaagat gtacccatt gactttgaga aggatgatga cagcaacttt    2700
catatggatt tcatcgtggc tgcatccaac ctccgggcag aaaactatga cattccttct    2760
gcagaccggc acaagagcaa gctgattgca gggaagatca tcccagccat tgccacgacc    2820
acagcagccg tggttggcct tgtgtgtctg gagctgtaca aggttgtgca ggggcaccga    2880
cagcttgact cctacaagaa tggtttcctc aacttggccc tgcctttctt tggtttctct    2940
gaaccccttg ccgcaccacg tcaccagtac tataaccaag agtggacatt gtgggatcgc    3000
tttgaggtac aagggctgca gcctaatggt gaggagatga ccctcaaaca gttcctcgac    3060 tatttaaga cagagcacaa attagagatc accatgctgt cccagggcgt gtccatgctc    3120
tattccttct tcatgccagc tgccaagctc aaggaacggt tggatcagcc gatgacagag    3180
attgtgagcc gtgtgtcgaa gcgaaagctg ggccgccacg tgcgggcgct ggtgcttgag    3240
ctgtgctgta acgacgagag cggcgaggat gtcgaggttc cctatgtccg atacaccatc    3300
cgctgacccc gtctgctcct ctaggctggc cccttgtcca ccctctcca cacccccttcc    3360 agcccagggt tccatttgg cttctggcag tggcccaact agccaagtct ggtgttccct    3420
catcatcccc ctacctgaac ccctcttgcc actgccttct accttgtttg aaacctgaat    3480
cctaataaag aattaataac tccc                                            3504
```

<210> SEQ ID NO 2
<211> LENGTH: 1058
<212> TYPE: PRT
<213> ORGANISM: Homo sapiens
<220> FEATURE:
<221> NAME/KEY: MISC_FEATURE
<223> OTHER INFORMATION: GenBank Accession No.: NP_003325

<400> SEQUENCE: 2

```
Met Ser Ser Ser Pro Leu Ser Lys Lys Arg Val Ser Gly Pro Asp
1               5                   10                  15

Pro Lys Pro Gly Ser Asn Cys Ser Pro Ala Gln Ser Val Leu Ser Glu
            20                  25                  30

Val Pro Ser Val Pro Thr Asn Gly Met Ala Lys Asn Gly Ser Glu Ala
        35                  40                  45

Asp Ile Asp Glu Gly Leu Tyr Ser Arg Gln Leu Tyr Val Leu Gly His
    50                  55                  60

Glu Ala Met Lys Arg Leu Gln Thr Ser Ser Val Leu Val Ser Gly Leu
65                  70                  75                  80

Arg Gly Leu Gly Val Glu Ile Ala Lys Asn Ile Ile Leu Gly Gly Val
                85                  90                  95

Lys Ala Val Thr Leu His Asp Gln Gly Thr Ala Gln Trp Ala Asp Leu
            100                 105                 110

Ser Ser Gln Phe Tyr Leu Arg Glu Glu Asp Ile Gly Lys Asn Arg Ala
        115                 120                 125
```

```
Glu Val Ser Gln Pro Arg Leu Ala Glu Leu Asn Ser Tyr Val Pro Val
    130                 135                 140

Thr Ala Tyr Thr Gly Pro Leu Val Glu Asp Phe Leu Ser Gly Phe Gln
145                 150                 155                 160

Val Val Val Leu Thr Asn Thr Pro Leu Glu Asp Gln Leu Arg Val Gly
                165                 170                 175

Glu Phe Cys His Asn Arg Gly Ile Lys Leu Val Val Ala Asp Thr Arg
            180                 185                 190

Gly Leu Phe Gly Gln Leu Phe Cys Asp Phe Gly Glu Glu Met Ile Leu
        195                 200                 205

Thr Asp Ser Asn Gly Glu Gln Pro Leu Ser Ala Met Val Ser Met Val
    210                 215                 220

Thr Lys Asp Asn Pro Gly Val Val Thr Cys Leu Asp Glu Ala Arg His
225                 230                 235                 240

Gly Phe Glu Ser Gly Asp Phe Val Ser Phe Ser Glu Val Gln Gly Met
                245                 250                 255

Val Glu Leu Asn Gly Asn Gln Pro Met Glu Ile Lys Val Leu Gly Pro
            260                 265                 270

Tyr Thr Phe Ser Ile Cys Asp Thr Ser Asn Phe Ser Asp Tyr Ile Arg
        275                 280                 285

Gly Gly Ile Val Ser Gln Val Lys Val Pro Lys Ile Ser Phe Lys
    290                 295                 300

Ser Leu Val Ala Ser Leu Ala Glu Pro Asp Phe Val Val Thr Asp Phe
305                 310                 315                 320

Ala Lys Phe Ser Arg Pro Ala Gln Leu His Ile Gly Phe Gln Ala Leu
                325                 330                 335

His Gln Phe Cys Ala Gln His Gly Arg Pro Pro Arg Pro Arg Asn Glu
            340                 345                 350

Glu Asp Ala Ala Glu Leu Val Ala Leu Ala Gln Ala Val Asn Ala Arg
        355                 360                 365

Ala Leu Pro Ala Val Gln Gln Asn Asn Leu Asp Glu Asp Leu Ile Arg
    370                 375                 380

Lys Leu Ala Tyr Val Ala Ala Gly Asp Leu Ala Pro Ile Asn Ala Phe
385                 390                 395                 400

Ile Gly Gly Leu Ala Ala Gln Glu Val Met Lys Ala Cys Ser Gly Lys
                405                 410                 415

Phe Met Pro Ile Met Gln Trp Leu Tyr Phe Asp Ala Leu Glu Cys Leu
            420                 425                 430

Pro Glu Asp Lys Glu Val Leu Thr Glu Asp Lys Cys Leu Gln Arg Gln
        435                 440                 445

Asn Arg Tyr Asp Gly Gln Val Ala Phe Gly Ser Asp Leu Gln Glu
    450                 455                 460

Lys Leu Gly Lys Gln Lys Tyr Phe Leu Val Gly Ala Gly Ala Ile Gly
465                 470                 475                 480

Cys Glu Leu Leu Lys Asn Phe Ala Met Ile Gly Leu Gly Cys Gly Glu
                485                 490                 495

Gly Gly Glu Ile Ile Val Thr Asp Met Asp Thr Ile Glu Lys Ser Asn
            500                 505                 510

Leu Asn Arg Gln Phe Leu Phe Arg Pro Trp Asp Val Thr Lys Leu Lys
        515                 520                 525

Ser Asp Thr Ala Ala Ala Ala Val Arg Gln Met Asn Pro His Ile Arg
    530                 535                 540
```

-continued

```
Val Thr Ser His Gln Asn Arg Val Gly Pro Asp Thr Glu Arg Ile Tyr
545                 550                 555                 560

Asp Asp Asp Phe Phe Gln Asn Leu Asp Gly Val Ala Asn Ala Leu Asp
                565                 570                 575

Asn Val Asp Ala Arg Met Tyr Met Asp Arg Arg Cys Val Tyr Tyr Arg
            580                 585                 590

Lys Pro Leu Leu Glu Ser Gly Thr Leu Gly Thr Lys Gly Asn Val Gln
        595                 600                 605

Val Val Ile Pro Phe Leu Thr Glu Ser Tyr Ser Ser Gln Asp Pro
    610                 615                 620

Pro Glu Lys Ser Ile Pro Ile Cys Thr Leu Lys Asn Phe Pro Asn Ala
625                 630                 635                 640

Ile Glu His Thr Leu Gln Trp Ala Arg Asp Glu Phe Glu Gly Leu Phe
                645                 650                 655

Lys Gln Pro Ala Glu Asn Val Asn Gln Tyr Leu Thr Asp Pro Lys Phe
            660                 665                 670

Val Glu Arg Thr Leu Arg Leu Ala Gly Thr Gln Pro Leu Glu Val Leu
        675                 680                 685

Glu Ala Val Gln Arg Ser Leu Val Leu Gln Arg Pro Gln Thr Trp Ala
    690                 695                 700

Asp Cys Val Thr Trp Ala Cys His His Trp His Thr Gln Tyr Ser Asn
705                 710                 715                 720

Asn Ile Arg Gln Leu Leu His Asn Phe Pro Pro Asp Gln Leu Thr Ser
                725                 730                 735

Ser Gly Ala Pro Phe Trp Ser Gly Pro Lys Arg Cys Pro His Pro Leu
            740                 745                 750

Thr Phe Asp Val Asn Asn Pro Leu His Leu Asp Tyr Val Met Ala Ala
        755                 760                 765

Ala Asn Leu Phe Ala Gln Thr Tyr Gly Leu Thr Gly Ser Gln Asp Arg
    770                 775                 780

Ala Ala Val Ala Thr Phe Leu Gln Ser Val Gln Val Pro Glu Phe Thr
785                 790                 795                 800

Pro Lys Ser Gly Val Lys Ile His Val Ser Asp Gln Glu Leu Gln Ser
                805                 810                 815

Ala Asn Ala Ser Val Asp Asp Ser Arg Leu Glu Glu Leu Lys Ala Thr
            820                 825                 830

Leu Pro Ser Pro Asp Lys Leu Pro Gly Phe Lys Met Tyr Pro Ile Asp
        835                 840                 845

Phe Glu Lys Asp Asp Asp Ser Asn Phe His Met Asp Phe Ile Val Ala
    850                 855                 860

Ala Ser Asn Leu Arg Ala Glu Asn Tyr Asp Ile Pro Ser Ala Asp Arg
865                 870                 875                 880

His Lys Ser Lys Leu Ile Ala Gly Lys Ile Pro Ala Ile Ala Thr
                885                 890                 895

Thr Thr Ala Ala Val Val Gly Leu Val Cys Leu Glu Leu Tyr Lys Val
            900                 905                 910

Val Gln Gly His Arg Gln Leu Asp Ser Tyr Lys Asn Gly Phe Leu Asn
        915                 920                 925

Leu Ala Leu Pro Phe Phe Gly Phe Ser Glu Pro Leu Ala Ala Pro Arg
    930                 935                 940

His Gln Tyr Tyr Asn Gln Glu Trp Thr Leu Trp Asp Arg Phe Glu Val
945                 950                 955                 960

Gln Gly Leu Gln Pro Asn Gly Glu Glu Met Thr Leu Lys Gln Phe Leu
```

```
                965               970               975
Asp Tyr Phe Lys Thr Glu His Lys Leu Glu Ile Thr Met Leu Ser Gln
        980               985               990
Gly Val Ser Met Leu Tyr Ser Phe Phe Met Pro Ala Ala Lys Leu Lys
        995               1000              1005
Glu Arg Leu Asp Gln Pro Met Thr Glu Ile Val Ser Arg Val Ser
    1010              1015              1020
Lys Arg Lys Leu Gly Arg His Val Arg Ala Leu Val Leu Glu Leu
    1025              1030              1035
Cys Cys Asn Asp Glu Ser Gly Glu Asp Val Glu Val Pro Tyr Val
    1040              1045              1050
Arg Tyr Thr Ile Arg
    1055

<210> SEQ ID NO 3
<211> LENGTH: 3159
<212> TYPE: DNA
<213> ORGANISM: Homo sapiens
<220> FEATURE:
<221> NAME/KEY: misc_feature
<223> OTHER INFORMATION: GenBank Accession No.: AB014773

<400> SEQUENCE: 3
atggaaggat ccgagcctgt ggccgcccat caggggaag aggcgtcctg ttcttcctgg      60
gggactggca gcacaaataa aaatttgccc attatgtcaa cagcatctgt ggaaatcgat     120
gatgcattgt atagtcgaca gaggtacgtt cttggagaca cagcaatgca gaagatggcc     180
aagtcccatg ttttcttaag tgggatgggt ggtcttggtt tggaaattgc aaagaatctt     240
gttcttgcag ggattaaggc agttacaatt catgatacag aaaaatgcca agcatgggat     300
ctaggaacca acttctttct cagtgaagat gatgttgtta ataagagaaa cagggctgaa     360
gctgtactta aacatattgc agaactaaat ccatacgttc atgtcacatc atcttctgtt     420
cctttcaatg agaccacaga tctctccttt ttagataaat accagtgtgt agtattgact     480
gagatgaaac ttccattgca gaagaagatc aatgactttt gccgttctca gtgccctcca     540
attaagttta tcagtgcaga tgtacatgga atttggtcaa ggttattttg tgatttcggt     600
gatgaatttg aagttttaga tacaacagga gaagaaccaa agaaattttt catttcaaac     660
ataacgcaag caaatcctgg cattgttact tgccttgaaa atcatcctca caaactggag     720
acaggacaat tcctaacatt tcgagaaatt aatggaatga caggtttaaa tggatctata     780
caacaaataa cggtgatatc gccattttct tttagtattg gtgacaccac agaactggaa     840
ccatatttac atggaggcat agctgtccaa gttaagactc ctaaaacagt ttttttttgaa     900 tcactggaga ggcagttaaa acatccaaag tgccttattg tggattttag caaccctgag     960
gcacctttag agattcacac agctatgctt gccttggacc agtttcagga gaaatacagt    1020
cgcaagccaa atgttggatg ccaacaagat tcagaagaac tgttgaaact agcaacatct    1080
ataagtgaaa ccttggaaga gaagcctgat gtaaatgctg acattgtgca ttggctctct    1140
tggactgccc aaggcttttt atctccactt gctgcagcag taggaggtgt tgccagccaa    1200
gaagtattga agctgtaac aggaaaaatt tctcctttgt gccagtggtt atatcttgaa    1260
gcagcagata ttgttgaatc actaggcaaa cctgaatgtg aagaatttct cccacgagga    1320
gatagatatg atgccttaag agcttgcatt ggagacactt tgtgtcagaa actgcaaaat    1380
ttaaacatct tcttagtagg gtgtggagcc ataggctgtg aaatgttgaa aaattttgct    1440
```

-continued

```
ttacttggtg ttggcacaag caaagagaaa ggaatgatta cagttacaga tcctgacttg   1500
atagagaaat ccaacttaaa tagacagttc ctatttcgtc ctcatcacat acagaaacct   1560
aaaagctaca ctgctgctga tgctactctg aaaataaatt ctcaaataaa gatagatgca   1620
cacctgaaca aagtatgtcc aaccactgag accatttaca atgatgagtt ctatactaaa   1680
caagatgtaa ttattacagc attagataat gtggaagcca ggagatacgt agacagtcgt   1740
tgcttagcaa atctaaggcc tcttttagat tctggaacaa tgggcactaa gggacacact   1800
gaagttattg taccgcattt gactgagtct tacaatagtc atcgggatcc cccagaagag   1860
gaaataccat tttgtactct aaaatccttt ccagctgcta ttgaacatac catacagtgg   1920
gcaagagata agtttgaaag ttcctttttcc cacaaacctt cattgtttaa caaattttgg   1980
caaacctatt catctgcaga agaagtctta cagaagatac agagtggaca cagtttagaa   2040
ggctgttttc aagttataaa gttacttagc agaagaccta gaaattggtc ccagtgtgta   2100
gaattagcaa gattaaagtt tgaaaaatat tttaaccata aggctcttca gcttcttcac   2160
tgtttccctc tggacatacg attaaaagat ggcagtttat tttggcagtc accaaagagg   2220
ccaccctctc aataaaaatt tgatttaaat gagcctttgc acctcagttt ccttcagaat   2280
gctgcaaaac tatatgctac agtatattgt attccatttg cagaagagga cttatcagca   2340
gatgccctct tgaatattct ttcagaagta aagattcagg aattcaagcc ttccaataag   2400
gttgttcaaa cagatgaaac tgcaaggaaa ccagaccatg ttcctattag cagtgaagat   2460
gagaggaatg caattttcca actagaaaag gctattttat ctaatgaagc caccaaaagt   2520
gaccttcaga tggcagtgct ttcatttgaa aaagatgatg atcataatgg acacatagat   2580
ttcatcacag ctgcatcaaa tcttcgtgcc aaaatgtaca gcattgaacc agctgaccgt   2640
ttcaaaacaa agcgcatagc tggtaaaatt atacctgcta tagcaacaac cactgctaca   2700
gtttctggct tggttgcctt ggagatgatc aaagtaactg gtggctatcc atttgaagtt   2760
tacaaaaatt gttttcttaa cttagccatt ccaattgtag tatttacaga gacaactgaa   2820
gtaaggaaaa ctaaaatcag aaatggaata tcatttacaa tttgggatcg atggaccgta   2880
catggaaaag aagatttcac cctcttggat ttcataaatg cagtcaaaga gaagtatgga   2940
attgagccaa caatggtggt acagggagtc aaaatgcttt atgttcctgt aatgcctggt   3000
catgcaaaaa gattgaagtt aacaatgcat aaacttgtaa aacctactac tgaaaagaaa   3060
tatgtggatc ttactgtgtc atttgctcca gacattgatg gagatgaaga tttgccggga   3120
cctccagtaa gatactactt cagtcatgac actgattaa                          3159
```

<210> SEQ ID NO 4
<211> LENGTH: 1052
<212> TYPE: PRT
<213> ORGANISM: Homo sapiens
<220> FEATURE:
<221> NAME/KEY: MISC_FEATURE
<223> OTHER INFORMATION: GenBank Accession No.: BAB19785

<400> SEQUENCE: 4

```
Met Glu Gly Ser Glu Pro Val Ala Ala His Gln Gly Glu Glu Ala Ser
1               5                   10                  15

Cys Ser Ser Trp Gly Thr Gly Ser Thr Asn Lys Asn Leu Pro Ile Met
            20                  25                  30

Ser Thr Ala Ser Val Glu Ile Asp Asp Ala Leu Tyr Ser Arg Gln Arg
        35                  40                  45

Tyr Val Leu Gly Asp Thr Ala Met Gln Lys Met Ala Lys Ser His Val
```

-continued

```
              50                  55                  60
Phe Leu Ser Gly Met Gly Gly Leu Gly Leu Glu Ile Ala Lys Asn Leu
 65                  70                  75                  80
Val Leu Ala Gly Ile Lys Ala Val Thr Ile His Asp Thr Glu Lys Cys
                 85                  90                  95
Gln Ala Trp Asp Leu Gly Thr Asn Phe Phe Leu Ser Glu Asp Asp Val
                100                 105                 110
Val Asn Lys Arg Asn Arg Ala Glu Ala Val Leu Lys His Ile Ala Glu
                115                 120                 125
Leu Asn Pro Tyr Val His Val Thr Ser Ser Val Pro Phe Asn Glu
130                 135                 140
Thr Thr Asp Leu Ser Phe Leu Asp Lys Tyr Gln Cys Val Val Leu Thr
145                 150                 155                 160
Glu Met Lys Leu Pro Leu Gln Lys Lys Ile Asn Asp Phe Cys Arg Ser
                165                 170                 175
Gln Cys Pro Pro Ile Lys Phe Ile Ser Ala Asp Val His Gly Ile Trp
                180                 185                 190
Ser Arg Leu Phe Cys Asp Phe Gly Asp Glu Phe Glu Val Leu Asp Thr
                195                 200                 205
Thr Gly Glu Glu Pro Lys Glu Ile Phe Ile Ser Asn Ile Thr Gln Ala
210                 215                 220
Asn Pro Gly Ile Val Thr Cys Leu Glu Asn His Pro His Lys Leu Glu
225                 230                 235                 240
Thr Gly Gln Phe Leu Thr Phe Arg Glu Ile Asn Gly Met Thr Gly Leu
                245                 250                 255
Asn Gly Ser Ile Gln Gln Ile Thr Val Ile Ser Pro Phe Ser Phe Ser
                260                 265                 270
Ile Gly Asp Thr Thr Glu Leu Glu Pro Tyr Leu His Gly Gly Ile Ala
                275                 280                 285
Val Gln Val Lys Thr Pro Lys Thr Val Phe Phe Glu Ser Leu Glu Arg
                290                 295                 300
Gln Leu Lys His Pro Lys Cys Leu Ile Val Asp Phe Ser Asn Pro Glu
305                 310                 315                 320
Ala Pro Leu Glu Ile His Thr Ala Met Leu Ala Leu Asp Gln Phe Gln
                325                 330                 335
Glu Lys Tyr Ser Arg Lys Pro Asn Val Gly Cys Gln Gln Asp Ser Glu
                340                 345                 350
Glu Leu Leu Lys Leu Ala Thr Ser Ile Ser Glu Thr Leu Glu Glu Lys
                355                 360                 365
Pro Asp Val Asn Ala Asp Ile Val His Trp Leu Ser Trp Thr Ala Gln
370                 375                 380
Gly Phe Leu Ser Pro Leu Ala Ala Val Gly Val Ala Ser Gln
385                 390                 395                 400
Glu Val Leu Lys Ala Val Thr Gly Lys Phe Ser Pro Leu Cys Gln Trp
                405                 410                 415
Leu Tyr Leu Glu Ala Ala Asp Ile Val Glu Ser Leu Gly Lys Pro Glu
                420                 425                 430
Cys Glu Glu Phe Leu Pro Arg Gly Asp Arg Tyr Asp Ala Leu Arg Ala
                435                 440                 445
Cys Ile Gly Asp Thr Leu Cys Gln Lys Leu Gln Asn Leu Asn Ile Phe
                450                 455                 460
Leu Val Gly Cys Gly Ala Ile Gly Cys Glu Met Leu Lys Asn Phe Ala
465                 470                 475                 480
```

-continued

```
Leu Leu Gly Val Gly Thr Ser Lys Glu Lys Gly Met Ile Thr Val Thr
                485                 490                 495
Asp Pro Asp Leu Ile Glu Lys Ser Asn Leu Asn Arg Gln Phe Leu Phe
            500                 505                 510
Arg Pro His His Ile Gln Lys Pro Lys Ser Tyr Thr Ala Ala Asp Ala
        515                 520                 525
Thr Leu Lys Ile Asn Ser Gln Ile Lys Ile Asp Ala His Leu Asn Lys
    530                 535                 540
Val Cys Pro Thr Thr Glu Thr Ile Tyr Asn Asp Glu Phe Tyr Thr Lys
545                 550                 555                 560
Gln Asp Val Ile Ile Thr Ala Leu Asp Asn Val Glu Ala Arg Arg Tyr
                565                 570                 575
Val Asp Ser Arg Cys Leu Ala Asn Leu Arg Pro Leu Leu Asp Ser Gly
            580                 585                 590
Thr Met Gly Thr Lys Gly His Thr Glu Val Ile Val Pro His Leu Thr
        595                 600                 605
Glu Ser Tyr Asn Ser His Arg Asp Pro Pro Glu Glu Ile Pro Phe
    610                 615                 620
Cys Thr Leu Lys Ser Phe Pro Ala Ala Ile Glu His Thr Ile Gln Trp
625                 630                 635                 640
Ala Arg Asp Lys Phe Glu Ser Ser Phe Ser His Lys Pro Ser Leu Phe
                645                 650                 655
Asn Lys Phe Trp Gln Thr Tyr Ser Ser Ala Glu Glu Val Leu Gln Lys
            660                 665                 670
Ile Gln Ser Gly His Ser Leu Glu Gly Cys Phe Gln Val Ile Lys Leu
        675                 680                 685
Leu Ser Arg Arg Pro Arg Asn Trp Ser Gln Cys Val Glu Leu Ala Arg
    690                 695                 700
Leu Lys Phe Glu Lys Tyr Phe Asn His Lys Ala Leu Gln Leu Leu His
705                 710                 715                 720
Cys Phe Pro Leu Asp Ile Arg Leu Lys Asp Gly Ser Leu Phe Trp Gln
                725                 730                 735
Ser Pro Lys Arg Pro Pro Ser Pro Ile Lys Phe Asp Leu Asn Glu Pro
            740                 745                 750
Leu His Leu Ser Phe Leu Gln Asn Ala Ala Lys Leu Tyr Ala Thr Val
        755                 760                 765
Tyr Cys Ile Pro Phe Ala Glu Glu Asp Leu Ser Ala Asp Ala Leu Leu
    770                 775                 780
Asn Ile Leu Ser Glu Val Lys Ile Gln Glu Phe Lys Pro Ser Asn Lys
785                 790                 795                 800
Val Val Gln Thr Asp Glu Thr Ala Arg Lys Pro Asp His Val Pro Ile
                805                 810                 815
Ser Ser Glu Asp Glu Arg Asn Ala Ile Phe Gln Leu Glu Lys Ala Ile
            820                 825                 830
Leu Ser Asn Glu Ala Thr Lys Ser Asp Leu Gln Met Ala Val Leu Ser
        835                 840                 845
Phe Glu Lys Asp Asp His Asn Gly His Ile Asp Phe Ile Thr Ala
    850                 855                 860
Ala Ser Asn Leu Arg Ala Lys Met Tyr Ser Ile Glu Pro Ala Asp Arg
865                 870                 875                 880
Phe Lys Thr Lys Arg Ile Ala Gly Lys Ile Ile Pro Ala Ile Ala Thr
                885                 890                 895
```

-continued

```
Thr Thr Ala Thr Val Ser Gly Leu Val Ala Leu Glu Met Ile Lys Val
            900                 905                 910
Thr Gly Gly Tyr Pro Phe Glu Val Tyr Lys Asn Cys Phe Leu Asn Leu
        915                 920                 925
Ala Ile Pro Ile Val Val Phe Thr Glu Thr Thr Glu Val Arg Lys Thr
    930                 935                 940
Lys Ile Arg Asn Gly Ile Ser Phe Thr Ile Trp Asp Arg Trp Thr Val
945                 950                 955                 960
His Gly Lys Glu Asp Phe Thr Leu Leu Asp Phe Ile Asn Ala Val Lys
                965                 970                 975
Glu Lys Tyr Gly Ile Glu Pro Thr Met Val Val Gln Gly Val Lys Met
            980                 985                 990
Leu Tyr Val Pro Val Met Pro Gly His Ala Lys Arg Leu Lys Leu Thr
        995                 1000                1005
Met His Lys Leu Val Lys Pro Thr Thr Glu Lys Lys Tyr Val Asp
    1010                1015                1020
Leu Thr Val Ser Phe Ala Pro Asp Ile Asp Gly Asp Glu Asp Leu
    1025                1030                1035
Pro Gly Pro Pro Val Arg Tyr Tyr Phe Ser His Asp Thr Asp
    1040                1045                1050
```

<210> SEQ ID NO 5
<211> LENGTH: 2720
<212> TYPE: DNA
<213> ORGANISM: Homo sapiens
<220> FEATURE:
<221> NAME/KEY: misc_feature
<223> OTHER INFORMATION: GenBank Accession No.: NM_024818

<400> SEQUENCE: 5

```
ttgatgaggg ggagcgatgt ctgcgacgca ccggaagcgg ctccgaggaa ggcctgtggg     60
agtctcggag acgtgtctgt ctgtgaggcg ctgggtgcac gtccccaggg ctctgggcta    120
ggaaggcagc ggcgaggtgc ctccccacgt accctcgcg ggcccagccg agcaacgtgg    180
ggcgaaggcg gcggcgaagg cccgggctgg gagcgttggc ggccggagtc ccagccatgg    240
cggagtctgt ggagcgcctg cagcagcggg tccaggagct ggagcgggaa cttgcccagg    300
agaggagtct gcaggtcccg aggagcggcg acggaggggg cggccgggtc cgcatcgaga    360
agatgagctc agaggtggtg gattcgaatc cctacagccg cttgatggca ttgaaacgaa    420
tgggaattgt aagcgactat gagaaaatcc gtacctttgc cgtagcaata gtaggtgttg    480
gtggagtagg tagtgtgact gctgaaatgc tgacaagatg tggcattggt aagttgctac    540
tctttgatta tgacaaggtg gaactagcca atatgaatag acttttcttc caacctcatc    600
aagcaggatt aagtaaagtt caagcagcag aacatactct gaggaacatt aatcctgatg    660
ttcttttttga agtacacaac tataatataa ccacagtgga aaactttcaa catttcatgg    720
atagaataag taatggtggg ttagaagaag gaaaacctgt tgatctagtt cttagctgtg    780
tggacaattt tgaagctcga atgacaataa atacagcttg taatgaactt ggacaaacat    840
ggatggaatc tgggggtcagt gaaaatgcag tttcagggca tatacagctt ataattcctg    900
gagaatctgc ttgttttgcg tgtgctccac cacttgtagt tgctgcaaat attgatgaaa    960
agactctgaa acgagaaggt gtttgtgcag ccagtcttcc taccactatg ggtgtggttg   1020
ctgggatctt agtacaaaac gtgttaaagt ttctgttaaa ttttggtact gttagttttt   1080
accttggata caatgcaatg caggatttttt ttcctactat gtccatgaag ccaaatcctc   1140
```

-continued

```
agtgtgatga cagaaattgc aggaagcagc aggaggaata taagaaaaag gtagcagcac    1200
tgcctaaaca agaggttata caagaagagg aagagataat ccatgaagat aatgaatggg    1260
gtattgagct ggtatctgag gtttcagaag aggaactgaa aaattttca ggtccagttc     1320 cagacttacc tgaaggaatt acagtggcat acacaattcc aaaaaagcaa gaagattctg    1380
tcactgagtt aacagtggaa gattctggtg aaagcttgga agacctcatg gccaaaatga    1440
agaatatgta gataatggac tgggatatat tgtatttctc atgttaaagc ctcttccctt    1500
gaaattaaaa aaaattttta actgataaaa cttagggcaa cattaattaa tgtatattct    1560
tacctgaatt gttatacttt ttgaaaatcc tgtgacttgc ctgtttctcc ccgctccaac    1620
gaaatcatta actctcctaa aatgtgtttc attctagtaa gaaaacctca aggatattg     1680 taggatataa atcttacttg aaaacatagc tgttgaaatg ttttggcctt ttggagtggg    1740
ggaaggacaa atctgatcct gtaatctttt tctttccagt aatcccttgt gtctgttgca    1800
tgaggacatg gacaataaag tagtatatga tcctcagata cagggagaag gacaaggcat    1860
acagcttatt gattagagct ggcaagcatc tgctcattat gtttggaatt gctttctata    1920
agaaaattgc ccactactac taacttgatc aacaatgaat tcaaaatagt taacctatga    1980
aataacatcc tctcaaatgt ttgctgatga agtacaagtt gaaatgtagt tattggaaaa    2040
gtctgtaacc tgtggatcat atatattcaa agtgagacaa aggcaaataa aaagcagcta    2100
ttttcatgaa tagacaaagt tgatttcagg aagtataaat tatattctgc accgaacaag    2160
gaacagaaat tattgcatct gtggaacata tatctggagt tactatactt tactgaagag    2220
caaggcataa atttagacta aaatccatcc agattacact cattctttag gctactcctg    2280
gatacttcat ttaaatttga ttttcgaggt agtgagatgt cggcaaggtt tgtcctgtat    2340
attaggaata aaggaaaagt tctaaactgc ctctgcaatg acttgtagtc agtggaagag    2400
tatcactttc ccctgatcat gaccactaaa ctgtaaattg atataaatta gttttctctc    2460
gagttacacc caagtaatga agacttaaga gaaccttggt tgaaataaat ttccaatagt    2520
ttggagactc ataaatacca tgcaggtgta accactgcca ataggctgtt tctatgctta    2580
tttcctattt tgattttac tttgaagata ggaatatcta aattatatct ctagggagaa     2640
aatgttgtaa aaaattaaaa gtacatccct gattgtaaaa taaagttcaa aaaactgatt    2700
tcaaaaaaaa aaaaaaaaa                                                 2720
```

<210> SEQ ID NO 6
<211> LENGTH: 404
<212> TYPE: PRT
<213> ORGANISM: Homo sapiens
<220> FEATURE:
<221> NAME/KEY: MISC_FEATURE
<223> OTHER INFORMATION: GenBank Accession No.: NP_079094

<400> SEQUENCE: 6

```
Met Ala Glu Ser Val Glu Arg Leu Gln Gln Arg Val Gln Glu Leu Glu
1               5                   10                  15

Arg Glu Leu Ala Gln Glu Arg Ser Leu Gln Val Pro Arg Ser Gly Asp
            20                  25                  30

Gly Gly Gly Gly Arg Val Arg Ile Glu Lys Met Ser Ser Glu Val Val
        35                  40                  45

Asp Ser Asn Pro Tyr Ser Arg Leu Met Ala Leu Lys Arg Met Gly Ile
    50                  55                  60

Val Ser Asp Tyr Glu Lys Ile Arg Thr Phe Ala Val Ala Ile Val Gly
65                  70                  75                  80
```

Val Gly Gly Val Gly Ser Val Thr Ala Glu Met Leu Thr Arg Cys Gly
                85                  90                  95
Ile Gly Lys Leu Leu Leu Phe Asp Tyr Asp Lys Val Glu Leu Ala Asn
            100                 105                 110
Met Asn Arg Leu Phe Phe Gln Pro His Gln Ala Gly Leu Ser Lys Val
        115                 120                 125
Gln Ala Ala Glu His Thr Leu Arg Asn Ile Asn Pro Asp Val Leu Phe
    130                 135                 140
Glu Val His Asn Tyr Asn Ile Thr Thr Val Glu Asn Phe Gln His Phe
145                 150                 155                 160
Met Asp Arg Ile Ser Asn Gly Gly Leu Glu Glu Gly Lys Pro Val Asp
                165                 170                 175
Leu Val Leu Ser Cys Val Asp Asn Phe Glu Ala Arg Met Thr Ile Asn
            180                 185                 190
Thr Ala Cys Asn Glu Leu Gly Gln Thr Trp Met Glu Ser Gly Val Ser
        195                 200                 205
Glu Asn Ala Val Ser Gly His Ile Gln Leu Ile Ile Pro Gly Glu Ser
    210                 215                 220
Ala Cys Phe Ala Cys Ala Pro Pro Leu Val Val Ala Ala Asn Ile Asp
225                 230                 235                 240
Glu Lys Thr Leu Lys Arg Glu Gly Val Cys Ala Ala Ser Leu Pro Thr
                245                 250                 255
Thr Met Gly Val Val Ala Gly Ile Leu Val Gln Asn Val Leu Lys Phe
            260                 265                 270
Leu Leu Asn Phe Gly Thr Val Ser Phe Tyr Leu Gly Tyr Asn Ala Met
        275                 280                 285
Gln Asp Phe Phe Pro Thr Met Ser Met Lys Pro Asn Pro Gln Cys Asp
    290                 295                 300
Asp Arg Asn Cys Arg Lys Gln Gln Glu Glu Tyr Lys Lys Lys Val Ala
305                 310                 315                 320
Ala Leu Pro Lys Gln Glu Val Ile Gln Glu Glu Glu Ile Ile His
                325                 330                 335
Glu Asp Asn Glu Trp Gly Ile Glu Leu Val Ser Glu Val Ser Glu Glu
            340                 345                 350
Glu Leu Lys Asn Phe Ser Gly Pro Val Pro Asp Leu Pro Glu Gly Ile
        355                 360                 365
Thr Val Ala Tyr Thr Ile Pro Lys Lys Gln Glu Asp Ser Val Thr Glu
    370                 375                 380
Leu Thr Val Glu Asp Ser Gly Glu Ser Leu Glu Asp Leu Met Ala Lys
385                 390                 395                 400
Met Lys Asn Met

<210> SEQ ID NO 7
<211> LENGTH: 2136
<212> TYPE: DNA
<213> ORGANISM: Homo sapiens
<220> FEATURE:
<221> NAME/KEY: misc_feature
<223> OTHER INFORMATION: GenBank Accession No.: NM_003968

<400> SEQUENCE: 7
gggaagaggc ggagaacaat atggcggatg cgaggagcc ggagaagaaa agaaggagaa      60
tagaggagct gctggctgag aaaatggctg ttgatggtgg gtgtggggac actggagact     120
gggaaggtcg ctggaaccat gtaaagaagt tcctcgagcg atctggaccc ttcacacacc     180

```
ctgatttcga accgagcact gaatctctcc agttcttgtt agatacatgt aaagttctag      240
tcattggagc tggcggctta ggatgtgagc tcctgaaaaa tctggccttg tctggtttta      300
gacagattca tgttatagat atggacacta tagatgtttc aatctaaat aggcagtttt       360 tatttaggcc taaagatatt ggaagaccta aggctgaagt tgctgcagaa tttctaaatg      420
acagagttcc taattgcaat gtagttccac atttcaacaa gattcaagat tttaacgaca      480 cttctatcg acaatttcat attattgtat gtggactgga ctctatcatc gccagaagat       540
ggataaatgg catgctgata tctcttctaa attatgaaga tggtgtctta gatccaagct      600
ccattgtccc tttgatagat gggggacag aaggttttaa aggaaatgcc cgggtgattc       660
tgcctggaat gactgcttgt atcgaatgca cgctggaact ttatccacca caggttaatt      720
ttcccatgtg caccattgca tctatgccca ggctaccaga acactgtatt gagtatgtaa      780
ggatgttgca gtggcctaag gagcagcctt tggagaagg ggttccatta gatggagatg       840
atcctgaaca tatacaatgg attttccaaa aatccctaga gagagcatca aatataata       900 ttaggggtgt tacgtatagg ctcactcaag gggtagtaaa aagaatcatt cctgcagtag      960
cttccacaaa tgcagtcatt gcagctgtgt gtgccactga ggttttaaa atagccacaa       1020 gtgcatacat tcccttgaat aattacttgg tgtttaatga tgtagatggg ctgtatacat      1080
acacatttga agcagaaaga aaggaaaact gcccagcttg tagccagctt cctcaaaata      1140
ttcagttttc tccatcagct aaactacagg aggttttgga ttatctaacc aatagtgctt      1200
ctctgcaaat gaaatctcca gccatcacag ccaccctaga gggaaaaat agaacactt       1260 acttacagtc ggtaacctct attgaagaac gaacaaggcc aaatctctcc aaaacattga      1320
aagaattggg gcttgttgat ggacaagaac tggcggttgc tgatgtcacc accccacaga     1380
ctgtactatt caaacttcat tttacttctt aaggaaaatc tccacataat agaaaactca     1440
tggaaataat atactttgtg gatgctaaga agttgaatcg atgtcatttt tagcaatagt     1500
gttgccacga tttgtctttt tttatataat gaaccactct tttttaactt tgtaaccttc     1560
ccttgaagac agaattttgg tgttggtgct tgtaagcatt tcattaata atatgagaaa      1620 tgatacctgg agagagagat tatgagcaaa tgtattgctt cttttagagg aggaagcata     1680
caacctcttt tgtgtgaatt tgttattat ggtcaaagaa tgcattccta agttttcatt      1740
tgagtaccca atacacaaa aggtgtccct ttaaggaaaa taaagaatta agttttaaat      1800
aacattacat tttacaatct gacatctgga gtatattgaa cataggctat ttcttgatat     1860
aacactcatt taattgtggc catccaaatg aatattattg cagaatttat cttgttcata     1920
atgatttgta aatggtgtta tagctgaata cctgtgcatg aaaatgggca atattttcat     1980
ctgtttactt gtagtgccat agaggccaat atgcacaata ttaactaatg ccaagacatg     2040
gctgtttaaa aaatttaatg ttcaaacagt tatcactgat gcttttgcac tatttattaa     2100
taaaatcata tattgtgtaa aaaaaaaaaa aaaaaa                               2136
```

<210> SEQ ID NO 8
<211> LENGTH: 463
<212> TYPE: PRT
<213> ORGANISM: Homo sapiens
<220> FEATURE:
<221> NAME/KEY: MISC_FEATURE
<223> OTHER INFORMATION: GenBank Accession No.: NP_003959

<400> SEQUENCE: 8

Met Ala Asp Gly Glu Glu Pro Glu Lys Lys Arg Arg Arg Ile Glu Glu

```
  1               5                   10                  15
Leu Leu Ala Glu Lys Met Ala Val Asp Gly Gly Cys Gly Asp Thr Gly
                 20                  25                  30

Asp Trp Glu Gly Arg Trp Asn His Val Lys Lys Phe Leu Glu Arg Ser
                 35                  40                  45

Gly Pro Phe Thr His Pro Asp Phe Glu Pro Ser Thr Glu Ser Leu Gln
                 50                  55                  60

Phe Leu Leu Asp Thr Cys Lys Val Leu Val Ile Gly Ala Gly Gly Leu
65                   70                  75                  80

Gly Cys Glu Leu Leu Lys Asn Leu Ala Leu Ser Gly Phe Arg Gln Ile
                 85                  90                  95

His Val Ile Asp Met Asp Thr Ile Asp Val Ser Asn Leu Asn Arg Gln
                 100                 105                 110

Phe Leu Phe Arg Pro Lys Asp Ile Gly Arg Pro Lys Ala Glu Val Ala
                 115                 120                 125

Ala Glu Phe Leu Asn Asp Arg Val Pro Asn Cys Asn Val Val Pro His
                 130                 135                 140

Phe Asn Lys Ile Gln Asp Phe Asn Asp Thr Phe Tyr Arg Gln Phe His
145                  150                 155                 160

Ile Ile Val Cys Gly Leu Asp Ser Ile Ile Ala Arg Arg Trp Ile Asn
                 165                 170                 175

Gly Met Leu Ile Ser Leu Leu Asn Tyr Glu Asp Gly Val Leu Asp Pro
                 180                 185                 190

Ser Ser Ile Val Pro Leu Ile Asp Gly Gly Thr Glu Gly Phe Lys Gly
                 195                 200                 205

Asn Ala Arg Val Ile Leu Pro Gly Met Thr Ala Cys Ile Glu Cys Thr
                 210                 215                 220

Leu Glu Leu Tyr Pro Pro Gln Val Asn Phe Pro Met Cys Thr Ile Ala
225                  230                 235                 240

Ser Met Pro Arg Leu Pro Glu His Cys Ile Glu Tyr Val Arg Met Leu
                 245                 250                 255

Gln Trp Pro Lys Glu Gln Pro Phe Gly Glu Gly Val Pro Leu Asp Gly
                 260                 265                 270

Asp Asp Pro Glu His Ile Gln Trp Ile Phe Gln Lys Ser Leu Glu Arg
                 275                 280                 285

Ala Ser Gln Tyr Asn Ile Arg Gly Val Thr Tyr Arg Leu Thr Gln Gly
                 290                 295                 300

Val Val Lys Arg Ile Ile Pro Ala Val Ala Ser Thr Asn Ala Val Ile
305                  310                 315                 320

Ala Ala Val Cys Ala Thr Glu Val Phe Lys Ile Ala Thr Ser Ala Tyr
                 325                 330                 335

Ile Pro Leu Asn Asn Tyr Leu Val Phe Asn Asp Val Asp Gly Leu Tyr
                 340                 345                 350

Thr Tyr Thr Phe Glu Ala Glu Arg Lys Glu Asn Cys Pro Ala Cys Ser
                 355                 360                 365

Gln Leu Pro Gln Asn Ile Gln Phe Ser Pro Ser Ala Lys Leu Gln Glu
                 370                 375                 380

Val Leu Asp Tyr Leu Thr Asn Ser Ala Ser Leu Gln Met Lys Ser Pro
385                  390                 395                 400

Ala Ile Thr Ala Thr Leu Glu Gly Lys Asn Arg Thr Leu Tyr Leu Gln
                 405                 410                 415

Ser Val Thr Ser Ile Glu Glu Arg Thr Arg Pro Asn Leu Ser Lys Thr
                 420                 425                 430
```

Leu Lys Glu Leu Gly Leu Val Asp Gly Gln Glu Leu Ala Val Ala Asp
435                 440                 445

Val Thr Thr Pro Gln Thr Val Leu Phe Lys Leu His Phe Thr Ser
450                 455                 460

<210> SEQ ID NO 9
<211> LENGTH: 2120
<212> TYPE: DNA
<213> ORGANISM: Homo sapiens
<220> FEATURE:
<221> NAME/KEY: misc_feature
<223> OTHER INFORMATION: GenBank Accession No.: AF046024

<400> SEQUENCE: 9

| | | | | |
|---|---|---|---|---|
| ctacgtttcc | agtgacctga | cagcagagga | ggggaggagc cggagaagaa | aagaaggaga | 60 |
| atagaggagc | tgctggctga | gaaaatggct | gttgatggtg ggtgtgggga | cactggagac | 120 |
| tgggaaggtc | gctggaacca | tgtaaagaag | ttcctcgagc gatctggacc | cttcacacac | 180 |
| cctgatttcg | aaccgagcac | tgaatctctc | cagttcttgt tagatacatg | taaagttcta | 240 |
| gtcattggag | ctggcggctt | aggatgtgag | ctcctgaaaa atctggcctt | gtctggtttt | 300 |
| agacagattc | atgttataga | tatggacact | atagatgttt ccaatctaaa | taggcagttt | 360 |
| ttatttaggc | ctaaagatat | tggaagacct | aaggctgaag ttgctgcaga | atttctaaat | 420 |
| gacagagttc | ctaattgcaa | tgtagttcca | catttcaaca agattcaaga | ttttaacgac | 480 |
| actttctatc | gacaatttca | tattattgta | tgtggactgg actctatcat | cgccagaaga | 540 |
| tggataaatg | gcatgctgat | atctcttcta | aattatgaag atggtgtctt | agatccaagc | 600 |
| tccattgtcc | ctttgataga | tgggggggaca | gaaggtttta aggaaatgc | ccgggtgatt | 660 |
| ctgcctggaa | tgactgcttg | tatcgaatgc | acgctggaac tttatccccc | acaggttaat | 720 |
| tttcccatgt | gcaccattgc | atctatgccc | aggctaccag aacactgtat | tgagtatgta | 780 |
| aggatgttgc | agtggcctaa | ggagcagcct | tttggagaag gggttccatt | agatggagat | 840 |
| gatcctgaac | atatacaatg | gattttccaa | aaatccctag agagagcatc | acaatataat | 900 |
| attaggggtg | ttacgtatag | gctcactcaa | ggggtagtaa aaagaatcat | tcctgcagta | 960 |
| gcttccacaa | atgcagtcat | tgcagctgtg | tgtgccactg aggttttaa | aatagccaca | 1020 |
| agtgcataca | ttcccttgaa | taattacttg | gtgtttaatg atgtagatgg | gctgtataca | 1080 |
| tacacatttg | aagcagaaag | aaaggaaaac | tgcccagctt gtagccagct | tcctcaaaat | 1140 |
| attcagtttt | ctccatcagc | taaactacag | gaggttttgg attatctaac | caatagtgct | 1200 |
| tctctgcaaa | tgaaatctcc | agccatcaca | gccaccctag agggaaaaaa | tagaacactt | 1260 |
| tacttacagt | cggtaacctc | tattgaagaa | cgaacaaggc caaatctctc | caaaacattg | 1320 |
| aaagaattgg | ggcttgttga | tggacaagaa | ctggcggttg ctgatgtcac | cacccccacag | 1380 |
| actgtactat | tcaaacttca | ttttacttct | taaggaaaat ctccacataa | tagaaaactc | 1440 |
| atggaaataa | tatactttgt | ggatgctaag | aagttgaatc cgatgtcatt | tttagcaata | 1500 |
| gtgttgccac | ggatttggtc | tttttttata | taatggaccc actctttttt | taccttgtaa | 1560 |
| ccttcccttg | aagcagaatt | ttgggtgttg | gtgcttgtaa atttccatta | ataatatgag | 1620 |
| aaatgatacc | tggagagaga | gattatgagc | aaatgtattg cttcttttag | aggaggaagc | 1680 |
| atacaacctc | ttttgtgtag | gttttgttat | tatggtcaaa gaatgcatcc | taagtttttca | 1740 |
| tttgagtacc | caaatacaca | aaaggtgtcc | ctttaaggaa aataaagaat | taagtttaa | 1800 |
| ataacattac | attttacaat | ctgacatctg | gagtatattg aacataggct | atttcttgat | 1860 |

-continued

```
ataacactca tttaattgtg gccatccaaa tgaatattat tgcagaattt atcttgttca    1920
taatgatttg taaatggtgt tatagctgaa tacctgtgca tgaaaatggg caatattttc    1980
atctgtttac ttgtagtgcc atagaggcca atatgcacaa tattaactaa tgccaagaca    2040
tggctgttta aaaaatttaa tgttcaaaca gttatcactg atgcttttgc actatttatt    2100
aataaaatca tatattgtgt                                                2120
```

```
<210> SEQ ID NO 10
<211> LENGTH: 442
<212> TYPE: PRT
<213> ORGANISM: Homo sapiens
<220> FEATURE:
<221> NAME/KEY: MISC_FEATURE
<223> OTHER INFORMATION: GenBank Accession No.: AAC27648

<400> SEQUENCE: 10
```

```
Met Ala Val Asp Gly Gly Cys Gly Asp Thr Gly Asp Trp Glu Gly Arg
  1               5                  10                  15

Trp Asn His Val Lys Lys Phe Leu Glu Arg Ser Gly Pro Phe Thr His
                 20                  25                  30

Pro Asp Phe Glu Pro Ser Thr Glu Ser Leu Gln Phe Leu Leu Asp Thr
             35                  40                  45

Cys Lys Val Leu Val Ile Gly Ala Gly Gly Leu Gly Cys Glu Leu Leu
         50                  55                  60

Lys Asn Leu Ala Leu Ser Gly Phe Arg Gln Ile His Val Ile Asp Met
 65                  70                  75                  80

Asp Thr Ile Asp Val Ser Asn Leu Asn Arg Gln Phe Leu Phe Arg Pro
                 85                  90                  95

Lys Asp Ile Gly Arg Pro Lys Ala Glu Val Ala Ala Glu Phe Leu Asn
            100                 105                 110

Asp Arg Val Pro Asn Cys Asn Val Val Pro His Phe Asn Lys Ile Gln
        115                 120                 125

Asp Phe Asn Asp Thr Phe Tyr Arg Gln Phe His Ile Ile Val Cys Gly
    130                 135                 140

Leu Asp Ser Ile Ile Ala Arg Arg Trp Ile Asn Gly Met Leu Ile Ser
145                 150                 155                 160

Leu Leu Asn Tyr Glu Asp Gly Val Leu Asp Pro Ser Ser Ile Val Pro
                165                 170                 175

Leu Ile Asp Gly Gly Thr Glu Gly Phe Lys Gly Asn Ala Arg Val Ile
            180                 185                 190

Leu Pro Gly Met Thr Ala Cys Ile Glu Cys Thr Leu Glu Leu Tyr Pro
        195                 200                 205

Pro Gln Val Asn Phe Pro Met Cys Thr Ile Ala Ser Met Pro Arg Leu
    210                 215                 220

Pro Glu His Cys Ile Glu Tyr Val Arg Met Leu Gln Trp Pro Lys Glu
225                 230                 235                 240

Gln Pro Phe Gly Glu Gly Val Pro Leu Asp Gly Asp Pro Glu His
                245                 250                 255

Ile Gln Trp Ile Phe Gln Lys Ser Leu Glu Arg Ala Ser Gln Tyr Asn
            260                 265                 270

Ile Arg Gly Val Thr Tyr Arg Leu Thr Gln Gly Val Val Lys Arg Ile
        275                 280                 285

Ile Pro Ala Val Ala Ser Thr Asn Ala Val Ile Ala Ala Val Cys Ala
    290                 295                 300
```

```
Thr Glu Val Phe Lys Ile Ala Thr Ser Ala Tyr Ile Pro Leu Asn Asn
305                 310                 315                 320

Tyr Leu Val Phe Asn Asp Val Asp Gly Leu Tyr Thr Tyr Thr Phe Glu
                325                 330                 335

Ala Glu Arg Lys Glu Asn Cys Pro Ala Cys Ser Gln Leu Pro Gln Asn
            340                 345                 350

Ile Gln Phe Ser Pro Ser Ala Lys Leu Gln Glu Val Leu Asp Tyr Leu
        355                 360                 365

Thr Asn Ser Ala Ser Leu Gln Met Lys Ser Pro Ala Ile Thr Ala Thr
    370                 375                 380

Leu Glu Gly Lys Asn Arg Thr Leu Tyr Leu Gln Ser Val Thr Ser Ile
385                 390                 395                 400

Glu Glu Arg Thr Arg Pro Asn Leu Ser Lys Thr Leu Lys Glu Leu Gly
                405                 410                 415

Leu Val Asp Gly Gln Glu Leu Ala Val Ala Asp Val Thr Thr Pro Gln
            420                 425                 430

Thr Val Leu Phe Lys Leu His Phe Thr Ser
        435                 440

<210> SEQ ID NO 11
<211> LENGTH: 2682
<212> TYPE: DNA
<213> ORGANISM: Homo sapiens
<220> FEATURE:
<221> NAME/KEY: misc_feature
<223> OTHER INFORMATION: GenBank Accession No.: NM_005499

<400> SEQUENCE: 11
ccccacccgc ttccggccgc ggctcggttc tcccgcctcc gcctccgccg cggctcgtgg     60
ttgtcccgcc atggcactgt cgcgggggct gccccgggag ctggctgagg cggtggccgg    120
gggccgggtg ctggtggtgg gggcggggcg catcggctgc gagctcctca agaatctcgt    180
gctcaccggt ttctcccaca tcgacctgat tgatctggat actattgatg taagcaacct    240
caacagacag tttttgtttc aaaagaaaca tgttggaaga tcaaaggcac aggttgccaa    300
ggaaagtgta ctgcagtttt acccgaaagc taatatcgtt gcctaccatg acagcatcat    360
gaaccctgac tataatgtgg aattttttccg acagtttata ctggttatga atgctttaga    420
taacagagct gcccgaaacc atgttaatag aatgtgcctg gcagctgatg ttcctcttat    480
tgaaagtgga acagctgggt atcttggaca agtaactact atcaaaaagg gtgtgaccga    540
gtgttatgag tgtcatccta agccgaccca gagaaccttt cctggctgta caattcgtaa    600
cacaccttca gaacctatac attgcatcgt ttgggcaaag tacttgttca accagttgtt    660 tgggggaagaa gatgctgatc aagaagtatc tcctgacaga gctgaccctg aagctgcctg    720
ggaaccaacg gaagccgaag ccagagctag agcatctaat gaagatggtg acattaaacg    780
tatttctact aaggaatggg ctaaatcaac tggatatgat ccagttaaac tttttaccaa    840 gcttttttaaa gatgacatca ggtatctgtt gacaatggac aaactatggc ggaaaaggaa    900
acctccagtt ccgttggact gggctgaagt acaaagtcaa ggagaagaaa cgaatgcatc    960
agatcaacag aatgaacccc agttaggcct gaaagaccag caggttctag atgtaaagag   1020
ctatgcacgc ctttttttcaa agagcatcga gactttgaga gttcatttag cagaaaaggg   1080
ggatggagct gagctcatat gggataagga tgacccatct gcaatggatt tgtcaccctc   1140
tgctgcaaac ctcaggatgc atattttcag tatgaatatg aagagtagat tgatatcaa   1200 atcaatggca gggaacatta ttcctgctat tgctactact aatgcagtaa ttgctgggtt   1260
```

-continued

```
gatagtattg aaggattga agattttatc aggaaaaata gaccagtgca gaacaatttt    1320
tttgaataaa caaccaaacc caagaaagaa gcttcttgtg ccttgtgcac tggatcctcc    1380 caacccaat tgttatgtat gtgccagcaa gccagaggtg actgtgcggc tgaatgtcca    1440
taaagtgact gttctcacct acaagacaa gatagtgaaa gaaaaatttg ctatggtagc    1500
accagatgtc caaattgaag atgggaaagg aacaatccta atatcttccg aagagggaga    1560
gacggaagct aataatcaca agaagttgtc agaatttgga attagaaatg cagccggct    1620 tcaagcagat gacttcctcc aggactatac tttattgatc aacatccttc atagtgaaga    1680
cctaggaaag gacgttgaat tgaagttgt tggtgatgcc ccggaaaaag tggggcccaa    1740
acaagctgaa gatgctgcca aaagcataac caatggcagt gatgatggag ctcagccctc    1800
cacctccaca gctcaagagc aagatgacgt tctcatagtt gattcagatg aagaagattc    1860
ttcaaataat gccgacgtca gtgaagaaga gagaagccgc aagaggaaat tagatgagaa    1920
agagaatctc agtgcaaaga ggtcacgtat agaacagaag gaagagcttg atgatgtcat    1980
agcattagat tgaacagaaa tgcctctaaa cagaacctc ttactattta gtttatctgg    2040
gcagaaccag attgttatgt cctttgttcc aaagggaaaa aattgacagc agtgacttga    2100
aaatgattct gctcccttt aaagcattca ttttgctaga actgttagac acattgcagt    2160
atgctgtatt gaaagtagga atatagtttt aaaaacccctt tgaacaaagt gtgtgcataa    2220
ccagtcatga gataaaacaa cacaatgcat gttgccttt taatgtaaat acccgtaggt    2280
atcattaata gtttcaaaat attgtggttt agtaaagttg atacctggtt ataaatatta    2340
tgcctttatt tttggctaga agaagaatta ttttttagcct agatctaacc attttcatac    2400
tcttaactga ttgaaacaga ttcaagaag tatcgagtgc tatgcattga aacttgtttt    2460
taaatgttag atggcactat gtatattaat gtaaacaat gttaattac tcaagttttc    2520 agtttgtacc gcctggtatg tctgtgtaag aagccaattt ttgtgtattg ttacagtttc    2580
aggttattta tattcgatgt tttgtaaaac tcaaataacg actatactta tggaccaaat    2640
aaatggcatc tgcattcttg ttacaaaaaa aaaaaaaaa aa                        2682
```

<210> SEQ ID NO 12
<211> LENGTH: 640
<212> TYPE: PRT
<213> ORGANISM: Homo sapiens
<220> FEATURE:
<221> NAME/KEY: MISC_FEATURE
<223> OTHER INFORMATION: GenBank Accession No.: NP_005490

<400> SEQUENCE: 12

```
Met Ala Leu Ser Arg Gly Leu Pro Arg Glu Leu Ala Glu Ala Val Ala
1               5                   10                  15

Gly Gly Arg Val Leu Val Val Gly Ala Gly Gly Ile Gly Cys Glu Leu
            20                  25                  30

Leu Lys Asn Leu Val Leu Thr Gly Phe Ser His Ile Asp Leu Ile Asp
        35                  40                  45

Leu Asp Thr Ile Asp Val Ser Asn Leu Asn Arg Gln Phe Leu Phe Gln
    50                  55                  60

Lys Lys His Val Gly Arg Ser Lys Ala Gln Val Ala Lys Glu Ser Val
65                  70                  75                  80

Leu Gln Phe Tyr Pro Lys Ala Asn Ile Val Ala Tyr His Asp Ser Ile
                85                  90                  95

Met Asn Pro Asp Tyr Asn Val Glu Phe Phe Arg Gln Phe Ile Leu Val
```

-continued

```
                100                 105                 110
    Met Asn Ala Leu Asp Asn Arg Ala Ala Arg Asn His Val Asn Arg Met
                    115                 120                 125
    Cys Leu Ala Ala Asp Val Pro Leu Ile Glu Ser Gly Thr Ala Gly Tyr
                130                 135                 140
    Leu Gly Gln Val Thr Thr Ile Lys Lys Gly Val Thr Glu Cys Tyr Glu
    145                 150                 155                 160
    Cys His Pro Lys Pro Thr Gln Arg Thr Phe Pro Gly Cys Thr Ile Arg
                    165                 170                 175
    Asn Thr Pro Ser Glu Pro Ile His Cys Ile Val Trp Ala Lys Tyr Leu
                180                 185                 190
    Phe Asn Gln Leu Phe Gly Glu Glu Asp Ala Asp Gln Glu Val Ser Pro
                    195                 200                 205
    Asp Arg Ala Asp Pro Glu Ala Ala Trp Glu Pro Thr Glu Ala Glu Ala
    210                 215                 220
    Arg Ala Arg Ala Ser Asn Glu Asp Gly Asp Ile Lys Arg Ile Ser Thr
    225                 230                 235                 240
    Lys Glu Trp Ala Lys Ser Thr Gly Tyr Asp Pro Val Lys Leu Phe Thr
                    245                 250                 255
    Lys Leu Phe Lys Asp Asp Ile Arg Tyr Leu Leu Thr Met Asp Lys Leu
                260                 265                 270
    Trp Arg Lys Arg Lys Pro Pro Val Pro Leu Asp Trp Ala Glu Val Gln
                    275                 280                 285
    Ser Gln Gly Glu Glu Thr Asn Ala Ser Asp Gln Gln Asn Glu Pro Gln
                290                 295                 300
    Leu Gly Leu Lys Asp Gln Gln Val Leu Asp Val Lys Ser Tyr Ala Arg
    305                 310                 315                 320
    Leu Phe Ser Lys Ser Ile Glu Thr Leu Arg Val His Leu Ala Glu Lys
                    325                 330                 335
    Gly Asp Gly Ala Glu Leu Ile Trp Asp Lys Asp Pro Ser Ala Met
                340                 345                 350
    Asp Phe Val Thr Ser Ala Ala Asn Leu Arg Met His Ile Phe Ser Met
                    355                 360                 365
    Asn Met Lys Ser Arg Phe Asp Ile Lys Ser Met Ala Gly Asn Ile Ile
                370                 375                 380
    Pro Ala Ile Ala Thr Thr Asn Ala Val Ile Ala Gly Leu Ile Val Leu
    385                 390                 395                 400
    Glu Gly Leu Lys Ile Leu Ser Gly Lys Ile Asp Gln Cys Arg Thr Ile
                    405                 410                 415
    Phe Leu Asn Lys Gln Pro Asn Pro Arg Lys Lys Leu Leu Val Pro Cys
                420                 425                 430
    Ala Leu Asp Pro Pro Asn Pro Asn Cys Tyr Val Cys Ala Ser Lys Pro
                    435                 440                 445
    Glu Val Thr Val Arg Leu Asn Val His Lys Val Thr Val Leu Thr Leu
                450                 455                 460
    Gln Asp Lys Ile Val Lys Glu Lys Phe Ala Met Val Ala Pro Asp Val
    465                 470                 475                 480
    Gln Ile Glu Asp Gly Lys Gly Thr Ile Leu Ile Ser Ser Glu Glu Gly
                    485                 490                 495
    Glu Thr Glu Ala Asn Asn His Lys Lys Leu Ser Glu Phe Gly Ile Arg
                500                 505                 510
    Asn Gly Ser Arg Leu Gln Ala Asp Asp Phe Leu Gln Asp Tyr Thr Leu
                    515                 520                 525
```

```
Leu Ile Asn Ile Leu His Ser Glu Asp Leu Gly Lys Asp Val Glu Phe
        530                 535                 540

Glu Val Val Gly Asp Ala Pro Glu Lys Val Gly Pro Lys Gln Ala Glu
545                 550                 555                 560

Asp Ala Ala Lys Ser Ile Thr Asn Gly Ser Asp Gly Ala Gln Pro
                565                 570                 575

Ser Thr Ser Thr Ala Gln Glu Gln Asp Val Leu Ile Val Asp Ser
                580                 585                 590

Asp Glu Glu Asp Ser Ser Asn Asn Ala Asp Val Ser Glu Glu Arg
            595                 600                 605

Ser Arg Lys Arg Lys Leu Asp Glu Lys Glu Asn Leu Ser Ala Lys Arg
        610                 615                 620

Ser Arg Ile Glu Gln Lys Glu Glu Leu Asp Asp Val Ile Ala Leu Asp
625                 630                 635                 640

<210> SEQ ID NO 13
<211> LENGTH: 2119
<212> TYPE: DNA
<213> ORGANISM: Homo sapiens
<220> FEATURE:
<221> NAME/KEY: misc_feature
<223> OTHER INFORMATION: GenBank Accession No.: NM_005500

<400> SEQUENCE: 13
ttggcttgag cgggaccgga gcttgaggca ggaagagccg gcgccatggt ggagaaggag      60
gaggctggcg gcggcattag cgaggaggag gcggcacagt atgaccggca gatccgcctg     120
tggggactgg aggcccagaa acggctgcgg gcctctcggg tgcttcttgt cggcttgaaa     180
ggacttgggg ctgaaattgc caagaatctc atcttggcag gagtgaaagg actgaccatg     240
ctggatcacg aacaggtaac tccagaagat cccggagctc agttcttgat tcgtactggg     300
tctgttggcc gaaatagggc tgaagcctct ttggagcgag ctcagaatct caaccccatg     360
gtggatgtga aggtggacac tgaggatata gagaagaaac agagtcattt tttcactcaa     420
ttcgatgctg tgtgtctgac ttgctgctcc agggatgtca tagttaaagt tgaccagatc     480
tgtcacaaaa atagcatcaa gttctttaca ggagatgttt ttggctacca tggatacaca     540
tttgccaatc taggagagca tgagtttgta gaggagaaaa ctaaagttgc aaagttagc     600 caaggagtag aagatgggcc cgacaccaag agagcaaaac ttgattcttc tgagacaacg     660
atggtcaaaa agaaggtggt cttctgcccct gttaaagaag ccctggaggt ggactggagc     720
agtgagaaag caaaggctgc tctgaagcgc acgacctccg actactttct ccttcaagtg     780
ctcttaaagt tccgtacaga taaggaaga gatcccagtt ctgatacata tgaggaagat     840
tctgagttgt tgctccagat acgaaatgat gtgcttgact cactgggtat tagtcctgac     900
ctgcttcctg aggactttgt caggtactgc ttctccgaga tggccccagt gtgtgcggtg     960
gttggaggga tttggcaca ggaaattgtg aaggccctgt ctcagcggga ccctcctcac    1020
aacaacttct tcttcttcga tggcatgaag gggaatggga ttgtggagtg ccttggcccc    1080
aagtgaactc aagatttggc agccccagag atgccaactg cagcatgccc acctgtattc    1140
cctgtcccct tccttcatga aggcatctcc aggcaaggaa aactgaagtc attggcccga    1200
tacaaaacat ttcctgcaac gaaggaggtg gtgccgacgt gctgcttccc atcaccagca    1260
gctgctcgac aagggcgca gggtggctgt ctttgttcca gcactgttca ggctgcctgt    1320
catcccgggc ctgccagctc ccctgagtga tgagcacttc caagcacccc tctgcccttt    1380
```

```
ctctgtcctt atgctgtccc ggcctcgcag ccctctgggg aattgtggga gatgcctgcc      1440
aggaatgagc aagctctgtt gctcgggagc ctccttgtaac cttcttggac ttattcccca    1500
cctgatacct tatagagaaa agtgtgaatt caggtggaga gtaggcccag gcccatgagg     1560
caccagtgga agcacagctc caagttcaga caggtgccct tagagaggaa aaccatgaca    1620
ggcaaatgca tttcctctgg agtttgagac cctgacaaac aacaggtggc atcctggtgt    1680
gctgttcttg agttttcgtt taggattagt tgagttccag ctgggttttg ggagaaagga    1740
gatgctacca agtctttgga tgttaagggc cgagacccct gcaaagttga gtattagaga   1800
gcttgtcttt caaggccagg ttccctgggg cttcaagggc taggagggag gagcctgccc     1860
cttttaacag aaccccccagt tacatgcggc tcaagtcact cagaggctgt tgcatttcag     1920
ggctatgttg gtcctttgtt tacctcctaa accacagctg tttgtgtttc acatatgttg     1980
tgaattttcc ttggttcttt ttaaaggaat gataataaag ttacttgctt taggatttgc    2040 ttgttttttct tccacttcag aagcttctga gagggaatgg gatgatccta ccagttgcct   2100
tttcagacct gaggctcta                                                  2119
```

<210> SEQ ID NO 14
<211> LENGTH: 346
<212> TYPE: PRT
<213> ORGANISM: Homo sapiens
<220> FEATURE:
<221> NAME/KEY: MISC_FEATURE
<223> OTHER INFORMATION: GenBank Accession No.: NP_005491

<400> SEQUENCE: 14

```
Met Val Glu Lys Glu Glu Ala Gly Gly Gly Ile Ser Glu Glu Glu Ala
1               5                   10                  15

Ala Gln Tyr Asp Arg Gln Ile Arg Leu Trp Gly Leu Glu Ala Gln Lys
            20                  25                  30

Arg Leu Arg Ala Ser Arg Val Leu Leu Val Gly Leu Lys Gly Leu Gly
        35                  40                  45

Ala Glu Ile Ala Lys Asn Leu Ile Leu Ala Gly Val Lys Gly Leu Thr
    50                  55                  60

Met Leu Asp His Glu Gln Val Thr Pro Glu Asp Pro Gly Ala Gln Phe
65                  70                  75                  80

Leu Ile Arg Thr Gly Ser Val Gly Arg Asn Arg Ala Glu Ala Ser Leu
                85                  90                  95

Glu Arg Ala Gln Asn Leu Asn Pro Met Val Asp Val Lys Val Asp Thr
            100                 105                 110

Glu Asp Ile Glu Lys Lys Pro Glu Ser Phe Phe Thr Gln Phe Asp Ala
        115                 120                 125

Val Cys Leu Thr Cys Cys Ser Arg Asp Val Ile Val Lys Val Asp Gln
    130                 135                 140

Ile Cys His Lys Asn Ser Ile Lys Phe Phe Thr Gly Asp Val Phe Gly
145                 150                 155                 160

Tyr His Gly Tyr Thr Phe Ala Asn Leu Gly Glu His Glu Phe Val Glu
                165                 170                 175

Glu Lys Thr Lys Val Ala Lys Val Ser Gln Gly Val Glu Asp Gly Pro
            180                 185                 190

Asp Thr Lys Arg Ala Lys Leu Asp Ser Ser Glu Thr Thr Met Val Lys
        195                 200                 205

Lys Lys Val Val Phe Cys Pro Val Lys Glu Ala Leu Glu Val Asp Trp
    210                 215                 220
```

-continued

| Ser | Ser | Glu | Lys | Ala | Lys | Ala | Ala | Leu | Lys | Arg | Thr | Thr | Ser | Asp | Tyr |
| 225 | | | | 230 | | | | | 235 | | | | | 240 | |

| Phe | Leu | Leu | Gln | Val | Leu | Leu | Lys | Phe | Arg | Thr | Asp | Lys | Gly | Arg | Asp |
| | | | | 245 | | | | | 250 | | | | | 255 | |

| Pro | Ser | Ser | Asp | Thr | Tyr | Glu | Glu | Asp | Ser | Glu | Leu | Leu | Leu | Gln | Ile |
| | | | 260 | | | | | 265 | | | | | 270 | | |

| Arg | Asn | Asp | Val | Leu | Asp | Ser | Leu | Gly | Ile | Ser | Pro | Asp | Leu | Leu | Pro |
| | | 275 | | | | | 280 | | | | | 285 | | | |

| Glu | Asp | Phe | Val | Arg | Tyr | Cys | Phe | Ser | Glu | Met | Ala | Pro | Val | Cys | Ala |
| | 290 | | | | | 295 | | | | | 300 | | | | |

| Val | Val | Gly | Gly | Ile | Leu | Ala | Gln | Glu | Ile | Val | Lys | Ala | Leu | Ser | Gln |
| 305 | | | | 310 | | | | | 315 | | | | | 320 | |

| Arg | Asp | Pro | Pro | His | Asn | Asn | Phe | Phe | Phe | Asp | Gly | Met | Lys | Gly |
| | | | | 325 | | | | | 330 | | | | | 335 |

| Asn | Gly | Ile | Val | Glu | Cys | Leu | Gly | Pro | Lys |
| | | | 340 | | | | | 345 | |

<210> SEQ ID NO 15
<211> LENGTH: 1221
<212> TYPE: DNA
<213> ORGANISM: Homo sapiens
<220> FEATURE:
<221> NAME/KEY: misc_feature
<223> OTHER INFORMATION: GenBank Accession No.: XM_090110

<400> SEQUENCE: 15

```
atggtaattt ttgctgtggt ctatgattct acattattca cacatctcaa aacctttcct      60
gctgattctt tgagccaggg gaaattttt actctgagca gtctacatcc tctgactttg     120
ggggaaggag gaggctgcag gagaaagtca gtggatgcct ggaagactag ggcactgccg     180
gtgaggcaac tggttcctga gcacaatcag atgttttgg agactcggaa attcttaaag     240
ggacatcaga ggagttggat tcctgcatta cttagtggga gcacagccag gtcagagtct     300
gtagaaggcg aacactccct ccctggtgca catcatggtt ttccccaggt gcttcttgca     360
ggcatgaaag gactcggggc tgaaattgcc aagaatctca tcctggcagg agtgaaagga     420
ctgaccatgc tggatcacaa acagatatct ccagaagaac ccggagctca gttcttgatt     480
cgtattgggt ctgttggccg aaatagggct gaagcctctt ggagcgagc tcagaatctt     540
aaccccatgg tggatgtgaa gttggacact gaggatatag aagaaaaccc agagtcattt     600
ttcactcaat ttgatgctgt tgaccagatc tgtcacaaaa atagcatcaa gttcttgca      660
ggagatgttt ttagctacca tggatacaca tttgccaatc taggagaaca tgagtttgta     720
gaggagaaaa ctaaagttgc taaagttagc caaggagtag aagatgggcc tgataccaag     780
agagtaaaac ttgattcttc tgagacaacg atggtcaaga gaaggtggt cttctgcccc      840
gttaaagaag cgctggaggt ggactggagc agtaagaaag caaaggctgc tctgaagcgc     900
acgacctccg accactttct ccttcaagtg ctcctaaagt ccgcacaga taaggaaga     960
gatcccagtt ctgatacaca cggggaagat tccgagttgt tgctccagat acgaaacgat    1020
gtgcttgact cactgggtat tattcctgac ccgcgcttta tcacgtactt cttctctgag    1080
atggccccag tgtgtgcggt ggttggaggg attttggcac aggaaattgt gaaggccctg    1140
tctcagcagg accctcctca caacttcttc ttcaatggca tgaaggggaa tgggattctg    1200
gagtggcttg gccccaagtg a                                              1221
```

<210> SEQ ID NO 16

<211> LENGTH: 406
<212> TYPE: PRT
<213> ORGANISM: Homo sapiens
<220> FEATURE:
<221> NAME/KEY: MISC_FEATURE
<223> OTHER INFORMATION: GenBank Accession No.: XP_090110

<400> SEQUENCE: 16

```
Met Val Ile Phe Ala Val Val Tyr Asp Ser Thr Leu Phe Thr His Leu
1               5                   10                  15

Lys Thr Phe Pro Ala Asp Ser Leu Ser Gln Gly Lys Phe Phe Thr Leu
            20                  25                  30

Ser Ser Leu His Pro Leu Thr Leu Gly Glu Gly Gly Gly Cys Arg Arg
        35                  40                  45

Lys Ser Val Asp Ala Trp Lys Thr Arg Ala Leu Pro Val Arg Gln Leu
    50                  55                  60

Val Pro Glu His Asn Gln Met Phe Leu Glu Thr Arg Lys Phe Leu Lys
65                  70                  75                  80

Gly His Gln Arg Ser Trp Ile Pro Ala Leu Leu Ser Gly Ser Thr Ala
                85                  90                  95

Arg Ser Glu Ser Val Glu Gly Glu His Ser Leu Pro Gly Ala His His
            100                 105                 110

Gly Phe Pro Gln Val Leu Leu Ala Gly Met Lys Gly Leu Gly Ala Glu
        115                 120                 125

Ile Ala Lys Asn Leu Ile Leu Ala Gly Val Lys Gly Leu Thr Met Leu
    130                 135                 140

Asp His Lys Gln Ile Ser Pro Glu Glu Pro Gly Ala Gln Phe Leu Ile
145                 150                 155                 160

Arg Ile Gly Ser Val Gly Arg Asn Arg Ala Glu Ala Ser Leu Glu Arg
                165                 170                 175

Ala Gln Asn Leu Asn Pro Met Val Asp Val Lys Leu Asp Thr Glu Asp
            180                 185                 190

Ile Glu Lys Lys Pro Glu Ser Phe Phe Thr Gln Phe Asp Ala Val Asp
        195                 200                 205

Gln Ile Cys His Lys Asn Ser Ile Lys Phe Phe Ala Gly Asp Val Phe
    210                 215                 220

Ser Tyr His Gly Tyr Thr Phe Ala Asn Leu Gly Glu His Glu Phe Val
225                 230                 235                 240

Glu Glu Lys Thr Lys Val Ala Lys Val Ser Gln Gly Val Glu Asp Gly
                245                 250                 255

Pro Asp Thr Lys Arg Val Lys Leu Asp Ser Ser Glu Thr Thr Met Val
            260                 265                 270

Lys Lys Lys Val Val Phe Cys Pro Val Lys Glu Ala Leu Glu Val Asp
        275                 280                 285

Trp Ser Ser Lys Lys Ala Lys Ala Ala Leu Lys Arg Thr Thr Ser Asp
    290                 295                 300

His Phe Leu Leu Gln Val Leu Leu Lys Phe Arg Thr Asp Lys Gly Arg
305                 310                 315                 320

Asp Pro Ser Ser Asp Thr His Gly Glu Asp Ser Glu Leu Leu Leu Gln
                325                 330                 335

Ile Arg Asn Asp Val Leu Asp Ser Leu Gly Ile Ile Pro Asp Pro Arg
            340                 345                 350

Phe Ile Thr Tyr Phe Phe Ser Glu Met Ala Pro Val Cys Ala Val Val
        355                 360                 365

Gly Gly Ile Leu Ala Gln Glu Ile Val Lys Ala Leu Ser Gln Gln Asp
```

```
              370              375             380
Pro Pro His Asn Phe Phe Phe Asn Gly Met Lys Gly Asn Gly Ile Leu
385             390             395                 400

Glu Trp Leu Gly Pro Lys
            405

<210> SEQ ID NO 17
<211> LENGTH: 3330
<212> TYPE: DNA
<213> ORGANISM: Homo sapiens
<220> FEATURE:
<221> NAME/KEY: misc_feature
<223> OTHER INFORMATION: GenBank Accession No.: NM_003335

<400> SEQUENCE: 17
cttttctttt ctccaggaag agagctgtga ccagcagcgt cccttattcg cttggccttg      60
gttcctgttt gcactggcta cagcagggca ctggccccta ctgtcaccgc cacctacaca     120
aagaccctat ctctgagcgc tgcagcctac tgttcagccc caggtttgag gatggatgcc     180
ctggacgctt cgaagctact ggatgaggag ctgtattcaa gacagctgta tgtgctgggc     240
tcacctgcca tgcagaggat tcagggagcc agggtcctgg tgtcaggcct gcagggcctg     300
ggggccgagg tggccaagaa cttggttctg atgggtgtgg gcagcctcac tctgcatgat     360
ccccacccca cctgctggtc cgacctggct gcccagtttc cctctcaga gcaggacttg      420 gaaaggagca gagccgaggc ctctcaagag ctcttggctc agctcaacag agctgtccag     480
gtcgtcgtgc acacgggtga catcactgag gacctgctgt ggacttcca ggtggtggtg      540 ctgactgctg caaagctgga ggagcagctg aaggtgggca ccttgtgtca taagcatgga     600
gtttgctttc tggcggctga cacccggggc ctcgtgggc agttgttctg tgactttggt      660
gaggacttca ctgtgcagga ccccacagag gcagaacccc tgacagctgc catccagcac     720
atctcccagg gctcccctgg cattctcact ctgaggaaag gggccaatac ccactacttc     780
cgtgatggag acttggtgac tttctcggga attgagggaa tggttgagct caacgactgt     840
gatccccggt ctatccacgt gcgggaggat gggtccctgg agattggaga cacaacaact     900
ttctctcggt acttgcgtgg tgggctatc actgaagtca agagacccaa gactgtgaga     960
cataagtccc tggacacagc cctgctccag ccccatgtgg tggcccagag ctcccaggaa    1020
gttcaccatg cccactgcct gcatcaggcc ttctgtgcac tgcacaagtt ccagcacctc    1080
catggccggc cacccagcc ctgggatcct gttgatgcag agactgtggt gggcctggcc    1140
cgggacctgg aaccactgaa gcggacagag aaagagccac tggaagagcc actggatgag    1200
gccctagtgc ggacagtcgc cctaagcagt gcaggtgtct tgagccctat ggtggccatg    1260
ctgggtgcag tagctgccca ggaagtgctg aaggcaatct ccaggaagtt catgcctctg    1320
gaccagtggc tttactttga tgccctcgat tgtcttccgg aagatgggga gctccttccc    1380
agtcctgagg actgtgccct gagaggcagc cgctatgatg ggcaaattgc agtgtttggg    1440
gctggttttc aggagaaact gagacgccag cactacctcc tggtgggcgc tggtgccatt    1500
ggttgtgagc tgctcaaagt ctttgcccta gtgggactgg gggccgggaa cagcgggggc    1560
ttgactgttg ttgacatgga ccacatagag cgctccaatc tcagccgtca gttcctcttc    1620
aggtcccagg acgttggtag acccaaggca gaggtggctg cagcagctgc ccggggcctg    1680
aacccagact acaggtgat cccgctcacc tacccactgg atccaccac agagcacatc     1740 tatggggata acttttctc ccgtgtggat ggtgtggctg ctgccctgga cagtttccag    1800
```

-continued

```
gcccggcgct atgtggctgc tcgttgcacc cactatctga agccactgct ggaggcaggc    1860
acatcgggca cctggggcag tgctacagta ttcatgccac atgtgactga ggcctacaga    1920
gcccctgcct cagctgcagc ttctgaggat gccccctacc ctgtctgtac cgtgcggtac    1980
ttccctagca cagccgagca caccctgcag tgggcccggc atgagtttga agaactcttc    2040
cgactgtctg cagagaccat caaccaccac caacaggcac acacttccct ggcagacatg    2100
gatgagccac agacactcac cttactgaag ccagtgcttg ggtcctgag agtgcgtcca     2160
cagaactggc aagactgtgt ggcgtgggct cttggccact ggaaactctg ctttcattat    2220
ggcatcaaac agctgctgag gcacttccca cctaataaag tgcttgagga tggaactccc    2280
ttctggtcag gtcccaaaca gtgtccccag cccttggagt ttgacaccaa ccaagacaca    2340
cacctcctct acgtactggc agctgccaac ctgtatgccc agatgcatgg gctgcctggc    2400
tcacaggact ggactgcact cagggagctg ctgaagctgc tgccacagcc tgaccccaa    2460
cagatggccc ccatctttgc tagtaatcta gagctggctt cggcttctgc tgagtttggc    2520
cctgagcagc agaaggaact gaacaaagcc ctggaagtct ggagtgtggg ccctcccctg    2580
aagcctctga tgtttgagaa ggatgatgac agcaacttcc atgtggactt tgtggtagcg    2640
gcagctagcc tgagatgtca gaactacggg attccaccgg tcaaccgtgc ccagagcaag    2700
cgaattgtgg gccagattat cccagccatt gccaccacta cagcagctgt ggcaggcctg    2760
ttgggcctgg agctgtataa ggtggtgagt gggccacggc ctcgtagtgc ctttcgccac    2820
agctacctac atctggctga aaactacctc atccgctata tgccttttgc cccagccatc    2880
cagacgttcc atcacctgaa gtggacctct tgggaccgtc tgaaggtacc agctgggcag    2940
cctgagagga ccctggagtc gctgctggct catcttcagg agcagcacgg gttgagggtg    3000
aggatcctgc tgcacggctc agccctgctc tatgcggccg atggtcacc tgaaaagcag    3060
gcccagcacc tgcccctcag ggtgacagaa ctggttcagc agctgacagg ccaggcacct    3120
gctcctgggc agcgggtgtt ggtgctagag ctgagctgtg agggtgacga cgaggacact    3180
gccttcccac ctctgcacta tgagctgtga caaggcagcc accctgtcac ctagctcaat    3240
ggagccccgg atcccaagcc ctgcattgta agcccacagt aggcactcaa taaatgcttg    3300
ttaaaggaag gcaaaaaaaa aaaaaaaaa                                      3330
```

<210> SEQ ID NO 18
<211> LENGTH: 1012
<212> TYPE: PRT
<213> ORGANISM: Homo sapiens
<220> FEATURE:
<221> NAME/KEY: MISC_FEATURE
<223> OTHER INFORMATION: GenBank Accession No.: NP_003326

<400> SEQUENCE: 18

```
Met Asp Ala Leu Asp Ala Ser Lys Leu Leu Asp Glu Glu Leu Tyr Ser
1               5                   10                  15

Arg Gln Leu Tyr Val Leu Gly Ser Pro Ala Met Gln Arg Ile Gln Gly
                20                  25                  30

Ala Arg Val Leu Val Ser Gly Leu Gln Gly Leu Gly Ala Glu Val Ala
            35                  40                  45

Lys Asn Leu Val Leu Met Gly Val Gly Ser Leu Thr Leu His Asp Pro
        50                  55                  60

His Pro Thr Cys Trp Ser Asp Leu Ala Ala Gln Phe Leu Leu Ser Glu
65                  70                  75                  80

Gln Asp Leu Glu Arg Ser Arg Ala Glu Ala Ser Gln Glu Leu Leu Ala
```

```
                    85                  90                  95
Gln Leu Asn Arg Ala Val Gln Val Val His Thr Gly Asp Ile Thr
            100                 105                 110
Glu Asp Leu Leu Leu Asp Phe Gln Val Val Leu Thr Ala Ala Lys
        115                 120                 125
Leu Glu Glu Gln Leu Lys Val Gly Thr Leu Cys His Lys His Gly Val
    130                 135                 140
Cys Phe Leu Ala Ala Asp Thr Arg Gly Leu Val Gly Gln Leu Phe Cys
145                 150                 155                 160
Asp Phe Gly Glu Asp Phe Thr Val Gln Asp Pro Thr Glu Ala Glu Pro
                165                 170                 175
Leu Thr Ala Ala Ile Gln His Ile Ser Gln Gly Ser Pro Gly Ile Leu
            180                 185                 190
Thr Leu Arg Lys Gly Ala Asn Thr His Tyr Phe Arg Asp Gly Asp Leu
        195                 200                 205
Val Thr Phe Ser Gly Ile Glu Gly Met Val Glu Leu Asn Asp Cys Asp
    210                 215                 220
Pro Arg Ser Ile His Val Arg Glu Asp Gly Ser Leu Glu Ile Gly Asp
225                 230                 235                 240
Thr Thr Thr Phe Ser Arg Tyr Leu Arg Gly Gly Ala Ile Thr Glu Val
                245                 250                 255
Lys Arg Pro Lys Thr Val Arg His Lys Ser Leu Asp Thr Ala Leu Leu
            260                 265                 270
Gln Pro His Val Val Ala Gln Ser Ser Gln Glu Val His His Ala His
        275                 280                 285
Cys Leu His Gln Ala Phe Cys Ala Leu His Lys Phe Gln His Leu His
    290                 295                 300
Gly Arg Pro Pro Gln Pro Trp Asp Pro Val Asp Ala Glu Thr Val Val
305                 310                 315                 320
Gly Leu Ala Arg Asp Leu Glu Pro Leu Lys Arg Thr Glu Glu Pro
                325                 330                 335
Leu Glu Glu Pro Leu Asp Glu Ala Leu Val Arg Thr Val Ala Leu Ser
            340                 345                 350
Ser Ala Gly Val Leu Ser Pro Met Val Ala Met Leu Gly Ala Val Ala
        355                 360                 365
Ala Gln Glu Val Leu Lys Ala Ile Ser Arg Lys Phe Met Pro Leu Asp
    370                 375                 380
Gln Trp Leu Tyr Phe Asp Ala Leu Asp Cys Leu Pro Glu Asp Gly Glu
385                 390                 395                 400
Leu Leu Pro Ser Pro Glu Asp Cys Ala Leu Arg Gly Ser Arg Tyr Asp
                405                 410                 415
Gly Gln Ile Ala Val Phe Gly Ala Gly Phe Gln Glu Lys Leu Arg Arg
            420                 425                 430
Gln His Tyr Leu Leu Val Gly Ala Gly Ala Ile Gly Cys Glu Leu Leu
        435                 440                 445
Lys Val Phe Ala Leu Val Gly Leu Gly Ala Gly Asn Ser Gly Gly Leu
    450                 455                 460
Thr Val Val Asp Met Asp His Ile Glu Arg Ser Asn Leu Ser Arg Gln
465                 470                 475                 480
Phe Leu Phe Arg Ser Gln Asp Val Gly Arg Pro Lys Ala Glu Val Ala
                485                 490                 495
Ala Ala Ala Ala Arg Gly Leu Asn Pro Asp Leu Gln Val Ile Pro Leu
            500                 505                 510
```

```
Thr Tyr Pro Leu Asp Pro Thr Thr Glu His Ile Tyr Gly Asp Asn Phe
        515                 520                 525

Phe Ser Arg Val Asp Gly Val Ala Ala Ala Leu Asp Ser Phe Gln Ala
    530                 535                 540

Arg Arg Tyr Val Ala Ala Arg Cys Thr His Tyr Leu Lys Pro Leu Leu
545                 550                 555                 560

Glu Ala Gly Thr Ser Gly Thr Trp Gly Ser Ala Thr Val Phe Met Pro
                565                 570                 575

His Val Thr Glu Ala Tyr Arg Ala Pro Ala Ser Ala Ala Ser Glu
            580                 585                 590

Asp Ala Pro Tyr Pro Val Cys Thr Val Arg Tyr Phe Pro Ser Thr Ala
            595                 600                 605

Glu His Thr Leu Gln Trp Ala Arg His Glu Phe Glu Leu Phe Arg
        610                 615                 620

Leu Ser Ala Glu Thr Ile Asn His His Gln Gln Ala His Thr Ser Leu
625                 630                 635                 640

Ala Asp Met Asp Glu Pro Gln Thr Leu Thr Leu Leu Lys Pro Val Leu
                645                 650                 655

Gly Val Leu Arg Val Arg Pro Gln Asn Trp Gln Asp Cys Val Ala Trp
                660                 665                 670

Ala Leu Gly His Trp Lys Leu Cys Phe His Tyr Gly Ile Lys Gln Leu
                675                 680                 685

Leu Arg His Phe Pro Pro Asn Lys Val Leu Glu Asp Gly Thr Pro Phe
            690                 695                 700

Trp Ser Gly Pro Lys Gln Cys Pro Gln Pro Leu Glu Phe Asp Thr Asn
705                 710                 715                 720

Gln Asp Thr His Leu Leu Tyr Val Leu Ala Ala Asn Leu Tyr Ala
                725                 730                 735

Gln Met His Gly Leu Pro Gly Ser Gln Asp Trp Thr Ala Leu Arg Glu
            740                 745                 750

Leu Leu Lys Leu Leu Pro Gln Pro Asp Pro Gln Gln Met Ala Pro Ile
            755                 760                 765

Phe Ala Ser Asn Leu Glu Leu Ala Ser Ala Ser Ala Glu Phe Gly Pro
770                 775                 780

Glu Gln Gln Lys Glu Leu Asn Lys Ala Leu Glu Val Trp Ser Val Gly
785                 790                 795                 800

Pro Pro Leu Lys Pro Leu Met Phe Glu Lys Asp Asp Ser Asn Phe
            805                 810                 815

His Val Asp Phe Val Val Ala Ala Ser Leu Arg Cys Gln Asn Tyr
            820                 825                 830

Gly Ile Pro Pro Val Asn Arg Ala Gln Ser Lys Arg Ile Val Gly Gln
            835                 840                 845

Ile Ile Pro Ala Ile Ala Thr Thr Thr Ala Ala Val Ala Gly Leu Leu
            850                 855                 860

Gly Leu Glu Leu Tyr Lys Val Val Ser Gly Pro Arg Pro Arg Ser Ala
865                 870                 875                 880

Phe Arg His Ser Tyr Leu His Leu Ala Glu Asn Tyr Leu Ile Arg Tyr
                885                 890                 895

Met Pro Phe Ala Pro Ala Ile Gln Thr Phe His His Leu Lys Trp Thr
                900                 905                 910

Ser Trp Asp Arg Leu Lys Val Pro Ala Gly Gln Pro Glu Arg Thr Leu
            915                 920                 925
```

-continued

```
Glu Ser Leu Leu Ala His Leu Gln Glu Gln His Gly Leu Arg Val Arg
        930                 935                 940

Ile Leu Leu His Gly Ser Ala Leu Leu Tyr Ala Ala Gly Trp Ser Pro
945                 950                 955                 960

Glu Lys Gln Ala Gln His Leu Pro Leu Arg Val Thr Glu Leu Val Gln
            965                 970                 975

Gln Leu Thr Gly Gln Ala Pro Ala Pro Gly Gln Arg Val Leu Val Leu
        980                 985                 990

Glu Leu Ser Cys Glu Gly Asp Asp  Glu Asp Thr Ala Phe  Pro Pro Leu
        995                 1000                1005

His Tyr  Glu Leu
    1010
```

```
<210> SEQ ID NO 19
<211> LENGTH: 2396
<212> TYPE: DNA
<213> ORGANISM: Homo sapiens
<220> FEATURE:
<221> NAME/KEY: misc_feature
<223> OTHER INFORMATION: GenBank Accession No.: NM_006395

<400> SEQUENCE: 19
ggaagttgag cggcggcaag aaataatggc ggcagctacg ggggatcctg gactctctaa      60
actgcagttt gccccttta gtagtgcctt ggatgttggg ttttggcatg agttgaccca     120
gaagaagctg aacgagtatc ggctggatga agctcccaag gacattaagg gttattacta     180
caatggtgac tctgctgggc tgccagctcg cttaacattg gagttcagtg cttttgacat     240
gagtgctccc accccagccc gttgctgccc agctattgga acactgtata acaccaacac     300
actcgagtct ttcaagactg cagataagaa gctcctttg gaacaagcag caaatgagat     360
atgggaatcc ataaaatcag gcactgctct tgaaacccct gtactcctca caagttcct     420 cctcttgaca tttgcagatc taagaagta ccacttctac tattggtttt gctatcctgc     480
cctctgtctt ccagagagtt tacctctcat tcaggggcca gtgggtttgg atcaaaggtt     540
ttcactaaaa cagattgaag cactagagtg tgcatatgat aatctttgtc aaacagaagg     600
agtcacagct cttccttact tcttaatcaa gtatgatgag aacatggtgc tggtttcctt     660
gcttaaacac tacagtgatt tcttccaagg tcaaaggacg aagataacaa ttggtgtata     720
tgatccctgt aacttagccc agtaccctgg atggcctttg aggaattttt tggtcctagc     780
agcccacaga tggagtagca gtttccagtc tgttgaagtt gtttgcttcc gtgaccgtac     840
catgcagggg gcgagagacg ttgcccacag catcatcttc gaagtgaagc ttccagaaat     900
ggcatttagc ccagattgtc ctaaagcagt tggatgggaa aagaaccaga aaggaggcat     960
gggaccaagg atggtgaacc tcagtgaatg tatggaccct aaaaggttag ctgagtcatc    1020
agtggatcta aatctcaaac tgatgtgttg gagattggtt cctactttag acttggacaa    1080
ggttgtgtct gtcaaatgtc tgctgcttgg agccggcacc ttgggttgca atgtagctag    1140
gacgttgatg ggtgggggcg tgagacacat cacatttgtg gacaatgcca agatctccta    1200
ctccaatcct gtgaggcagc ctctctatga gtttgaagat tgcctagggg gtggtaagcc    1260
caaggctctg gcagcagcgg accggctcca gaaatattc cccggtgtga atgccagagg    1320
attcaacatg agcatacta tgcctgggca tccagtgaac ttctccagtg tcactctgga    1380
gcaagcccgc agagatgtgg agcaactgga gcagctcatc gaaagccatg atgtcgtctt    1440
cctattgatg gacaccaggg agagccggtg gcttcctgcc gtcattgctg caagcaagag    1500
```

-continued

```
aaagctggtc atcaatgctg ctttgggatt tgacacattt gttgtcatga gacatggtct      1560
gaagaaacca agcagcaag gagctgggga cttgtgtcca aaccaccctg tggcatctgc       1620
tgacctcctg ggctcatcgc ttttttgccaa catccctggt tacaagcttg ctgctactt     1680 ctgcaatgat gtggtggccc caggagattc aaccagagac cggaccttgg accagcagtg    1740
cactgtgagt cgtccaggac tggccgtgat tgcaggagcc ctggccgtgg aattgatggt    1800
atctgttttg cagcatccag aaggggggcta tgccattgcc agcagcagtg acgatcggat   1860
gaatgagcct ccaacctctc ttgggcttgt gcctcaccag atccggggat ttcttcacg      1920 gttgataat gtccttcccg tcagcctggc atttgacaaa tgtacagctt gttcttccaa       1980
agttcttgat caatatgaac gagaaggatt taacttccta gccaaggtgt ttaattcttc    2040
acattccttc ttagaagact tgactggtct tacattgctg catcaagaaa cccaagctgc   2100
tgagatctgg gacatgagcg atgatgagac catctgagat ggccccgctg tggggctgac  2160
ttctccctgg ccgcctgctg aggagctctc catcgccaga gcaggactgc tgaccccagg   2220
cctggtgatt ctgggcccct cctccatacc ccgaggtctg ggattccccc ctctgctgcc    2280
caggagtggc cagtgttcgg cgttgctcgg gattcaagat accaccagtt cagagctaaa    2340
taataacctt ggccttggcc ttgctattga cctgggaaaa aaaaaaaaaa aaaaaa         2396
```

<210> SEQ ID NO 20
<211> LENGTH: 703
<212> TYPE: PRT
<213> ORGANISM: Homo sapiens
<220> FEATURE:
<221> NAME/KEY: MISC_FEATURE
<223> OTHER INFORMATION: GenBank Accession No.: NP_006386

<400> SEQUENCE: 20

```
Met Ala Ala Ala Thr Gly Asp Pro Gly Leu Ser Lys Leu Gln Phe Ala
1               5                   10                  15

Pro Phe Ser Ser Ala Leu Asp Val Gly Phe Trp His Glu Leu Thr Gln
            20                  25                  30

Lys Lys Leu Asn Glu Tyr Arg Leu Asp Glu Ala Pro Lys Asp Ile Lys
        35                  40                  45

Gly Tyr Tyr Tyr Asn Gly Asp Ser Ala Gly Leu Pro Ala Arg Leu Thr
    50                  55                  60

Leu Glu Phe Ser Ala Phe Asp Met Ser Ala Pro Thr Pro Ala Arg Cys
65                  70                  75                  80

Cys Pro Ala Ile Gly Thr Leu Tyr Asn Thr Asn Thr Leu Glu Ser Phe
                85                  90                  95

Lys Thr Ala Asp Lys Lys Leu Leu Glu Gln Ala Ala Asn Glu Ile
            100                 105                 110

Trp Glu Ser Ile Lys Ser Gly Thr Ala Leu Glu Asn Pro Val Leu Leu
        115                 120                 125

Asn Lys Phe Leu Leu Leu Thr Phe Ala Asp Leu Lys Lys Tyr His Phe
    130                 135                 140

Tyr Tyr Trp Phe Cys Tyr Pro Ala Leu Cys Leu Pro Glu Ser Leu Pro
145                 150                 155                 160

Leu Ile Gln Gly Pro Val Gly Leu Asp Gln Arg Phe Ser Leu Lys Gln
                165                 170                 175

Ile Glu Ala Leu Glu Cys Ala Tyr Asp Asn Leu Cys Gln Thr Glu Gly
            180                 185                 190

Val Thr Ala Leu Pro Tyr Phe Leu Ile Lys Tyr Asp Glu Asn Met Val
        195                 200                 205
```

```
Leu Val Ser Leu Leu Lys His Tyr Ser Asp Phe Phe Gln Gly Gln Arg
    210                 215                 220

Thr Lys Ile Thr Ile Gly Val Tyr Asp Pro Cys Asn Leu Ala Gln Tyr
225                 230                 235                 240

Pro Gly Trp Pro Leu Arg Asn Phe Leu Val Leu Ala Ala His Arg Trp
                245                 250                 255

Ser Ser Ser Phe Gln Ser Val Glu Val Val Cys Phe Arg Asp Arg Thr
                260                 265                 270

Met Gln Gly Ala Arg Asp Val Ala His Ser Ile Ile Phe Glu Val Lys
            275                 280                 285

Leu Pro Glu Met Ala Phe Ser Pro Asp Cys Pro Lys Ala Val Gly Trp
    290                 295                 300

Glu Lys Asn Gln Lys Gly Gly Met Gly Pro Arg Met Val Asn Leu Ser
305                 310                 315                 320

Glu Cys Met Asp Pro Lys Arg Leu Ala Glu Ser Ser Val Asp Leu Asn
                325                 330                 335

Leu Lys Leu Met Cys Trp Arg Leu Val Pro Thr Leu Asp Leu Asp Lys
            340                 345                 350

Val Val Ser Val Lys Cys Leu Leu Leu Gly Ala Gly Thr Leu Gly Cys
    355                 360                 365

Asn Val Ala Arg Thr Leu Met Gly Trp Gly Val Arg His Ile Thr Phe
    370                 375                 380

Val Asp Asn Ala Lys Ile Ser Tyr Ser Asn Pro Val Arg Gln Pro Leu
385                 390                 395                 400

Tyr Glu Phe Glu Asp Cys Leu Gly Gly Gly Lys Pro Lys Ala Leu Ala
                405                 410                 415

Ala Ala Asp Arg Leu Gln Lys Ile Phe Pro Gly Val Asn Ala Arg Gly
            420                 425                 430

Phe Asn Met Ser Ile Pro Met Pro Gly His Pro Val Asn Phe Ser Ser
                435                 440                 445

Val Thr Leu Glu Gln Ala Arg Arg Asp Val Glu Gln Leu Glu Gln Leu
    450                 455                 460

Ile Glu Ser His Asp Val Val Phe Leu Leu Met Asp Thr Arg Glu Ser
465                 470                 475                 480

Arg Trp Leu Pro Ala Val Ile Ala Ala Ser Lys Arg Lys Leu Val Ile
                485                 490                 495

Asn Ala Ala Leu Gly Phe Asp Thr Phe Val Val Met Arg His Gly Leu
                500                 505                 510

Lys Lys Pro Lys Gln Gln Gly Ala Gly Asp Leu Cys Pro Asn His Pro
    515                 520                 525

Val Ala Ser Ala Asp Leu Leu Gly Ser Ser Leu Phe Ala Asn Ile Pro
    530                 535                 540

Gly Tyr Lys Leu Gly Cys Tyr Phe Cys Asn Asp Val Val Ala Pro Gly
545                 550                 555                 560

Asp Ser Thr Arg Asp Arg Thr Leu Asp Gln Gln Cys Thr Val Ser Arg
                565                 570                 575

Pro Gly Leu Ala Val Ile Ala Gly Ala Leu Ala Val Glu Leu Met Val
                580                 585                 590

Ser Val Leu Gln His Pro Glu Gly Gly Tyr Ala Ile Ala Ser Ser Ser
    595                 600                 605

Asp Asp Arg Met Asn Glu Pro Pro Thr Ser Leu Gly Leu Val Pro His
    610                 615                 620
```

```
Gln Ile Arg Gly Phe Leu Ser Arg Phe Asp Asn Val Leu Pro Val Ser
625                 630                 635                 640

Leu Ala Phe Asp Lys Cys Thr Ala Cys Ser Ser Lys Val Leu Asp Gln
            645                 650                 655

Tyr Glu Arg Glu Gly Phe Asn Phe Leu Ala Lys Val Phe Asn Ser Ser
        660                 665                 670

His Ser Phe Leu Glu Asp Leu Thr Gly Leu Thr Leu Leu His Gln Glu
        675                 680                 685

Thr Gln Ala Ala Glu Ile Trp Asp Met Ser Asp Glu Thr Ile
    690                 695                 700

<210> SEQ ID NO 21
<211> LENGTH: 2326
<212> TYPE: DNA
<213> ORGANISM: Homo sapiens
<220> FEATURE:
<221> NAME/KEY: misc_feature
<223> OTHER INFORMATION: GenBank Accession No.: BC000091

<400> SEQUENCE: 21
ggttgccgga agttgagcgg cggcaagaaa taatggcggc agctacgggg gatcctggac    60
tctctaaact gcagtttgcc ccttttagta gtgccttgga tgttgggttt tggcatgagt   120
tgacccagaa gaagctgaac gagtatcggc tggatgaagc tcccaaggac attaagggtt   180
attactacaa tggtgactct gctgggctgc cagctcgctt aacattggag ttcagtgctt   240
ttgacatgag tgctcccacc ccagcccgtt gctgcccagc tattgaaaca ctgtataaca   300
ccaacacact cgagtctttc aagactgcag ataagaagct ccttttggaa caagcagcaa   360
atgagatatg ggaatccata aaatcaggca ctgctcttga aaaccctgta ctcctcaaca   420
agttcctcct cttgacattt gcagatctaa agaagtacca cttctactat tggttttgct   480
atcctgccct ctgtcttcca gagagtttac ctctcattca ggggccagtg ggtttggatc   540
aaaggttttc actaaaacag attgaagcac tagagtgtgc atatgataat ctttgtcaaa   600
cagaaggagt cacagctctt ccttacttct aatcaagta tgatgagaac atggtgctgg   660
tttccttgct taaacactac agtgatttct tccaaggtca aaggacgaag ataacaattg   720
gtgtatatga tccctgtaac ttagcccagt accctggatg gcctttgagg aatttttttgg   780 tcctagcagc ccacagatgg agtagcagtt ccagtctgt tgaagttgtt tgcttccgtg   840
accgtaccat gcagggggcg agagacgttg cccacagcat catcttcgaa gtgaagcttc   900
cagaaatggc atttagccca gattgtccta agcagttgg atgggaaaag aaccagaaag   960
gaggcatggg accaaggatg gtgaacctca gtgaatgtat ggaccctaaa aggttagctg  1020
agtcatcagt ggatctaaat ctcaaactga tgtgttggag attggttcct actttagact  1080
tggacaaggt tgtgtctgtc aaatgtctgc tgcttggagc cggcaccttg ggttgcaatg  1140
tagctaggac gttgatgggt tggggcgtga acacatcac atttgtggac aatgccaaga  1200
tctcctactc caatcctgtg aggcagcctc tctatgagtt tgaagattgc ctaggggtg  1260 gtaagcccaa ggctctggca gcagcggacc ggctccagaa atattcccc ggtgtgaatg  1320 ccagaggatt caacatgagc atacctatgc ctgggcatcc agtgaacttc tccagtgtca  1380
ctctggagca agcccgcaga gatgtggagc aactggagca gctcatcgaa gccatgatg  1440 tcgtcttcct attgatggac accagggaga gccggtggct tcctgccgtc attgctgcaa  1500
gcaagagaaa gctggtcatc aatgctgctt gggatttga cacatttgtt gtcatgagac  1560
atggtctgaa gaaaccaaag cagcaaggag ctggggactt gtgtccaaac caccctgtgg  1620
```

```
catctgctga cctcctgggc tcatcgcttt tgccaacat ccctggttac aagcttggct    1680
gctacttctg caatgatgtg gtggcccag gagattcaac cagagaccgg accttggacc    1740
agcagtgcac tgtgagtcgt ccaggactgg ccgtgattgc aggagccctg gccgtggaat    1800
tgatggtatc tgttttgcag catccagaag ggggctatgc cattgccagc agcagtgacg    1860
atcggatgaa tgagcctcca acctctcttg ggcttgtgcc tcaccaggtt cttgatcaat    1920
atgaacgaga aggatttaac ttcctagcca aggtgtttaa ttcttcacat tccttcttag    1980
aagacttgac tggtcttaca ttgctgcatc aagaaaccca agctgctgag atctgggaca    2040
tgagcgatga tgagaccatc tgagatggcc ccgctgtggg gctgacttct ccctggccgc    2100
ctgctgagga gctctccatc gccagagcag gactgctgac cccaggcctg gtgattctgg    2160
gcccctcctc catacccga ggtctgggat tcccccctct gctgcccagg agtggccagt    2220
gttcggcgtt gctcgggatt caagatacca ccagttcaga gctaaataat aaccttggcc    2280
ttggccttgc tattgacctg ggaaaaaaaa aaaaaaaaaa aaaaa              2326
```

<210> SEQ ID NO 22
<211> LENGTH: 676
<212> TYPE: PRT
<213> ORGANISM: Homo sapiens
<220> FEATURE:
<221> NAME/KEY: MISC_FEATURE
<223> OTHER INFORMATION: GenBank Accession No.: AAH000091

<400> SEQUENCE: 22

```
Met Ala Ala Ala Thr Gly Asp Pro Gly Leu Ser Lys Leu Gln Phe Ala
1               5                   10                  15

Pro Phe Ser Ser Ala Leu Asp Val Gly Phe Trp His Glu Leu Thr Gln
            20                  25                  30

Lys Lys Leu Asn Glu Tyr Arg Leu Asp Glu Ala Pro Lys Asp Ile Lys
        35                  40                  45

Gly Tyr Tyr Tyr Asn Gly Asp Ser Ala Gly Leu Pro Ala Arg Leu Thr
    50                  55                  60

Leu Glu Phe Ser Ala Phe Asp Met Ser Ala Pro Thr Pro Ala Arg Cys
65                  70                  75                  80

Cys Pro Ala Ile Gly Thr Leu Tyr Asn Thr Asn Thr Leu Glu Ser Phe
                85                  90                  95

Lys Thr Ala Asp Lys Lys Leu Leu Glu Gln Ala Ala Asn Glu Ile
            100                 105                 110

Trp Glu Ser Ile Lys Ser Gly Thr Ala Leu Glu Asn Pro Val Leu Leu
        115                 120                 125

Asn Lys Phe Leu Leu Thr Phe Ala Asp Leu Lys Lys Tyr His Phe
    130                 135                 140

Tyr Tyr Trp Phe Cys Tyr Pro Ala Leu Cys Leu Pro Glu Ser Leu Pro
145                 150                 155                 160

Leu Ile Gln Gly Pro Val Gly Leu Asp Gln Arg Phe Ser Leu Lys Gln
                165                 170                 175

Ile Glu Ala Leu Glu Cys Ala Tyr Asp Asn Leu Cys Gln Thr Glu Gly
            180                 185                 190

Val Thr Ala Leu Pro Tyr Phe Leu Ile Lys Tyr Asp Glu Asn Met Val
        195                 200                 205

Leu Val Ser Leu Leu Lys His Tyr Ser Asp Phe Phe Gln Gly Gln Arg
    210                 215                 220

Thr Lys Ile Thr Ile Gly Val Tyr Asp Pro Cys Asn Leu Ala Gln Tyr
```

```
            225                 230                 235                 240
Pro Gly Trp Pro Leu Arg Asn Phe Leu Val Leu Ala Ala His Arg Trp
            245                 250                 255
Ser Ser Ser Phe Gln Ser Val Glu Val Val Cys Phe Arg Asp Arg Thr
            260                 265                 270
Met Gln Gly Ala Arg Asp Val Ala His Ser Ile Ile Phe Glu Val Lys
            275                 280                 285
Leu Pro Glu Met Ala Phe Ser Pro Asp Cys Pro Lys Ala Val Gly Trp
            290                 295                 300
Glu Lys Asn Gln Lys Gly Gly Met Gly Pro Arg Met Val Asn Leu Ser
305                 310                 315                 320
Glu Cys Met Asp Pro Lys Arg Leu Ala Glu Ser Ser Val Asp Leu Asn
            325                 330                 335
Leu Lys Leu Met Cys Trp Arg Leu Val Pro Thr Leu Asp Leu Asp Lys
            340                 345                 350
Val Val Ser Val Lys Cys Leu Leu Gly Ala Gly Thr Leu Gly Cys
            355                 360                 365
Asn Val Ala Arg Thr Leu Met Gly Trp Gly Val Arg His Ile Thr Phe
            370                 375                 380
Val Asp Asn Ala Lys Ile Ser Tyr Ser Asn Pro Val Arg Gln Pro Leu
385                 390                 395                 400
Tyr Glu Phe Glu Asp Cys Leu Gly Gly Lys Pro Lys Ala Leu Ala
            405                 410                 415
Ala Ala Asp Arg Leu Gln Lys Ile Phe Pro Gly Val Asn Ala Arg Gly
            420                 425                 430
Phe Asn Met Ser Ile Pro Met Pro Gly His Pro Val Asn Phe Ser Ser
            435                 440                 445
Val Thr Leu Glu Gln Ala Arg Arg Asp Val Glu Gln Leu Glu Gln Leu
            450                 455                 460
Ile Glu Ser His Asp Val Val Phe Leu Leu Met Asp Thr Arg Glu Ser
465                 470                 475                 480
Arg Trp Leu Pro Ala Val Ile Ala Ala Ser Lys Arg Lys Leu Val Ile
            485                 490                 495
Asn Ala Ala Leu Gly Phe Asp Thr Phe Val Val Met Arg His Gly Leu
            500                 505                 510
Lys Lys Pro Lys Gln Gln Gly Ala Gly Asp Leu Cys Pro Asn His Pro
            515                 520                 525
Val Ala Ser Ala Asp Leu Leu Gly Ser Ser Leu Phe Ala Asn Ile Pro
            530                 535                 540
Gly Tyr Lys Leu Gly Cys Tyr Phe Cys Asn Asp Val Val Ala Pro Gly
545                 550                 555                 560
Asp Ser Thr Arg Asp Arg Thr Leu Asp Gln Gln Cys Thr Val Ser Arg
            565                 570                 575
Pro Gly Leu Ala Val Ile Ala Gly Ala Leu Ala Val Glu Leu Met Val
            580                 585                 590
Ser Val Leu Gln His Pro Glu Gly Gly Tyr Ala Ile Ala Ser Ser Ser
            595                 600                 605
Asp Asp Arg Met Asn Glu Pro Pro Thr Ser Leu Gly Leu Val Pro His
            610                 615                 620
Gln Val Leu Asp Gln Tyr Glu Arg Glu Gly Phe Asn Phe Leu Ala Lys
625                 630                 635                 640
Val Phe Asn Ser Ser His Ser Phe Leu Glu Asp Leu Thr Gly Leu Thr
            645                 650                 655
```

Leu Leu His Gln Glu Thr Gln Ala Ala Glu Ile Trp Asp Met Ser Asp
          660                 665                 670

Asp Glu Thr Ile
        675

<210> SEQ ID NO 23
<211> LENGTH: 1820
<212> TYPE: DNA
<213> ORGANISM: Homo sapiens
<220> FEATURE:
<221> NAME/KEY: misc_feature
<223> OTHER INFORMATION: GenBank Accession No.: NM_003905

<400> SEQUENCE: 23

| | | | | |
|---|---|---|---|---|
| agtgcgcctg | cgcgcttgtg | gagctggtgg | cggcgctccg | caggggctcg | gctgttttcc | 60 |
| gcgcggcagg | cgcggccatg | gcgcagctgg | gaaagctgct | caaggagcag | aagtacgacc | 120 |
| ggcagctgag | gttgtggggt | gatcatgggc | aagaggcttt | agaatctgct | catgtttgcc | 180 |
| taataaatgc | aacagccaca | ggaactgaaa | ttcttaaaaa | cttggtacta | ccaggtattg | 240 |
| gttcgtttac | aattattgat | ggaaatcagg | tcagcggaga | agatgctgga | aacaatttct | 300 |
| tccttcaaag | aagcagtatc | ggcaagaacc | gagctgaagc | tgccatggaa | ttcttacaag | 360 |
| aattaaaatag | cgatgtctct | ggaagttttg | tggaagagag | tccagaaaac | cttctagaca | 420 |
| atgatccctc | attttttctgt | aggtttactg | ttgtagttgc | aactcagctt | cctgaaagca | 480 |
| cttcactacg | cttagcagat | gtcctctgga | attcccagat | tcctcttttg | atctgtagga | 540 |
| catatggact | agttggttat | atgaggatca | ttataaaaga | acatccagta | atagaatctc | 600 |
| atccagataa | tgcattagag | gatctacgac | tagataagcc | atttcctgaa | ctgagagaac | 660 |
| attttcagtc | ctatgatttg | gatcatatgg | aaaaaaagga | ccacagtcat | actccatgga | 720 |
| ttgtgatcat | agctaaatat | ttagcacagt | ggtatagtga | aacaaatgga | cgaataccta | 780 |
| aaacgtataa | agaaaaagag | gacttcagag | atttgattag | acaaggaatt | ctaaaaaatg | 840 |
| aaaatgggc | tccagaagat | gaagagaatt | ttgaagaagc | tattaaaaat | gtgaacacag | 900 |
| cactaaatac | aactcagatc | ccaagcagta | ttgaagatat | atttaatgat | gatcgctgca | 960 |
| taaatatcac | caaacagact | ccatcatttt | ggattttagc | tcgtgcctta | aaggaatttg | 1020 |
| tggccaaaga | gggtcaagga | aatttacctg | ttcgaggcac | aattcctgat | atgattgcag | 1080 |
| attcaggcaa | atatataaaa | ctgcaaaacg | tttaccgtga | aaaagcaaag | aaagatgctg | 1140 |
| ccgctgtggg | taatcatgtt | gccaaattgc | tgcagtccat | tggccaggca | ccagagtcca | 1200 |
| tttcagagaa | agaattaaaa | ttactctgca | gcaattctgc | atttcttcga | gtggtaagat | 1260 |
| gtcgatcctt | agctgaagaa | tatggttttgg | atacaattaa | caaggatgaa | attatttcta | 1320 |
| gcatggacaa | tccagataat | gaaatagtgt | tgtacttaat | gttacgggct | gttgatagat | 1380 |
| tcataaaaca | acagggtaga | tatccaggag | tatctaacta | tcaagttgaa | gaagatatag | 1440 |
| gaaagttgaa | gtcttgtctc | actggcttcc | ttcaggaata | tggtttatct | gtaatggtga | 1500 |
| aagatgatta | tgtccacgaa | ttttgccgat | atggagctgc | tgagccacat | accattgctg | 1560 |
| cattcttggg | gggagctgct | gctcaagagg | tcatcaaaat | aatcaccaaa | caatttgtaa | 1620 |
| ttttaataa | tacttacatt | tacagtggca | tgtcacaaac | ttcagcaact | ttccagttgt | 1680 |
| agagtaagca | agcaccttaa | gtagtgtgtt | aatgattgaa | actgtaattg | ccttcgggtt | 1740 |
| gtgctttagt | ctgtaaaatt | ctaaaggaga | gctgctaaat | tgtttcttca | ataaacatttt | 1800 |
| ttctcatttg | taaaaaaaaa | | | | | 1820 |

```
<210> SEQ ID NO 24
<211> LENGTH: 534
<212> TYPE: PRT
<213> ORGANISM: Homo sapiens
<220> FEATURE:
<221> NAME/KEY: MISC_FEATURE
<223> OTHER INFORMATION: GenBank Accession No.: NP_003896

<400> SEQUENCE: 24

Met Ala Gln Leu Gly Lys Leu Leu Lys Glu Gln Lys Tyr Asp Arg Gln
1               5                   10                  15

Leu Arg Leu Trp Gly Asp His Gly Gln Glu Ala Leu Glu Ser Ala His
                20                  25                  30

Val Cys Leu Ile Asn Ala Thr Ala Thr Gly Thr Glu Ile Leu Lys Asn
        35                  40                  45

Leu Val Leu Pro Gly Ile Gly Ser Phe Thr Ile Ile Asp Gly Asn Gln
    50                  55                  60

Val Ser Gly Glu Asp Ala Gly Asn Asn Phe Phe Leu Gln Arg Ser Ser
65                  70                  75                  80

Ile Gly Lys Asn Arg Ala Glu Ala Ala Met Glu Phe Leu Gln Glu Leu
                85                  90                  95

Asn Ser Asp Val Ser Gly Ser Phe Val Glu Glu Ser Pro Glu Asn Leu
            100                 105                 110

Leu Asp Asn Asp Pro Ser Phe Phe Cys Arg Phe Thr Val Val Val Ala
        115                 120                 125

Thr Gln Leu Pro Glu Ser Thr Ser Leu Arg Leu Ala Asp Val Leu Trp
    130                 135                 140

Asn Ser Gln Ile Pro Leu Leu Ile Cys Arg Thr Tyr Gly Leu Val Gly
145                 150                 155                 160

Tyr Met Arg Ile Ile Ile Lys Glu His Pro Val Ile Glu Ser His Pro
                165                 170                 175

Asp Asn Ala Leu Glu Asp Leu Arg Leu Asp Lys Pro Phe Pro Glu Leu
            180                 185                 190

Arg Glu His Phe Gln Ser Tyr Asp Leu Asp His Met Glu Lys Lys Asp
        195                 200                 205

His Ser His Thr Pro Trp Ile Val Ile Ala Lys Tyr Leu Ala Gln
    210                 215                 220

Trp Tyr Ser Glu Thr Asn Gly Arg Ile Pro Lys Thr Tyr Lys Glu Lys
225                 230                 235                 240

Glu Asp Phe Arg Asp Leu Ile Arg Gln Gly Ile Leu Lys Asn Glu Asn
                245                 250                 255

Gly Ala Pro Glu Asp Glu Glu Asn Phe Glu Glu Ala Ile Lys Asn Val
            260                 265                 270

Asn Thr Ala Leu Asn Thr Thr Gln Ile Pro Ser Ser Ile Glu Asp Ile
        275                 280                 285

Phe Asn Asp Asp Arg Cys Ile Asn Ile Thr Lys Gln Thr Pro Ser Phe
    290                 295                 300

Trp Ile Leu Ala Arg Ala Leu Lys Glu Phe Val Ala Lys Glu Gly Gln
305                 310                 315                 320

Gly Asn Leu Pro Val Arg Gly Thr Ile Pro Asp Met Ile Ala Asp Ser
                325                 330                 335

Gly Lys Tyr Ile Lys Leu Gln Asn Val Tyr Arg Glu Lys Ala Lys Lys
            340                 345                 350

Asp Ala Ala Ala Val Gly Asn His Val Ala Lys Leu Leu Gln Ser Ile
```

```
                355                 360                 365
Gly Gln Ala Pro Glu Ser Ile Ser Glu Lys Glu Leu Lys Leu Leu Cys
    370                 375                 380

Ser Asn Ser Ala Phe Leu Arg Val Val Arg Cys Arg Ser Leu Ala Glu
385                 390                 395                 400

Glu Tyr Gly Leu Asp Thr Ile Asn Lys Asp Glu Ile Ile Ser Ser Met
                405                 410                 415

Asp Asn Pro Asp Asn Glu Ile Val Leu Tyr Leu Met Leu Arg Ala Val
            420                 425                 430

Asp Arg Phe His Lys Gln Gly Arg Tyr Pro Gly Val Ser Asn Tyr
        435                 440                 445

Gln Val Glu Glu Asp Ile Gly Lys Leu Lys Ser Cys Leu Thr Gly Phe
    450                 455                 460

Leu Gln Glu Tyr Gly Leu Ser Val Met Val Lys Asp Asp Tyr Val His
465                 470                 475                 480

Glu Phe Cys Arg Tyr Gly Ala Ala Glu Pro His Thr Ile Ala Ala Phe
                485                 490                 495

Leu Gly Gly Ala Ala Gln Glu Val Ile Lys Ile Ile Thr Lys Gln
            500                 505                 510

Phe Val Ile Phe Asn Asn Thr Tyr Ile Tyr Ser Gly Met Ser Gln Thr
        515                 520                 525

Ser Ala Thr Phe Gln Leu
    530

<210> SEQ ID NO 25
<211> LENGTH: 2458
<212> TYPE: DNA
<213> ORGANISM: Homo sapiens
<220> FEATURE:
<221> NAME/KEY: misc_feature
<223> OTHER INFORMATION: GenBank Accession No.: NM-014484

<400> SEQUENCE: 25
ttccggaaga ggtcgccatg gcttcccggg aggaggtact cgccttacaa gctgaagttg     60
cccaacgtga ggaggaattg aattcgctga agcagaagct ggcgtcggct cttttggctg    120
agcaggaacc gcagccagaa cggctggttc cggtgtcgcc gctgccgccg aaggccgctc    180
tgtcccgaga tgagattctg cgctatagcc ggcagctagt gctgcccgag ctgggcgtgc    240
acggacagct cgcgcctgggg accgcgtgcg tgctaatcgt gggctgcggt gggctcggct    300
gtccactagc gcagtacttg gcagcggccg gcgtgggccg ccttggcctt gtggactatg    360
acgtggtaga gatgagcaac ctggcccgcc aagtgctgca tggcgaggca ctggctggcc    420
aggccaaggc cttttcggcc gccgcctcgc tgcgccgcct caattcggca gtggaatgcg    480
tgccgtacac tcaggccctt acgccagcca ctgccctaga cctggtccgc cgatatgatg    540
tggtggctga ctgctcggac aacgtgccca ctcgctacct ggttaatgac gcatgtgtgc    600
tggcgggtcg gccccctcgt tctgccagtg ccttgcgctt cgagggccaa atcacagtct    660
accattatga cggtggccct tgctatcgct gcatattccc ccaaccaccc ccagcggaga    720
cagtgaccaa ctgcgcggac ggcggggtgc tcggtgtcgt taccggggtc ctgggctgcc    780
tgcaggcctt ggaagtgctg aaaatcgctg cgggtctggg ccctcttac agtggcagct    840 tgttgctctt tgatgccctg agagggcatt ccgctctat cggctgcgg agccgcaggc    900 tcgactgtgc agcttgcggg gaacggccca ctgtgactga tctgctggac tatgaagcct    960
tctgtggctc ctcagccact gataaatgcc gctccctgca actactgagc ccagaggagc    1020
```

```
gtgtttctgt caccgactat aagcgactgc tggattctgg ggcattccac ctgttgctgg   1080
acgtcaggcc tcaggtggag gtggacattt gtcgtttgcc tcatgccta cacatccctc    1140 tgaaacattt ggaacgcagg gatgcggaga gcctgaaact cttaaaagaa gcaatctggg   1200
aagagaagca gggcacacaa gaaggggctg ctgtccccat ttatgtgatt tgcaaactgg   1260
gaaatgactc acagaaagcc gtgaagatcc tccagtcctt atcagcagct caagagttag   1320 acccttaac agttcgggat gttgtggggg gcctcatggc ctgggctgcc aaaatcgatg    1380
gaacatttcc acagtactga ggtgactggt atagtctgat gagaaagatg tggattgcca   1440
taatacctca aagatacact tgtttgcatt tttcggtaat atacatagga gctggggatt   1500
ctacagtatc tgtgaatacg tggactcctt tttataagga gttttaaaaa ttgttatgta   1560
ttggatgaat gacttattaa tggattatac cgtttctgag aaccatcatt tttttttttca  1620 gcacacggag gatgtcttgg acatgtgaga tgtaacgtga caggattttg cattttaaac   1680
tgcagatcat ttacatgtcc ttattttcca cctcccccag tcaaaatgct ttctaaatca   1740
ttttcacaga ttatatactt cggatctgtt tactgttcag ttaagaaatt cttggatctt   1800 attaatatt cagatgatag aatacatcct acagaaatac atgtttaaaa tgtaaattgt    1860
tttaattatt cagaaagagg gtcattctat ttggcctttt gaattagtat caaaatgaga   1920
tttttttttt ttttttgaga tggaatctct ctctgttgcc caggctggag tgtagtggtg   1980
cgatctcagc tcactgcaac ctccgcctcc caggttcaag cgattctcct gcctcagcct   2040
cctgagtagc tgggattaca ggcgcacgcc accacgcctg gctaattttt gtattttag    2100 tacagagggg gtttcaccat gtttgtcagg ctggtctcga actcctgacc tcgtgatccg   2160
cctgcctcga cttcccagag tgctgggatt acaggcgtga gccaccacac cctcccgaga   2220 tcttaaagt taccaaaat aaaggaaacc acctttgtag tctgtcagtg tctcttataa     2280
attgctactg ttttcttaaa gttaacttca gggtccacct tatgttgcac acatatcaca   2340
tcgtttaaat tgcatactat ggtttgactt gctttggaat tttcaagtca aagtcccaac   2400
cctttgcctc tccccttta atttgccttt tctcttttga tttaatgttt tttattc       2458
```

<210> SEQ ID NO 26
<211> LENGTH: 460
<212> TYPE: PRT
<213> ORGANISM: Homo sapiens
<220> FEATURE:
<221> NAME/KEY: MISC_FEATURE
<223> OTHER INFORMATION: GenBank Accession No.: NP_055299

<400> SEQUENCE: 26

```
Met Ala Ser Arg Glu Glu Val Leu Ala Leu Gln Ala Glu Val Ala Gln
1               5                   10                  15

Arg Glu Glu Leu Asn Ser Leu Lys Gln Lys Leu Ala Ser Ala Leu
            20                  25                  30

Leu Ala Glu Gln Glu Pro Gln Pro Glu Arg Leu Val Pro Val Ser Pro
        35                  40                  45

Leu Pro Pro Lys Ala Ala Leu Ser Arg Asp Glu Ile Leu Arg Tyr Ser
    50                  55                  60

Arg Gln Leu Val Leu Pro Glu Leu Gly Val His Gly Gln Leu Arg Leu
65                  70                  75                  80

Gly Thr Ala Cys Val Leu Ile Val Gly Cys Gly Gly Leu Gly Cys Pro
                85                  90                  95

Leu Ala Gln Tyr Leu Ala Ala Ala Gly Val Gly Arg Leu Gly Leu Val
```

```
                100                 105                 110
Asp Tyr Asp Val Val Glu Met Ser Asn Leu Ala Arg Gln Val Leu His
            115                 120                 125

Gly Glu Ala Leu Ala Gly Gln Ala Lys Ala Phe Ser Ala Ala Ala Ser
130                 135                 140

Leu Arg Arg Leu Asn Ser Ala Val Glu Cys Val Pro Tyr Thr Gln Ala
145                 150                 155                 160

Leu Thr Pro Ala Thr Ala Leu Asp Leu Val Arg Arg Tyr Asp Val Val
                165                 170                 175

Ala Asp Cys Ser Asp Asn Val Pro Thr Arg Tyr Leu Val Asn Asp Ala
            180                 185                 190

Cys Val Leu Ala Gly Arg Pro Leu Val Ser Ala Ser Ala Leu Arg Phe
            195                 200                 205

Glu Gly Gln Ile Thr Val Tyr His Tyr Asp Gly Gly Pro Cys Tyr Arg
            210                 215                 220

Cys Ile Phe Pro Gln Pro Pro Ala Glu Thr Val Thr Asn Cys Ala
225                 230                 235                 240

Asp Gly Gly Val Leu Gly Val Val Thr Gly Val Leu Gly Cys Leu Gln
                245                 250                 255

Ala Leu Glu Val Leu Lys Ile Ala Ala Gly Leu Gly Pro Ser Tyr Ser
            260                 265                 270

Gly Ser Leu Leu Leu Phe Asp Ala Leu Arg Gly His Phe Arg Ser Ile
            275                 280                 285

Arg Leu Arg Ser Arg Arg Leu Asp Cys Ala Ala Cys Gly Glu Arg Pro
            290                 295                 300

Thr Val Thr Asp Leu Leu Asp Tyr Glu Ala Phe Cys Gly Ser Ser Ala
305                 310                 315                 320

Thr Asp Lys Cys Arg Ser Leu Gln Leu Leu Ser Pro Glu Glu Arg Val
                325                 330                 335

Ser Val Thr Asp Tyr Lys Arg Leu Leu Asp Ser Gly Ala Phe His Leu
            340                 345                 350

Leu Leu Asp Val Arg Pro Gln Val Glu Val Asp Ile Cys Arg Leu Pro
            355                 360                 365

His Ala Leu His Ile Pro Leu Lys His Leu Glu Arg Arg Asp Ala Glu
            370                 375                 380

Ser Leu Lys Leu Leu Lys Glu Ala Ile Trp Glu Glu Lys Gln Gly Thr
385                 390                 395                 400

Gln Glu Gly Ala Ala Val Pro Ile Tyr Val Ile Cys Lys Leu Gly Asn
                405                 410                 415

Asp Ser Gln Lys Ala Val Lys Ile Leu Gln Ser Leu Ser Ala Ala Gln
            420                 425                 430

Glu Leu Asp Pro Leu Thr Val Arg Asp Val Val Gly Gly Leu Met Ala
            435                 440                 445

Trp Ala Ala Lys Ile Asp Gly Thr Phe Pro Gln Tyr
            450                 455                 460

<210> SEQ ID NO 27
<211> LENGTH: 459
<212> TYPE: DNA
<213> ORGANISM: Homo sapiens
<220> FEATURE:
<221> NAME/KEY: misc_feature
<223> OTHER INFORMATION: GenBank Accession No.: NM_003338.1

<400> SEQUENCE: 27
```

| | |
|---|---|
| cgccatccct gacccatggc gctgaagagg attcagaaag aattgagtga tctacagcgc | 60 |
| gatccacctg ctcactgttc agctggacct gtgggagatg acttgttcca ctggcaagcc | 120 |
| actattatgg ggcctcctga tagcgcatat caaggtggag tcttctttct cactgtacat | 180 |
| tttccgacag attatccttt taaaccacca aagattgctt tcacaacaaa aatttaccat | 240 |
| ccaaacataa acagtaatgg aagtatttgt ctcgatattc tgaggtcaca atggtcacca | 300 |
| gctctgactg tatcaaaagt tttattgtcc atatgttctc tactttgtga tcctaatcca | 360 |
| gatgacccct tagtaccaga tattgcacaa atctataaat cagacaaaga aaaatacaac | 420 |
| agacatgcaa gagaatggac tcagaaatat gcaatgtaa | 459 |

<210> SEQ ID NO 28
<211> LENGTH: 147
<212> TYPE: PRT
<213> ORGANISM: Homo sapiens
<220> FEATURE:
<221> NAME/KEY: MISC_FEATURE
<223> OTHER INFORMATION: GenBank Accession No.: NP_003329.1

<400> SEQUENCE: 28

```
Met Ala Leu Lys Arg Ile Gln Lys Glu Leu Ser Asp Leu Gln Arg Asp
1               5                   10                  15
Pro Pro Ala His Cys Ser Ala Gly Pro Val Gly Asp Asp Leu Phe His
            20                  25                  30
Trp Gln Ala Thr Ile Met Gly Pro Pro Asp Ser Ala Tyr Gln Gly Gly
        35                  40                  45
Val Phe Phe Leu Thr Val His Phe Pro Thr Asp Tyr Pro Phe Lys Pro
    50                  55                  60
Pro Lys Ile Ala Phe Thr Thr Lys Ile Tyr His Pro Asn Ile Asn Ser
65                  70                  75                  80
Asn Gly Ser Ile Cys Leu Asp Ile Leu Arg Ser Gln Trp Ser Pro Ala
                85                  90                  95
Leu Thr Val Ser Lys Val Leu Leu Ser Ile Cys Ser Leu Leu Cys Asp
            100                 105                 110
Pro Asn Pro Asp Asp Pro Leu Val Pro Asp Ile Ala Gln Ile Tyr Lys
        115                 120                 125
Ser Asp Lys Glu Lys Tyr Asn Arg His Ala Arg Glu Trp Thr Gln Lys
    130                 135                 140
Tyr Ala Met
145
```

<210> SEQ ID NO 29
<211> LENGTH: 1763
<212> TYPE: DNA
<213> ORGANISM: Homo sapiens
<220> FEATURE:
<221> NAME/KEY: misc_feature
<223> OTHER INFORMATION: GenBank Accession No.: NM_022476.1

<400> SEQUENCE: 29

| | |
|---|---|
| atcaagcagg ggcagggctg gcgctgcggc gggagatgct gtcgggccgc ggcggcgctt | 60 |
| ggcagccagg agctctgcat tgaaggcact ggggtaaagt gaatgccgaa gacagaagat | 120 |
| ttggatgata caccactgac tttctttgtt tggaatacac gttatgaacc ctttctggag | 180 |
| catgtctaca agctctgtac gcaaacgatc tgaaggtgaa gagaagacat taacagggga | 240 |
| cgtgaaaacc agtcctccac gaactgcacc aaagaaacag ctgccttcta ttcccaaaaa | 300 |
| tgctttgccc ataactaagc ctacatctcc tgccccagca gcacagtcaa caaatggcac | 360 |

```
gcatgcgtcc tatggaccct tctacctgga atactctctt cttgcagaat ttaccttggt    420
tgtgaagcag aagctaccag gcgtctatgt gcagccatct tatcgctctg cattaatgtg    480
gtttggagta atattcatac ggcatggact ttaccaagat ggcgtattta agtttacagt    540
ttacatccct gataactatc cagatggtga ctgtccacgc ttggtgttcg atattcctgt    600
ctttcacccg ctagttgatc ccacctcagg tgagctggat gtgaagagag catttgcaaa    660
atggaggcgg aaccataatc atatttggca ggtattaatg tatgcaagga gagttttcta    720
caagattgat acagcaagcc ccctgaaccc agaggctgca gtactgtatg aaaaagatat    780
tcagcttttt aaaagtaaag ttgttgacag tgttaaggtg tgcactgctc gtttgtttga    840
ccaacctaaa atagaagacc cctatgcaat tagcttttct ccatggaatc cttctgtaca    900
tgatgaagcc agagaaaaga tgctgactca gaaaaagcct gaagaacagc acaataaaag    960
tgttcatgtt gctggcctgt catgggtaaa gcctggctca gtacagcctt tcagtaaaga   1020
agagaaaaca gtggcgactt aagagatggt gaatctggtg caccatgcac tttcctgcta   1080
gactctggcc tagttcaagc tgaccaatgg cagaggactg cctgaagagt aaaactgtgt   1140
gaacaatgac tgactgccag tgttttccat gtatgcatag gttctaacag cagggtttgg   1200
aaacctgtct ctaagtaatg cattacttct gtcagaagtg tcttagggtg ttatctagt    1260
tcagtactcc aaattattgg ggaccttgag gcttaagtaa gtatttttct gaatataatg   1320
ctaaaggtaa gttgcattca tttaaactaa tagagcagac agaattcagc actacttaat   1380
agtttataaa tcagtggttt cagttgtata tatgttagga aatggagagg tatagagaga   1440
gcaggttcca tagctcagca cttttaagtg gaagatcatt tgaatctcag tcttcagcct   1500
gcactgattt gtagcctgca ctgtcttact gatttacaaa ctgaaatcac tgagaaatgt   1560
ctttagttca gtgagaagaa accagaacac ttgttcctag tgttgtgttg ttttttttaa   1620
gcaaattact tactgtattt ttatggcagg agggagaaaa agtgttacaa cggcttctaa   1680
tgaagtccgg tatttaaatg ataaatgact aatgtgttta gtagagacaa aataaaccaa   1740
taaatgattg ttctttgcca ttt                                          1763
```

<210> SEQ ID NO 30
<211> LENGTH: 292
<212> TYPE: PRT
<213> ORGANISM: Homo sapiens
<220> FEATURE:
<221> NAME/KEY: MISC_FEATURE
<223> OTHER INFORMATION: GenBank Accession No.: NP_071921.1

<400> SEQUENCE: 30

```
Met Asn Pro Phe Trp Ser Met Ser Thr Ser Ser Val Arg Lys Arg Ser
1               5                   10                  15

Glu Gly Glu Glu Lys Thr Leu Thr Gly Asp Val Lys Thr Ser Pro Pro
            20                  25                  30

Arg Thr Ala Pro Lys Lys Gln Leu Pro Ser Ile Pro Lys Asn Ala Leu
        35                  40                  45

Pro Ile Thr Lys Pro Thr Ser Pro Ala Pro Ala Ala Gln Ser Thr Asn
    50                  55                  60

Gly Thr His Ala Ser Tyr Gly Pro Phe Tyr Leu Glu Tyr Ser Leu Leu
65                  70                  75                  80

Ala Glu Phe Thr Leu Val Val Lys Gln Lys Leu Pro Gly Val Tyr Val
                85                  90                  95

Gln Pro Ser Tyr Arg Ser Ala Leu Met Trp Phe Gly Val Ile Phe Ile
```

|   |   |   | 100 |   |   |   | 105 |   |   |   | 110 |   |   |
|---|---|---|---|---|---|---|---|---|---|---|---|---|---|
| Arg | His | Gly | Leu | Tyr | Gln | Asp | Gly | Val | Phe | Lys | Phe | Thr | Val | Tyr | Ile |
|   |   |   | 115 |   |   |   |   | 120 |   |   |   |   | 125 |

Pro Asp Asn Tyr Pro Asp Gly Asp Cys Pro Arg Leu Val Phe Asp Ile
    130                 135                 140

Pro Val Phe His Pro Leu Val Asp Pro Thr Ser Gly Glu Leu Asp Val
145                 150                 155                 160

Lys Arg Ala Phe Ala Lys Trp Arg Arg Asn His Asn His Ile Trp Gln
            165                 170                 175

Val Leu Met Tyr Ala Arg Arg Val Phe Tyr Lys Ile Asp Thr Ala Ser
        180                 185                 190

Pro Leu Asn Pro Glu Ala Ala Val Leu Tyr Glu Lys Asp Ile Gln Leu
        195                 200                 205

Phe Lys Ser Lys Val Val Asp Ser Val Lys Val Cys Thr Ala Arg Leu
210                 215                 220

Phe Asp Gln Pro Lys Ile Glu Asp Pro Tyr Ala Ile Ser Phe Ser Pro
225                 230                 235                 240

Trp Asn Pro Ser Val His Asp Glu Ala Arg Glu Lys Met Leu Thr Gln
            245                 250                 255

Lys Lys Pro Glu Glu Gln His Asn Lys Ser Val His Val Ala Gly Leu
        260                 265                 270

Ser Trp Val Lys Pro Gly Ser Val Gln Pro Phe Ser Lys Glu Glu Lys
        275                 280                 285

Thr Val Ala Thr
        290

<210> SEQ ID NO 31
<211> LENGTH: 1354
<212> TYPE: DNA
<213> ORGANISM: Homo sapiens
<220> FEATURE:
<221> NAME/KEY: misc_feature
<223> OTHER INFORMATION: GenBank Accession No.: BC004862.1

<400> SEQUENCE: 31

| ggcacgaggg | gaggaccccg | ggcgggccca | cgggccgtgt | ggggcctggt | ccggcccgcc | 60 |
| gggtgtgtga | agaccggggc | ccggtgctgc | ccggccggag | ggcgagcgga | ggggaggggc | 120 |
| ctggtccggc | ccggccggtg | cgtgaggact | ggggcccggg | cccggcgccg | ccgccgccgc | 180 |
| cgccgccgcg | atggcccagc | agcagatgac | cagctcgcag | aaggccctga | tgctcgagct | 240 |
| gaaatccctg | caggaggaac | cggtggaggg | cttccggatc | accctggtgg | acgagtccga | 300 |
| cctctacaac | tggaggtgg | ccatcttcgg | accccccaac | accctctacg | aaggcggcta | 360 |
| cttcaaggcg | catattaaat | ttcctattga | ctaccccctat | tcaccaccta | ccttcagatt | 420 |
| cttgaccaaa | atgtggcacc | ccaacattta | tgagaatgga | gatgtatgca | tttcgattct | 480 |
| tcatccgcct | gtagatgacc | cacagagtgg | agaactgcct | tctgaaaggt | ggaatcctac | 540 |
| tcagaatgtg | aggactatcc | tattaagtgt | aatctcactg | cttaatgagc | ccaacacctt | 600 |
| ctccccagcc | aatgtcgatg | cttcagttat | gttcaggaaa | tggagagaca | gtaaaggaaa | 660 |
| agacaaagaa | tatgctgaaa | ttattaggaa | acaagtttca | gccactaagg | ccgaagcaga | 720 |
| aaaggatgga | gtgaaggtcc | ccacaaccct | ggcggaatac | tgcatcaaaa | ctaaagtgcc | 780 |
| ttccaatgac | aacagctcag | atttgcttta | cgacgacttg | tatgatgacg | acattgatga | 840 |
| tgaagatgag | gaggaggaag | atgccgactg | ttatgatgat | gatgattctg | ggaatgagga | 900 |

```
gtcgtgacgt gctccttcag tgcccctgta ctgccctgcc atctcaggcc aaagggaggg    960
gagcaagtgg ggacctggcc atggcccctc agcaaaaacc tattcacagc gggtggggaa   1020
acacacacag ctcctgctga ctcccttat ggatctcagt ttgctccttt ttatggacct   1080
ttaatggaga gagagtaacc ctccacagaa tgtctgaatt cttgcattct ttaccctcc    1140 atcactatat tgattctttt tttaaaaaac atgaacccaa actcccgcct cacttcgtct   1200
ctacagaatg ttcacagcaa aacacgtttg gtctgttttt agattcttga agaattcaat   1260
agtctttcaa gatgtttaat gtgtttaaag ctgggaacct gttgggagtt cacaagtgct   1320
gcatatactg ggtagcaaaa aaaaaaaaaa aaaa                                1354
```

<210> SEQ ID NO 32
<211> LENGTH: 238
<212> TYPE: PRT
<213> ORGANISM: Homo sapiens
<220> FEATURE:
<221> NAME/KEY: MISC_FEATURE
<223> OTHER INFORMATION: GenBank Accession No.: AAH04862.1

<400> SEQUENCE: 32

```
Met Ala Gln Gln Gln Met Thr Ser Ser Gln Lys Ala Leu Met Leu Glu
1               5                   10                  15

Leu Lys Ser Leu Gln Glu Glu Pro Val Glu Gly Phe Arg Ile Thr Leu
            20                  25                  30

Val Asp Glu Ser Asp Leu Tyr Asn Trp Glu Val Ala Ile Phe Gly Pro
        35                  40                  45

Pro Asn Thr Leu Tyr Glu Gly Gly Tyr Phe Lys Ala His Ile Lys Phe
    50                  55                  60

Pro Ile Asp Tyr Pro Tyr Ser Pro Pro Thr Phe Arg Phe Leu Thr Lys
65                  70                  75                  80

Met Trp His Pro Asn Ile Tyr Glu Asn Gly Asp Val Cys Ile Ser Ile
                85                  90                  95

Leu His Pro Pro Val Asp Asp Pro Gln Ser Gly Glu Leu Pro Ser Glu
            100                 105                 110

Arg Trp Asn Pro Thr Gln Asn Val Arg Thr Ile Leu Leu Ser Val Ile
        115                 120                 125

Ser Leu Leu Asn Glu Pro Asn Thr Phe Ser Pro Ala Asn Val Asp Ala
    130                 135                 140

Ser Val Met Phe Arg Lys Trp Arg Asp Ser Lys Gly Lys Asp Lys Glu
145                 150                 155                 160

Tyr Ala Glu Ile Ile Arg Lys Gln Val Ser Ala Thr Lys Ala Glu Ala
                165                 170                 175

Glu Lys Asp Gly Val Lys Val Pro Thr Thr Leu Ala Glu Tyr Cys Ile
            180                 185                 190

Lys Thr Lys Val Pro Ser Asn Asp Asn Ser Ser Asp Leu Leu Tyr Asp
        195                 200                 205

Asp Leu Tyr Asp Asp Asp Ile Asp Asp Glu Asp Glu Glu Glu Glu Asp
    210                 215                 220

Ala Asp Cys Tyr Asp Asp Asp Ser Gly Asn Glu Glu Ser
225                 230                 235
```

<210> SEQ ID NO 33
<211> LENGTH: 881
<212> TYPE: DNA
<213> ORGANISM: Homo sapiens
<220> FEATURE:
<221> NAME/KEY: misc_feature
<223> OTHER INFORMATION: GenBank Accession No.: XM_054332.1

<400> SEQUENCE: 33

```
ggcggaccga agaacgcagg aaggggggccg ggggggacccg ccccccggccg gccgcagcca    60
tgaactccaa cgtggagaac ctaccccgc acatcatccg cctggtgtac aaggaggtga      120
cgacactgac cgcagaccca cccgatggca tcaaggtctt tcccaacgag gaggacctca      180
ccgacctcca ggtcaccatc gagggccctg aggggacccc atatgctgga ggtctgttcc      240
gcatgaaact cctgctgggg aaggacttcc ctgcctcccc acccaagggc tacttcctga      300
ccaagatctt ccacccgaac gtgggcgcca atggcgagat ctgcgtcaac gtgctcaaga      360
gggactggac ggctgagctg ggcatccgac acgtactgct gaccatcaag tgcctgctga      420
tccacccctaa ccccgagtct gcactcaacg aggaggcggg ccgcctgctc ttggagaact      480
acgaggagta tgcggctcgg gcccgtctgc tcacagagat ccacggggggc gccggcgggc      540
ccagcggcag ggccgaagcc ggtcgggccc tggccagtgg cactgaagct tcctccaccg      600
accctggggc cccaggggggc ccgggagggg ctgagggtcc catggccaag aagcatgctg      660
gcgagcgcga taagaagctg gcggccaaga aaaagacgga caagaagcgg gcgctgcggc      720
ggctgtagtg ggctctcttc ctccttccac cgtgacccca acctctcctg tccccctccct    780
ccaactctgt ctctaagtta tttaaattat ggctggggtc ggggagggta caggggggcac      840
tgggacctgg atttgttttt ctaaataaag ttggaaaagc a                           881
```

<210> SEQ ID NO 34
<211> LENGTH: 222
<212> TYPE: PRT
<213> ORGANISM: Homo sapiens
<220> FEATURE:
<221> NAME/KEY: MISC_FEATURE
<223> OTHER INFORMATION: GenBank Accession No.: XP_054332.1

<400> SEQUENCE: 34

```
Met Asn Ser Asn Val Glu Asn Leu Pro Pro His Ile Ile Arg Leu Val
1               5                   10                  15

Tyr Lys Glu Val Thr Thr Leu Thr Ala Asp Pro Pro Asp Gly Ile Lys
            20                  25                  30

Val Phe Pro Asn Glu Glu Asp Leu Thr Asp Leu Gln Val Thr Ile Glu
        35                  40                  45

Gly Pro Glu Gly Thr Pro Tyr Ala Gly Gly Leu Phe Arg Met Lys Leu
    50                  55                  60

Leu Leu Gly Lys Asp Phe Pro Ala Ser Pro Pro Lys Gly Tyr Phe Leu
65                  70                  75                  80

Thr Lys Ile Phe His Pro Asn Val Gly Ala Asn Gly Glu Ile Cys Val
                85                  90                  95

Asn Val Leu Lys Arg Asp Trp Thr Ala Glu Leu Gly Ile Arg His Val
            100                 105                 110

Leu Leu Thr Ile Lys Cys Leu Leu Ile His Pro Asn Pro Glu Ser Ala
        115                 120                 125

Leu Asn Glu Glu Ala Gly Arg Leu Leu Leu Glu Asn Tyr Glu Glu Tyr
    130                 135                 140

Ala Ala Arg Ala Arg Leu Leu Thr Glu Ile His Gly Ala Gly Gly
145                 150                 155                 160

Pro Ser Gly Arg Ala Glu Ala Gly Arg Ala Leu Ala Ser Gly Thr Glu
                165                 170                 175

Ala Ser Ser Thr Asp Pro Gly Ala Pro Gly Gly Pro Gly Gly Ala Glu
```

```
                  180                 185                 190
Gly Pro Met Ala Lys Lys His Ala Gly Glu Arg Asp Lys Lys Leu Ala
            195                 200                 205
Ala Lys Lys Lys Thr Asp Lys Lys Arg Ala Leu Arg Arg Leu
    210                 215                 220

<210> SEQ ID NO 35
<211> LENGTH: 1579
<212> TYPE: DNA
<213> ORGANISM: Homo sapiens
<220> FEATURE:
<221> NAME/KEY: misc_feature
<223> OTHER INFORMATION: GenBank Accession No.: NM_003344.1

<400> SEQUENCE: 35
ccgggccgtg acagacggcc ggcagaggaa gggagagagg cggcggcgac accatgtcat      60
ctcccagtcc gggcaagagg cggatggaca cggacgtggt caagctcatc gagagtaaac     120
atgaggttac gatcctggga ggacttaatg aatttgtagt gaagtttat ggaccacaag      180 gaacaccata tgaaggcgga gtatggaaag ttagagtgga cctacctgat aaatacccctt    240 tcaaatctcc atctatagga ttcatgaata aaattttcca tcccaacatt gatgaagcgt     300
caggaactgt gtgtctagat gtaattaatc aaacttggac agctctctat gatcttacca     360
atatatttga gtccttcctg cctcagttat tggcctatcc taaccccata gatcctctca     420
atggtgacgc tgcagccatg tacctccacc gaccagaaga atacaagcag aaaattaaag     480
agtacatcca gaaatacgcc acggaggagg cgctgaaaga acaggaagag ggtaccgggg     540
acagctcatc ggagagctct atgtctgact tttccgaaga tgaggcccag gatatggagt     600
tgtagtagaa aaagcacctg cttttcagaa agactattat ttcctaacca tgagaagcag     660
actataatat tcatatttaa acaaagcaat ttttttatt actaaacaag gttttatga      720 ataatagcat tgatatatat atattatata tcaccctta gatcttgatt tcttggtcat      780
ttctcaacct gaggtgcata gcatattccc acattccatt tggtagcaat atgcggtctg    840
aatgcatgca ttcatgagtc catgtggcca agtcagcctg tgtgctactg aactgtcgaa     900
ggaaatagcc gctctgatag gtagatgtga gtaaaagaa caggaaaaaa ttgcttcttt     960
tattggtttc caaagaaaca aaccaaacca accagctctt ggatgtgaag ataaaatagt    1020
gcttttttga aatggagagg aaaaacttgg ggaggaagag gcctgctgtg ggggcatcgg    1080
agccagccat gtaagaatca gagctgctcc ttcctgtgaa tcctaggtgg ccctatgtct    1140
tctgtggagt tacagtataa agcagggagc taattaagag tattaaaact taaaaccatt    1200
ttttgactct gattttaagt acattttat atgtcagttg ctgcccttca cactaccagg     1260
ccctgcagcc acagtgttct gttggagaaa cttggggaag tgttttctga accagttctt    1320
tttcttgggg tagagcgtga aatccagacc tgttttgaa aggacagcac aggaggagaa     1380
aagtgactgg gacgatgctt cctctcatcc aaaacacatg cagagtcaca tcctcatcct    1440
agtgtttggc agtttgagac cgctaccctg aacttaagag cttaaatat gagggttgtg    1500 tttctggggg ggttattttt ttggtgtgtg tgtgtgtgta ttgtgcttag aaaggttgca    1560
gatttcatct tcacctacc                                                 1579

<210> SEQ ID NO 36
<211> LENGTH: 183
<212> TYPE: PRT
<213> ORGANISM: Homo sapiens
<220> FEATURE:
```

<221> NAME/KEY: MISC_FEATURE
<223> OTHER INFORMATION: GenBank Accession No.: NP_003335.1

<400> SEQUENCE: 36

Met Ser Ser Pro Ser Pro Gly Lys Arg Arg Met Asp Thr Asp Val Val
1               5                   10                  15

Lys Leu Ile Glu Ser Lys His Glu Val Thr Ile Leu Gly Gly Leu Asn
            20                  25                  30

Glu Phe Val Val Lys Phe Tyr Gly Pro Gln Gly Thr Pro Tyr Glu Gly
        35                  40                  45

Gly Val Trp Lys Val Arg Val Asp Leu Pro Asp Lys Tyr Pro Phe Lys
    50                  55                  60

Ser Pro Ser Ile Gly Phe Met Asn Lys Ile Phe His Pro Asn Ile Asp
65                  70                  75                  80

Glu Ala Ser Gly Thr Val Cys Leu Asp Val Ile Asn Gln Thr Trp Thr
                85                  90                  95

Ala Leu Tyr Asp Leu Thr Asn Ile Phe Glu Ser Phe Leu Pro Gln Leu
            100                 105                 110

Leu Ala Tyr Pro Asn Pro Ile Asp Pro Leu Asn Gly Asp Ala Ala Ala
        115                 120                 125

Met Tyr Leu His Arg Pro Glu Glu Tyr Lys Gln Lys Ile Lys Glu Tyr
    130                 135                 140

Ile Gln Lys Tyr Ala Thr Glu Glu Ala Leu Lys Glu Gln Glu Glu Gly
145                 150                 155                 160

Thr Gly Asp Ser Ser Ser Glu Ser Ser Met Ser Asp Phe Ser Glu Asp
                165                 170                 175

Glu Ala Gln Asp Met Glu Leu
            180

<210> SEQ ID NO 37
<211> LENGTH: 582
<212> TYPE: DNA
<213> ORGANISM: Homo sapiens
<220> FEATURE:
<221> NAME/KEY: misc_feature
<223> OTHER INFORMATION: GenBank Accession No.: NM_003341.1

<400> SEQUENCE: 37
atgtcggatg acgattcgag ggccagcacc agctcctcct catcttcgtc ctccaaccag      60
caaaccgaga agaaacaaa caccccaag aagaaggaga gtaaagtcag catgagcaaa       120
aactccaaac tcctctccac cagcgccaag agaattcaga aggagctggc ggacatcact    180
ttagaccctc cacctaattg cagtgctggt cccaaaggcg ataacatcta tgaatggaga    240
tcaaccattc tagggcctcc aggatccgtg tatgagggtg tgtattctt tctcgatatc     300 acttttacac cagaatatcc cttcaagcct ccaaaggtta catttcggac aagaatctat    360
cattgtaata ttaacagtca aggtgttatt tgcttggaca tattgaaaga taattggagt    420
ccagcactaa ccatttctaa agtcctcctt tctatctgct cacttcttac agactgtaat    480
cctgccgacc ccttggtggg aagtattgcc actcagtata tgaccaacag agcagaacat    540
gacagaatgg ccagacagtg gaccaagaga tacgctacat aa                       582

<210> SEQ ID NO 38
<211> LENGTH: 193
<212> TYPE: PRT
<213> ORGANISM: Homo sapiens
<220> FEATURE:
<221> NAME/KEY: MISC_FEATURE
<223> OTHER INFORMATION: GenBank Accession No.: NP_003332.1

<400> SEQUENCE: 38

```
Met Ser Asp Asp Ser Arg Ala Ser Thr Ser Ser Ser Ser Ser
1               5                   10                  15

Ser Ser Asn Gln Gln Thr Glu Lys Glu Thr Asn Thr Pro Lys Lys Lys
            20                  25                  30

Glu Ser Lys Val Ser Met Ser Lys Asn Ser Lys Leu Leu Ser Thr Ser
        35                  40                  45

Ala Lys Arg Ile Gln Lys Glu Leu Ala Asp Ile Thr Leu Asp Pro Pro
    50                  55                  60

Pro Asn Cys Ser Ala Gly Pro Lys Gly Asp Asn Ile Tyr Glu Trp Arg
65                  70                  75                  80

Ser Thr Ile Leu Gly Pro Pro Gly Ser Val Tyr Glu Gly Gly Val Phe
                85                  90                  95

Phe Leu Asp Ile Thr Phe Thr Pro Glu Tyr Pro Phe Lys Pro Pro Lys
                100                 105                 110

Val Thr Phe Arg Thr Arg Ile Tyr His Cys Asn Ile Asn Ser Gln Gly
            115                 120                 125

Val Ile Cys Leu Asp Ile Leu Lys Asp Asn Trp Ser Pro Ala Leu Thr
130                 135                 140

Ile Ser Lys Val Leu Leu Ser Ile Cys Ser Leu Leu Thr Asp Cys Asn
145                 150                 155                 160

Pro Ala Asp Pro Leu Val Gly Ser Ile Ala Thr Gln Tyr Met Thr Asn
                165                 170                 175

Arg Ala Glu His Asp Arg Met Ala Arg Gln Trp Thr Lys Arg Tyr Ala
            180                 185                 190

Thr
```

<210> SEQ ID NO 39
<211> LENGTH: 1743
<212> TYPE: DNA
<213> ORGANISM: Homo sapiens
<220> FEATURE:
<221> NAME/KEY: misc_feature
<223> OTHER INFORMATION: GenBank Accession No.: NM_003336.1

<400> SEQUENCE: 39

| | | | | | |
|---|---|---|---|---|---|
| gcggttcctc | tgggtgcttc | cgcctcccct | tctcctgctt | ctccagcctc | ttcggcctcc | 60 |
| tcgcccgccg | cgggaacccg | agaccccagt | gtatgcccca | ccctgaccc | cgctcgcgac | 120 |
| atgtccaccc | cggctcggcg | gcgcctcatg | cgggacttca | agaggttgca | ggaggatcct | 180 |
| ccagccggag | tcagcggggc | tccgtccgag | aacaacataa | tggtgtggaa | cgcggtcatt | 240 |
| ttcgggcctg | aagggacccc | gtttggggat | ggaacattta | aacttacaat | agaattcact | 300 |
| gaagaatatc | caaataaacc | acctacagtt | agatttgtct | ctaagatgtt | ccatccaaat | 360 |
| gtctatgcag | atggtagtat | atgtctggac | atacttcaga | accgttggag | tccaacctat | 420 |
| gatgtgtctt | ccattctaac | atccatacag | tctctgttgg | atgaacccaa | tcccaatagt | 480 |
| ccagcaaaca | gccaggctgc | tcagctgtac | caggagaaca | acgggaata | tgaaaagcgt | 540 |
| gtttctgcaa | tagtagaaca | aagctggcgt | gattgttgac | cccgggtaca | gtttaaagaa | 600 |
| gctggccata | agaaaaatat | atattgatgt | gtttgtcacc | tccctactcc | tgtcattaca | 660 |
| tttactttat | taaagcaaa | ataactgttg | tgctgtttcc | atcttccttg | ccaagttttc | 720 |
| ctaccccttc | taccctctcc | ttaaacatca | gaaaacaccc | tctatgaaat | caaatgtact | 780 |

-continued

```
gtacctgggt tacttgcaaa aattactaat gcttcagttt ttctgttgta tttcatttcc    840
agttttcagg cagttatttt tattattgta ctttaagctt ttaagatgaa ttgttataca    900
agaggtgctt atgcttagct tgatgaccag gatgttattt ttaacaaaat gattgctgaa    960
gtgtttcatc ctggctggtc cttcacttgt gttggattta gaagtgaatg tgtttggaat   1020
atggcctaca gagaatagaa acaaatccat gtaaacaatt ttgaaggagg catgggagct   1080
aaaaatcctg tgatactaag atctcagtca tatgaattac aacgtagtat ttactggcaa   1140
gaaggagaaa gttgaaggac tcagctaaag gagtacagca attgtagtaa ctgacacatc   1200
ctctctttgc aagctgctga ctgggcacac tcatgccaag tttcagaatt attggtcttc   1260
tgggtttttg cttttaaaa gaggtgtggg agcagaggaa tggaaacaat cgtgagtttt     1320
tgagctaggg aaagttggag ctcctttaat cttttaaag gatcagtgct gccctaagtg     1380
aataaactca attgtccatc tttattttag agttttaatg aattcaagga agggagcata   1440
gcatatctgt ggcaaactat tttccactca aatcctgagt tattgctgca tgctttaatt   1500
tcttcccttt cagcatctga gaaccttaaa gccaatgtct gcgatctttt tttggatatt   1560 tatacttta gatatatagt acctttaagt agcagtatgg gacaaggctt gtaaatgttt     1620
tgtctaatgt tctattgtca ccttttatgc atttatcact tccaaatcta actttgcaca   1680
agtaacccat gtaaaaaaaa atgtacattt ttcaaaagtt gtaataaaa ataaccttaa     1740 aaa                                                                  1743
```

<210> SEQ ID NO 40
<211> LENGTH: 152
<212> TYPE: PRT
<213> ORGANISM: Homo sapiens
<220> FEATURE:
<221> NAME/KEY: MISC_FEATURE
<223> OTHER INFORMATION: GenBank Accession No.: NP_003327.1

<400> SEQUENCE: 40

```
Met Ser Thr Pro Ala Arg Arg Leu Met Arg Asp Phe Lys Arg Leu
1               5                   10                  15

Gln Glu Asp Pro Pro Ala Gly Val Ser Gly Ala Pro Ser Glu Asn Asn
            20                  25                  30

Ile Met Val Trp Asn Ala Val Ile Phe Gly Pro Glu Gly Thr Pro Phe
        35                  40                  45

Gly Asp Gly Thr Phe Lys Leu Thr Ile Glu Phe Thr Glu Glu Tyr Pro
    50                  55                  60

Asn Lys Pro Pro Thr Val Arg Phe Val Ser Lys Met Phe His Pro Asn
65                  70                  75                  80

Val Tyr Ala Asp Gly Ser Ile Cys Leu Asp Ile Leu Gln Asn Arg Trp
                85                  90                  95

Ser Pro Thr Tyr Asp Val Ser Ser Ile Leu Thr Ser Ile Gln Ser Leu
            100                 105                 110

Leu Asp Glu Pro Asn Pro Asn Ser Pro Ala Asn Ser Gln Ala Ala Gln
        115                 120                 125

Leu Tyr Gln Glu Asn Lys Arg Glu Tyr Glu Lys Arg Val Ser Ala Ile
    130                 135                 140

Val Glu Gln Ser Trp Arg Asp Cys
145                 150
```

<210> SEQ ID NO 41
<211> LENGTH: 1294
<212> TYPE: DNA

<213> ORGANISM: Homo sapiens
<220> FEATURE:
<221> NAME/KEY: misc_feature
<223> OTHER INFORMATION: GenBank Accession No.: NM_006357.1

<400> SEQUENCE: 41

```
cccacagctg cctccatttc cttaaggaag ggttttttc tctctccctc ccccacaccg     60
tagcggcgcg cgagcggccg ggcgggcggc cgagttttcc aagagataac ttcaccaaga   120
tgtccagtga taggcaaagg tccgatgatg agagccccag caccagcagt ggcagttcag   180
atgcggacca gcgagaccca gccgctccag agcctgaaga acaagaggaa agaaaacctt   240
ctgccaccca gcagaagaaa aacaccaaac tctctagcaa aaccactgct aagttatcca   300
ctagtgctaa aagaattcag aaggagctag ctgaaataac ccttgatcct cctcctaatt   360
gcagtgctgg gcctaaagga gataacattt atgaatggag atcaactata cttggtccac   420
cgggttctgt atatgaaggt ggtgtgtttt ttctggatat cacattttca tcagattatc   480
catttaagcc accaaaggtt actttccgca ccagaatcta tcactgcaac atcaacagtc   540
agggagtcat ctgtctggac atccttaaag acaactggag tcccgctttg actatttcaa   600
aggttttgct gtctatttgt tccctttga cagactgcaa ccctgcggat cctctggttg   660
gaagcatagc cactcagtat ttgaccaaca gagcagaaca cgacaggata gccagacagt   720
ggaccaagag atacgcaaca taattcacat aatttgtatg cagtgtgaag gagcagaagg   780
catcttctca ctgtgctgca aatctttata gcctttacaa tacggacttc tgtgtatatg   840
ttatactgat tctactctgc ttttatcctt tggagcctgg gagactcccc aaaaaggtaa   900
atgctatcaa gagtagaact ttgtagctgt agattagtta tgtttaaaac gcctacttgc   960
aagtcttgct tctttgggat atcaaaatgt attttgtgat gtactaagga tactggtcct  1020
gaagtctacc aaatattata gtgcatttta gcctaattca ttatctgtat gaagttataa  1080
aagtagctgt agatggctag gaattatgtc atttgtatta aacccagatc tatttctgag  1140
tatgtggttc atgctgttgt gaaaaatgtt ttacctttta cctttgtcag tttgtaatga  1200
gaggatttcc ttttacccctt tgtagctcag agagcacctg atgtatcatc tcaaacacaa  1260
taaacatgct cctgaaggaa aaaaaaaaaa aaaa                               1294
```

<210> SEQ ID NO 42
<211> LENGTH: 207
<212> TYPE: PRT
<213> ORGANISM: Homo sapiens
<220> FEATURE:
<221> NAME/KEY: MISC_FEATURE
<223> OTHER INFORMATION: GenBank Accession No.: NP_006348.1

<400> SEQUENCE: 42

```
Met Ser Ser Asp Arg Gln Arg Ser Asp Asp Glu Ser Pro Ser Thr Ser
1               5                   10                  15

Ser Gly Ser Ser Asp Ala Asp Gln Arg Asp Pro Ala Ala Pro Glu Pro
            20                  25                  30

Glu Glu Gln Glu Glu Arg Lys Pro Ser Ala Thr Gln Gln Lys Lys Asn
        35                  40                  45

Thr Lys Leu Ser Ser Lys Thr Thr Ala Lys Leu Ser Thr Ser Ala Lys
    50                  55                  60

Arg Ile Gln Lys Glu Leu Ala Glu Ile Thr Leu Asp Pro Pro Pro Asn
65                  70                  75                  80

Cys Ser Ala Gly Pro Lys Gly Asp Asn Ile Tyr Glu Trp Arg Ser Thr
                85                  90                  95
```

```
Ile Leu Gly Pro Pro Gly Ser Val Tyr Glu Gly Gly Val Phe Phe Leu
            100                 105                 110

Asp Ile Thr Phe Ser Ser Asp Tyr Pro Phe Lys Pro Pro Lys Val Thr
        115                 120                 125

Phe Arg Thr Arg Ile Tyr His Cys Asn Ile Asn Ser Gln Gly Val Ile
    130                 135                 140

Cys Leu Asp Ile Leu Lys Asp Asn Trp Ser Pro Ala Leu Thr Ile Ser
145                 150                 155                 160

Lys Val Leu Leu Ser Ile Cys Ser Leu Leu Thr Asp Cys Asn Pro Ala
                165                 170                 175

Asp Pro Leu Val Gly Ser Ile Ala Thr Gln Tyr Leu Thr Asn Arg Ala
            180                 185                 190

Glu His Asp Arg Ile Ala Arg Gln Trp Thr Lys Arg Tyr Ala Thr
        195                 200                 205
```

<210> SEQ ID NO 43
<211> LENGTH: 751
<212> TYPE: DNA
<213> ORGANISM: Homo sapiens
<220> FEATURE:
<221> NAME/KEY: misc_feature
<223> OTHER INFORMATION: GenBank Accession No.: NM_003969.1

<400> SEQUENCE: 43

```
aggatgatca agctgttctc gctgaagcag cagaagaagg aggaggagtc ggcgggcggc    60
accaagggca gcagcaagaa ggcgtcggcg gcgcagctgc ggatccagaa ggacataaac   120
gagctgaacc tgcccaagac gtgtgatatc agcttctcag atccagacga cctcctcaac   180
ttcaagctgg tcatctgtcc tgatgagggc ttctacaaga gtgggaagtt tgtgttcagt   240
tttaaggtgg gccagggtta cccgcatgat ccccccaagg tgaagtgtga cacaatggtc   300
tatcacccca acattgacct cgagggcaac gtctgcctca acatcctcag agaggactgg   360
aagccagtcc ttacgataaa ctccataatt tatggcctgc agtatctctt cttggagccc   420
aaccccgagg acccactgaa caaggaggcc gcagaggtcc tgcagaacaa ccggcggctg   480
tttgagcaga acgtgcagcg ctccatgcgg ggtggctaca tcggctccac ctactttgag   540
cgctgcctga ataggggttg gcgcataccc acccgccgcc acggccacaa gcctggcat   600
ccctgcaaa tatttattgg gggccatggg tagggtttg ggggcggcc ggtgggggaa   660
tcccctgcct tggccttgcc tcccttcct gccacgtgcc ctagttatt ttttttaa    720
caccaggcta actaaagggg aatgttactg c                                 751
```

<210> SEQ ID NO 44
<211> LENGTH: 183
<212> TYPE: PRT
<213> ORGANISM: Homo sapiens
<220> FEATURE:
<221> NAME/KEY: MISC_FEATURE
<223> OTHER INFORMATION: GenBank Accession No.: NP_003960.1

<400> SEQUENCE: 44

```
Met Ile Lys Leu Phe Ser Leu Lys Gln Gln Lys Lys Glu Glu Glu Ser
1               5                   10                  15

Ala Gly Gly Thr Lys Gly Ser Ser Lys Lys Ala Ser Ala Ala Gln Leu
            20                  25                  30

Arg Ile Gln Lys Asp Ile Asn Glu Leu Asn Leu Pro Lys Thr Cys Asp
        35                  40                  45
```

-continued

```
Ile Ser Phe Ser Asp Pro Asp Leu Leu Asn Phe Lys Leu Val Ile
 50                  55                  60

Cys Pro Asp Glu Gly Phe Tyr Lys Ser Gly Lys Phe Val Phe Ser Phe
 65                  70                  75                  80

Lys Val Gly Gln Gly Tyr Pro His Asp Pro Lys Val Lys Cys Glu
                 85                  90                  95

Thr Met Val Tyr His Pro Asn Ile Asp Leu Glu Gly Asn Val Cys Leu
                100                 105                 110

Asn Ile Leu Arg Glu Asp Trp Lys Pro Val Leu Thr Ile Asn Ser Ile
                115                 120                 125

Ile Tyr Gly Leu Gln Tyr Leu Phe Leu Glu Pro Asn Pro Glu Asp Pro
                130                 135                 140

Leu Asn Lys Glu Ala Ala Glu Val Leu Gln Asn Asn Arg Arg Leu Phe
145                 150                 155                 160

Glu Gln Asn Val Gln Arg Ser Met Arg Gly Gly Tyr Ile Gly Ser Thr
                165                 170                 175

Tyr Phe Glu Arg Cys Leu Lys
                180
```

<210> SEQ ID NO 45
<211> LENGTH: 2223
<212> TYPE: DNA
<213> ORGANISM: Homo sapiens
<220> FEATURE:
<221> NAME/KEY: misc_feature
<223> OTHER INFORMATION: GenBank Accession No.: NM_005339.2
<220> FEATURE:
<221> NAME/KEY: misc_feature
<222> LOCATION: (1997)..(1997)
<223> OTHER INFORMATION: n is a, c, g, or t

<400> SEQUENCE: 45

```
gaggaagagg tggcggcggt ggcggtggtc gtagcggtgg cggaggaggc gggaacgaat      60
cagctgcggg cggagacatg ccaacatcg cggtgcagcg aatcaagcgg gagttcaagg     120
aggtgctgaa gagcgaggag acgagcaaaa atcaaattaa agtagatctt gtagatgaga    180 atttacaga attaagagga gaaatagcag gacctccaga cacaccatat gaaggaggaa     240
gataccaact agagataaaa ataccagaaa catacccatt taatcccccct aaggtccggt    300 ttatcactaa aatatggcat cctaatatta gttccgtcac agggctatt tgtttggata     360 tcctgaaaga tcaatgggca gctgcaatga ctctccgcac ggtattattg tcattgcaag    420
cactattggc agctgcagag ccagatgatc cacaggatgc tgtagtagca aatcagtaca    480
aacaaaatcc cgaaatgttc aaacagacag ctcgactttg gcacatgtg tatgctggag    540 caccagtttc tagtccagaa taccaaaaa aatagaaaaa cctatgtgct atgggctttg    600
ataggaatgc agtaatagtg gccttgtctt caaaatcatg ggatgtagag actgcaacag    660
aattgcttct gagtaactga ggcatagaga gctgctgata tagtcaagct tgcctcttct    720
tgaggagcac caacatctgt tattttagg attctgcata gatttctttt aatctggcat    780
tctcgcctaa tgatgttatc taggcaccat tggagactga aaaaaaaaaa tccctgctct    840
gtaaataaag ctaattaaac gtctgtgtaa atttaaaaag gggaaatact ttaattttt    900 ttcttaatag tgtaaaaatt ccctgagcta agctaaaacc atggaagaaa catgctactt    960
tagtgtttag cagtgtacca agactagcaa gagtttgctt caggatttgg ttgaataatt   1020
aagataatat ttggagtgtg tcagggccat tcaaattgtt ggtgttgcat cacagctacc   1080
ttaactgttt ttaacatgga tcctctgtgc ctgtgaattt acttgcatgc ttgtacttga   1140
```

-continued

```
cttcttagga tgggtagctg aaaagaccac cattttaagc atttgagaat tcttaaatat    1200
gaaatttatt cagaattgaa gatggtgacc tattcagagc ctttttgtcc ttgtcaacag    1260
actgggacag tgtctgattc ccccttcacc cccccccacc cccgccttgg cacacacagc    1320
taatattcta atggtaaatt tctctgtatc aggtggggaa atgtgctgaa ggacagtatg    1380
tatcccttgc ttcatttta ggtcgtaggt ttggaatgtc ttgtcccagt tcttcaaaca    1440
ctcttaaatt tttcttaagt aatgtaaaaa tggaactgcc aattttattt ctcttgcaaa    1500
aatagtaaat acttgatgtt acattattcc caggtttaat gaaagaaccc aacttagttt    1560
ttcagtgaat ttgacaccta tttttagtg atgaaatttt tctttgagaa ctggcaagga     1620
tgcagtcagc tgtttgcagt ttttagcctg attttggggt ctatagagat tgctttattg    1680
gatacttcaa gtcattcttg cttgcacttc ccctattgac acatgaaagc tgtgttggtg    1740
ttttattgta catacttcag atgcacatag gaatagaagt gtgttataaa tctagctttc    1800
tttatgatgt ttctgataat acgagaattg aaaactttac cttctcttgt acatagtcag    1860
actatttgta ttaaatttac atttcattct aagttccaaa agtttgaaaa ttattagttt    1920
tgcaagatca cacactaatg taaccatttt atgaaggttg aagtggattt atgcaggcag    1980
ttctatatat agaaatncaa ttcttttta attttagga ccaatacaaa ataacacaaa      2040
tgtaatggaa tcagactgaa ttaaagtaag gctgtatatt gaaagtcata ttataaaagg    2100
tttgctttct ttaagtgtta tttatcttaa attataatcg ttaaatgttt ggaagataat    2160
ttttgaatca taacgtcagc ataacttcat ttgacttctc aataatcttg tcgacgcggc    2220
cgc                                                                  2223
```

<210> SEQ ID NO 46
<211> LENGTH: 200
<212> TYPE: PRT
<213> ORGANISM: Homo sapiens
<220> FEATURE:
<221> NAME/KEY: MISC_FEATURE
<223> OTHER INFORMATION: GenBank Accession No.: NP_005330.1

<400> SEQUENCE: 46

```
Met Ala Asn Ile Ala Val Gln Arg Ile Lys Arg Glu Phe Lys Glu Val
1               5                   10                  15

Leu Lys Ser Glu Glu Thr Ser Lys Asn Gln Ile Lys Val Asp Leu Val
                20                  25                  30

Asp Glu Asn Phe Thr Glu Leu Arg Gly Glu Ile Ala Gly Pro Pro Asp
            35                  40                  45

Thr Pro Tyr Glu Gly Gly Arg Tyr Gln Leu Glu Ile Lys Ile Pro Glu
        50                  55                  60

Thr Tyr Pro Phe Asn Pro Pro Lys Val Arg Phe Ile Thr Lys Ile Trp
65                  70                  75                  80

His Pro Asn Ile Ser Ser Val Thr Gly Ala Ile Cys Leu Asp Ile Leu
                85                  90                  95

Lys Asp Gln Trp Ala Ala Ala Met Thr Leu Arg Thr Val Leu Leu Ser
                100                 105                 110

Leu Gln Ala Leu Leu Ala Ala Ala Glu Pro Asp Asp Pro Gln Asp Ala
            115                 120                 125

Val Val Ala Asn Gln Tyr Lys Gln Asn Pro Glu Met Phe Lys Gln Thr
        130                 135                 140

Ala Arg Leu Trp Ala His Val Tyr Ala Gly Ala Pro Val Ser Ser Pro
145                 150                 155                 160
```

Glu Tyr Thr Lys Lys Ile Glu Asn Leu Cys Ala Met Gly Phe Asp Arg
                165                 170                 175

Asn Ala Val Ile Val Ala Leu Ser Ser Lys Ser Trp Asp Val Glu Thr
            180                 185                 190

Ala Thr Glu Leu Leu Leu Ser Asn
        195                 200

<210> SEQ ID NO 47
<211> LENGTH: 1238
<212> TYPE: DNA
<213> ORGANISM: Homo sapiens
<220> FEATURE:
<221> NAME/KEY: misc_feature
<223> OTHER INFORMATION: GenBank Accession No.: AF296658.1

<400> SEQUENCE: 47

| | | | | | |
|---|---|---|---|---|---|
| gcggcggcct | gcggcgggtt | cggtgggccc | aatcccgggg | cggtgcggct | gtttcgggcg | 60 |
| cgggcccgct | tttccgcacc | ctgctccggc | ctcgactacg | gcgagcctga | cgcggcggcg | 120 |
| gcccacgcca | gactagggag | agatgagcag | caccagcagt | aagagggctc | cgaccacggc | 180 |
| aacccagagg | ctgaagcagg | actaccttcg | cattaagaaa | gacccggtgc | cttacatctg | 240 |
| tgccgagccc | ctcccttcga | atattctcga | gtggcactat | gtcgtccgag | gcccagagat | 300 |
| gacccccttat | gaaggtggct | attatcatgg | aaaactaatt | tttcccagag | aatttccttt | 360 |
| caaacctccc | agtatctata | tgatcactcc | caacgggagg | tttaagtgca | acaccaggct | 420 |
| gtgtctttct | atcacggatt | ccacccgga | cacgtggaac | ccggcctggt | ctgtctccac | 480 |
| catcctgact | gggctcctga | gcttcatggt | ggagaagggc | cccaccctgg | cagtatagaa | 540 |
| gacgtcggac | ttcacgaaaa | gacaactggc | agtgcagagt | ttagcattta | atttgaaaga | 600 |
| taaagtctttt | tgtgaattat | ttcctgaagt | cgtggaggag | attaaacaaa | aacagaaagc | 660 |
| acaagacgaa | ctcagtagca | gaccccagac | tctccccttg | ccagacgtgg | ttccagacgg | 720 |
| ggagacgcac | ctcgtccaga | acgggattca | gctgctcaac | gggcatgcgc | cgggggccgt | 780 |
| ccaaacctcg | cagggctcca | gcaggccaac | cggcaccacg | gactctgggt | ggcgccctgg | 840 |
| cgaacttgtt | tgtatagttg | ggtttgcagc | ctttgcttac | acggtcaagt | acgtgctgag | 900 |
| gagcatcgcg | caggagtgag | cccaggcgcc | cagacccaag | cgccactga | gggcaccgcg | 960 |
| caccagagcg | tgacctcggc | aggctggaca | cactgcccag | cacaggcaga | cccaccaggc | 1020 |
| tcctaggttt | agcttttaaa | aacctgaaag | gggaagcaaa | aaccaaaatg | tgtgactggg | 1080 |
| ctttggagga | gactggagcc | tcagccctgt | cctggccacg | ggccgctggg | gctggtgtgg | 1140 |
| gtgggccttg | tgtgctggat | ttgtagctta | tcttccgtgt | tgtctttgga | cctgttttag | 1200 |
| taaacccgtt | tttcattta | aaaaaaaaa | aaaaaaaa | | | 1238 |

<210> SEQ ID NO 48
<211> LENGTH: 258
<212> TYPE: PRT
<213> ORGANISM: Homo sapiens
<220> FEATURE:
<221> NAME/KEY: MISC_FEATURE
<223> OTHER INFORMATION: GenBank Accession No.: AAK52609.1

<400> SEQUENCE: 48

Met Ser Ser Thr Ser Ser Lys Arg Ala Pro Thr Thr Ala Thr Gln Arg
1               5                   10                  15

Leu Lys Gln Asp Tyr Leu Arg Ile Lys Lys Asp Pro Val Pro Tyr Ile
            20                  25                  30

-continued

```
Cys Ala Glu Pro Leu Pro Ser Asn Ile Leu Glu Trp His Tyr Val Val
         35                  40                  45

Arg Gly Pro Glu Met Thr Pro Tyr Glu Gly Gly Tyr Tyr His Gly Lys
 50                  55                  60

Leu Ile Phe Pro Arg Glu Phe Pro Phe Lys Pro Pro Ser Ile Tyr Met
 65                  70                  75                  80

Ile Thr Pro Asn Gly Arg Phe Lys Cys Asn Thr Arg Leu Cys Leu Ser
                 85                  90                  95

Ile Thr Asp Phe His Pro Asp Thr Trp Asn Pro Ala Trp Ser Val Ser
             100                 105                 110

Thr Ile Leu Thr Gly Leu Leu Ser Phe Met Val Glu Lys Gly Pro Thr
         115                 120                 125

Leu Gly Ser Ile Glu Thr Ser Asp Phe Thr Lys Arg Gln Leu Ala Val
130                 135                 140

Gln Ser Leu Ala Phe Asn Leu Lys Asp Lys Val Phe Cys Glu Leu Phe
145                 150                 155                 160

Pro Glu Val Val Glu Glu Ile Lys Gln Lys Gln Lys Ala Gln Asp Glu
                165                 170                 175

Leu Ser Ser Arg Pro Gln Thr Leu Pro Leu Pro Asp Val Val Pro Asp
             180                 185                 190

Gly Glu Thr His Leu Val Gln Asn Gly Ile Gln Leu Leu Asn Gly His
         195                 200                 205

Ala Pro Gly Ala Val Gln Thr Ser Gln Gly Ser Ser Arg Pro Thr Gly
210                 215                 220

Thr Thr Asp Ser Gly Trp Arg Pro Gly Glu Leu Val Cys Ile Val Gly
225                 230                 235                 240

Phe Ala Ala Phe Ala Tyr Thr Val Lys Tyr Val Leu Arg Ser Ile Ala
                245                 250                 255

Gln Glu

<210> SEQ ID NO 49
<211> LENGTH: 1471
<212> TYPE: DNA
<213> ORGANISM: Homo sapiens
<220> FEATURE:
<221> NAME/KEY: misc_feature
<223> OTHER INFORMATION: GenBank Accession No.: NM_015983.1

<400> SEQUENCE: 49
gagagagaga gagagagaga gagagagaga gagagagaga gagagagaga gagagagaga      60
gagagagaga gagagagcag cgggccgcct caggcagccc cggccgggcc gcccgggtcc     120
ccggcagcgg ggtaggatgg cgctaaagcg gatccagaag gaattaaccg acttgcagag     180
ggatcctcct gcccagtgtt ctgcaggacc tgtcggtgat gacttgttcc actggcaggc     240
caccatcatg ggcccgaatg acagtcctta ccaaggaggt gttttcttcc tgaccatcca     300 cttcctaca  gattacccgt tcaagccccc aaaggttgct ttcacaacca aaatttatca     360
ccctaatatc aacagcaatg gcagcatctg ccttgatatc ctgcggtctc agtggtctcc     420
agcgttgact gtgtcaaaag ttctcttgtc catctgctcg ctgctctgcg accccaaccc     480
cgatgacccc ctggtgccag atatagcaca cacctacaag gccgacagag agaagtacaa     540
cagactagca agagagtgga cacaaaaata tgctatgtaa gtgccttgga ggttttacat     600
gagacactgt ccaagagaag ctggcagaga ggtcttccct taaaactttg gctgttggc      660 tgagccattc aaagagcatc atctgttctt caaacaaatg ttggtcaccc actctctcca     720
```

```
gctgcagcat gttggtgcca ttttcagcaa ttacggcttt gacagtgcca cctctttgat      780
gccaaatcag caaccattgt tgttatgatc tgcagtcttc ctggtgacac tggaatctct      840
ctctctgccg cctcagtttg tctgctggtc tcttgggggg ccaggccctg cacgtctctc      900
ctacccggcc tcaaatggtg ctgctgccca tgatggtacc acaccagggc tcagcctgg       960 cccctcacca catacccttt gccttttaga actcagtgcc atcctgggtg cccagggcag     1020
agcaggcttt gttcgcacct catctgctgc agaaccacat cctgaggagt ctcagcttat     1080
cctggaggga attgggaaca gtgtcactgg gaagtgaagg cctagccctg tggcttccac     1140
cagtctcctc ctgcagtgcc acgtggtggc atttctcgcc tcacaccaag aagcagcaag     1200
tggaaaattt caggatacaa agcacataac accccataag agatgattat gtttttagaa     1260
gcaagagcaa aattatgaaa cctctagaga tttgggtcat gttactccat ttgatgaaga     1320
ttctcactac cgcccgctcc tcccatagga gcctacacta agtccaagtg tgagccattc     1380
acagactaga acacaaggag ggagagagac tcttaaacgt aaataaaaat gcaattcact     1440
cacaactcta aaaaaaaaa aaaaaaaaa a                                      1471
```

<210> SEQ ID NO 50
<211> LENGTH: 147
<212> TYPE: PRT
<213> ORGANISM: Homo sapiens
<220> FEATURE:
<221> NAME/KEY: MISC_FEATURE
<223> OTHER INFORMATION: GenBank Accession No.: NP_057067

<400> SEQUENCE: 50

```
Met Ala Leu Lys Arg Ile Gln Lys Glu Leu Thr Asp Leu Gln Arg Asp
1               5                   10                  15

Pro Pro Ala Gln Cys Ser Ala Gly Pro Val Gly Asp Asp Leu Phe His
                20                  25                  30

Trp Gln Ala Thr Ile Met Gly Pro Asn Asp Ser Pro Tyr Gln Gly Gly
            35                  40                  45

Val Phe Phe Leu Thr Ile His Phe Pro Thr Asp Tyr Pro Phe Lys Pro
        50                  55                  60

Pro Lys Val Ala Phe Thr Thr Lys Ile Tyr His Pro Asn Ile Asn Ser
65                  70                  75                  80

Asn Gly Ser Ile Cys Leu Asp Ile Leu Arg Ser Gln Trp Ser Pro Ala
                85                  90                  95

Leu Thr Val Ser Lys Val Leu Leu Ser Ile Cys Ser Leu Leu Cys Asp
                100                 105                 110

Pro Asn Pro Asp Asp Pro Leu Val Pro Glu Ile Ala His Thr Tyr Lys
            115                 120                 125

Ala Asp Arg Glu Lys Tyr Asn Arg Leu Ala Arg Glu Trp Thr Gln Lys
        130                 135                 140

Tyr Ala Met
145
```

<210> SEQ ID NO 51
<211> LENGTH: 1366
<212> TYPE: DNA
<213> ORGANISM: Homo sapiens
<220> FEATURE:
<221> NAME/KEY: misc_feature
<223> OTHER INFORMATION: GenBank Accession No.: NM_080678.1

<400> SEQUENCE: 51

```
gcgtctcgca gcagccgccc ggaccgggca tggtgttggg cgccgggccc gcctcgcctg      60
tctcggggag cccagggtaa aggcagcagt aatgctaacg ctagcaagta aactgaagcg     120
tgacgatggt ctcaaagggt cccggacggc agccacagcg tccgactcga ctcggagggt     180
ttctgtgaga gacaaattgc ttgttaaaga ggttgcagaa cttgaagcta atttaccttg     240
tacatgtaaa gtgcattttc ctgatccaaa caagcttcat tgttttcagc taacagtaac     300
cccagatgag ggttactacc agggtggaaa atttcagttt gaaactgaag ttcccgatgc     360
gtacaacatg gtgcctccca aagtgaaatg cctgaccaag atctggcacc ccaacatcac     420
agagacaggg gaaatatgtc tgagtttatt gagagaaaca tcaattgatg gcactggctg     480
ggctcccaca agaacattaa aggatgtcgt ttggggatta aactctttgt ttactgatct     540
tttgaatttt gatgatccac tgaatattga agctgcagaa catcatttgc gggacaagga     600
ggacttccgg aataaagtgg atgactacat caaacgttat gccagatgat aaaaggggac     660
gattgcaggc ccatggactg tgttacagtt tgtctctaac atgaaacagc aagaggtagc     720
cccctctccc gtcctcatgc tccctctcag tcccctggat tgccccagtc ctgtgaccat     780
gttgccctga agaaggaccat cttcatgact gctcattgta gatggagaat tcaacataaa     840
tacagcaaga aaatgtgttt gggcttctga agagttgtct gcttacctta acatgtttac     900 tttttttgaac ttgtactgta taggctgttg gtgaaattct taagaagttg taatgaactc     960
aaaattgagg ccagagcttg ctttcccttt tcccaaacaa aattggtttt ctgcacaagc    1020
gatgctaatg atgtgttcag tgtaactcgc agattggcaa taagataccc gctacaaact    1080
gtgattggat gcaaaatctc ttagcttctt tcacgaatgt tggccctgcc tagatgttgt    1140
gaagcctccc agaatgcata gagtcattca ctgtagatcc cttattgaaa tgcgtatttt    1200
atttaatgta agtatatttt ggaacagatt tgtaatttgt acaattcaat gctttaatta    1260
ttttttctat tctcatttag tttgtatttt cattgtatag agcagacaga aagatgttgg    1320
gtcaagcaac tattgaagag aaatacaaag aaaaaaaaaa aaaaaa                   1366
```

<210> SEQ ID NO 52
<211> LENGTH: 185
<212> TYPE: PRT
<213> ORGANISM: Homo sapiens
<220> FEATURE:
<221> NAME/KEY: MISC_FEATURE
<223> OTHER INFORMATION: GenBank Accession No.: NP_542409.1

<400> SEQUENCE: 52

```
Met Leu Thr Leu Ala Ser Lys Leu Lys Arg Asp Asp Gly Leu Lys Gly
1               5                   10                  15

Ser Arg Thr Ala Ala Thr Ala Ser Asp Ser Thr Arg Arg Val Ser Val
            20                  25                  30

Arg Asp Lys Leu Leu Val Lys Glu Val Ala Glu Leu Glu Ala Asn Leu
        35                  40                  45

Pro Cys Thr Cys Lys Val His Phe Pro Asp Pro Asn Lys Leu His Cys
    50                  55                  60

Phe Gln Leu Thr Val Thr Pro Asp Glu Gly Tyr Tyr Gln Gly Gly Lys
65                  70                  75                  80

Phe Gln Phe Glu Thr Glu Val Pro Asp Ala Tyr Asn Met Val Pro Pro
                85                  90                  95

Lys Val Lys Cys Leu Thr Lys Ile Trp His Pro Asn Ile Thr Glu Thr
            100                 105                 110

Gly Glu Ile Cys Leu Ser Leu Leu Arg Glu His Ser Ile Asp Gly Thr
```

-continued

```
                115                 120                 125
Gly Trp Ala Pro Thr Arg Thr Leu Lys Asp Val Val Trp Gly Leu Asn
    130                 135                 140

Ser Leu Phe Thr Asp Leu Leu Asn Phe Asp Asp Pro Leu Asn Ile Glu
145                 150                 155                 160

Ala Ala Glu His His Leu Arg Asp Lys Glu Asp Phe Arg Asn Lys Val
                165                 170                 175

Asp Asp Tyr Ile Lys Arg Tyr Ala Arg
            180                 185

<210> SEQ ID NO 53
<211> LENGTH: 1203
<212> TYPE: DNA
<213> ORGANISM: Homo sapiens
<220> FEATURE:
<221> NAME/KEY: misc_feature
<223> OTHER INFORMATION: GenBank Accession No.: NM_003348.1

<400> SEQUENCE: 53
actcgtgcgt gaggcgagag gagccggaga cgagaccaga ggccgaactc gggttctgac      60
aagatggccg ggctgccccg caggatcatc aaggaaaccc agcgtttgct ggcagaacca     120
gttcctggca tcaaagccga accagatgag agcaacgccc gttattttca gtgtggtcatt    180 gctggccctc aggattcccc ctttgaggga gggacttta aacttgaact attccttcca      240
gaagaatacc caatggcagc ccctaaagta cgtttcatga ccaaaattta tcatcctaat     300
gtagacaagt tgggaagaat atgtttagat attttgaaag ataagtggtc cccagcactg     360
cagatccgca cagttctgct atcgatccag gccttgttaa gtgctcccaa tccagatgat     420
ccattagcaa atgatgtagc ggagcagtgg aagaccaacg aagcccaagc catagaaaca     480
gctagagcat ggactaggct atatgccatg aataatattt aaattgatac gatcatcaag     540
tgtgcatcac ttctcctgtt ctgccaagac ttcctcctct ttgtttgcat taatggaca     600 cagtcttaga acattacag aataaaaaag cccagacatc ttcagtcctt tggtgattaa     660
atgcacatta gcaaatctat gtcttgtcct gattcactgt cataaagcat gagcagaggc     720
tagaagtatc atctggattg ttgtgaaacg tttaaaagca gtggcccctc cctgctttta     780
ttcatttccc ccatcctggt ttaagtataa agcactgtga atgaaggtag ttgtcaggtt     840
agctgcaggg gtgtgggtgt ttttatttta ttttattta ttttattttt gagggggag      900 gtagtttaat tttatgggct cctttccccc tttttggtg atctaattgc attggttaaa     960
agcagctaac caggtcttta gaatatgctc tagccaagtc taactttatt tagacgctgt    1020
agatggacaa gcttgattgt tggaaccaaa atgggaacat taaacaaaca tcacagccct    1080
cactaataac attgctgtca agtgtagatt cccccttca aaaaagctt gtgaccattt      1140 tgtatggctt gtctggaaac ttctgtaaat cttatgtttt agtaaatat ttttgttat      1200 tct                                                                  1203
```

```
<210> SEQ ID NO 54
<211> LENGTH: 152
<212> TYPE: PRT
<213> ORGANISM: Homo sapiens
<220> FEATURE:
<221> NAME/KEY: MISC_FEATURE
<223> OTHER INFORMATION: GenBank Accession No.: NP_003339.1

<400> SEQUENCE: 54

Met Ala Gly Leu Pro Arg Arg Ile Ile Lys Glu Thr Gln Arg Leu Leu
```

```
                1               5                   10                  15
        Ala Glu Pro Val Pro Gly Ile Lys Ala Glu Pro Asp Glu Ser Asn Ala
                        20                  25                  30

Arg Tyr Phe His Val Val Ile Ala Gly Pro Gln Asp Ser Pro Phe Glu
                        35                  40                  45

Gly Gly Thr Phe Lys Leu Glu Leu Phe Leu Pro Glu Glu Tyr Pro Met
                50                  55                  60

Ala Ala Pro Lys Val Arg Phe Met Thr Lys Ile Tyr His Pro Asn Val
        65                  70                  75                  80

Asp Lys Leu Gly Arg Ile Cys Leu Asp Ile Leu Lys Asp Lys Trp Ser
                        85                  90                  95

Pro Ala Leu Gln Ile Arg Thr Val Leu Leu Ser Ile Gln Ala Leu Leu
                        100                 105                 110

Ser Ala Pro Asn Pro Asp Asp Pro Leu Ala Asn Asp Val Ala Glu Gln
                        115                 120                 125

Trp Lys Thr Asn Glu Ala Gln Ala Ile Glu Thr Ala Arg Ala Trp Thr
            130                 135                 140

Arg Leu Tyr Ala Met Asn Asn Ile
        145                 150

<210> SEQ ID NO 55
<211> LENGTH: 892
<212> TYPE: DNA
<213> ORGANISM: Homo sapiens
<220> FEATURE:
<221> NAME/KEY: misc_feature
<223> OTHER INFORMATION: GenBank Accession No.: NM_016476

<400> SEQUENCE: 55
gtgcgcactg gcgtgcgaga ctcggcgggc gctgttgagg gagtcgggcc gcgactgtgg    60
tcgtttttat accttcccgc gcggacgccg gcgctgccaa cggaagggcg ggtagggcgg    120
tgcgtgatta ggttggcgaa gagacggagt ttcgtcatgt tggccaggcc catttgagat    180
ctttgaagat atcctcaacg tgaggctctg ctgccatgaa ggtgaagatt aagtgctgga    240
acggcgtggc cacttggctc tgggtggcca acgatgagaa ctgtggcatc tgcaggatgg    300
catttaacgg atgctgccct gactgcaagg tgcccggcga cgactgcccg ctggtgtggg    360
gccagtgctc ccactgcttc cacatgcatt gcatcctcaa gtggctgcac gcacagcagg    420
tgcagcagca ctgccccatg tgccgccagg aatggaagtt caaggagtga ggcccgacct    480
ggctctcgct ggaggggcat cctgagactc cttcctcatg ctggcgccga tggctgctgg    540
ggacagcgcc cctgagctgc aacaaggtgg aaacaagggc tggagctgcg tttgttttgc    600
catcactatg ttgacacttt tatccaataa gtgaaaactc attaaactac tcaaatcttg    660
ctggaggcct ctgggtgcct gtgttctcgg catatagatg tggtctcggt gtgttttgat    720
atgaaaactc tcatgaataa acatctccgt gaaacgccaa ggcctcgtc aaaccctgag     780 tcatgactgg gaggagaagg agcaggatca gacggtagag cctggggcat gctcttcagg    840
catgctcttg cctgctggat tgccggcggc ggccctggga ccctccctca gg            892

<210> SEQ ID NO 56
<211> LENGTH: 84
<212> TYPE: PRT
<213> ORGANISM: Homo sapiens
<220> FEATURE:
<221> NAME/KEY: MISC_FEATURE
<223> OTHER INFORMATION: GenBank Accession No.: NP_057560
```

-continued

```
<400> SEQUENCE: 56

Met Lys Val Lys Ile Lys Cys Trp Asn Gly Val Ala Thr Trp Leu Trp
1               5                   10                  15

Val Ala Asn Asp Glu Asn Cys Gly Ile Cys Arg Met Ala Phe Asn Gly
            20                  25                  30

Cys Cys Pro Asp Cys Lys Val Pro Gly Asp Asp Cys Pro Leu Val Trp
        35                  40                  45

Gly Gln Cys Ser His Cys Phe His Met His Cys Ile Leu Lys Trp Leu
    50                  55                  60

His Ala Gln Gln Val Gln Gln His Cys Pro Met Cys Arg Gln Glu Trp
65                  70                  75                  80

Lys Phe Lys Glu

<210> SEQ ID NO 57
<211> LENGTH: 2733
<212> TYPE: DNA
<213> ORGANISM: Homo sapiens
<220> FEATURE:
<221> NAME/KEY: misc_feature
<223> OTHER INFORMATION: GenBank Accession No.: NM_013366

<400> SEQUENCE: 57
tcatggctgc gcgtgcagac gtgcgtcatc gccgcgcgcc gcgccgagcg aatctcggag      60
tcggtgggtg cagatggcgg cggcagttgt ggtggcggag ggggacagcg actcccggcc     120
cggacaggag ttgttagtgg cctggaacac cgtgagcacc ggcctggtgc cgccggctgc     180
gctggggctg gtgtcttccc ggaccagcgg tgcagtcccg ccaaaggaag aggagctccg     240
ggcggcggtg gaggttctga ggggccacgg gctacactcg gtcctggagg agtggttcgt     300
ggaggtgctg cagaacgatc tgcaggccaa catctcccct gagttctgga atgccatctc     360
ccaatgcgag aactctgcgg atgagcccca gtgcctttg ctactccttg acgcttttgg      420
cctgctggag agccgcctgg atccctacct gcgtagccta gagctgctgg agaaatggac     480
tcgcctgggc ttgctgatgg cactggtgc tcagggctg cgagaagaag tccacactat       540
gttgcgcgga gtcttgttct ttagcacccc cagaaccttc aagagatga tccagcgtct      600 gtatgggtgc ttcttgagag tctatatgca gagtaagagg aaggggggaag ggggcacaga    660 ccccgaactg gaaggggagc tggacagccg gtatgcccgt cgccggtact accggctcct     720
gcagagcccg ctgtgtgcag ggtgcagcag tgacaagcaa cagtgctggt gtcgccaggc     780
tctggagcag ttccatcagc tcagccaggt cttacacagg ctcagtctgc tggagcgggt     840
cagtgccgag gctgtgacca ccaccctgca ccaggtgacc cgggagagga tggaggaccg     900
ttgccggggc gagtacgagc gctccttcct gcgtgagttc acaagtgga tcgagcgggt     960 ggtcggctgg ctcggcaagg tgttcctgca ggacggcccc gccaggcccg catctcccga    1020
ggccggcaac accctgcgcc gctggcgctg ccacgtgcaa aggttcttct accgcatcta    1080
cgccagcctg cgcatcgagg agctcttcag catcgtccga gacttcccag actcccggcc    1140
agccatcgag gacctcaagt actgcctgga gaggacggac cagaggcagc agctgctcgt    1200
gtccctcaag gctgccctgg agactcggct cctgcatcca ggcgtcaaca cgtgtgacat    1260
catcaccctc tatatctctg ccatcaaggc gctgcgcgtg ctggaccctt ccatggtcat    1320
cctggaggtg gcctgtgagc ctatccgccg ctacctgagg acgcgggagg acacagtgcg    1380
gcagattgtg gctgggctga cggggggactc ggacggggaca ggggacctgg ctgttgagct    1440
gtccaagacc gacccggcga gcctggagac aggccaggac agtgaggatg actcaggcga    1500
```

-continued

```
gccagaggac tgggtcccgg accctgtgga tgccgatcca gggaagtcga gctccaagcg    1560
gcgttcatcg acatcatca gcctgctggt cagcatctac ggcagcaagg acctcttcat    1620
caatgagtac cgctcgctgc tggccgaccg cctgctgcac cagttcagct tcagccccga    1680
gcgggagatc cgcaacgtgg agctgctgaa gctgcgcttt ggcgaggccc aatgcacttt   1740
ctgtgaagtc atgctgaagg acatggcgga ctcccgccgc atcaatgcca acatccggga    1800
ggaggatgag aagcggccag cagaggagca gccaccgttc ggggtctacg ctgtcatcct    1860
gtccagtgag ttctggccgc ccttcaagga cgagaagctg gaggtccccg aggatatcag    1920
ggcagccctg gaggcttact gcaagaagta tgagcagctc aaggccatgc ggaccctcag    1980
ttggaagcac accctgggcc tggtgaccat ggacgtggag ctggccgacc gcacgctgtc    2040
tgtggcggtc accccagtac aggcggtgat cttgctgtat tttcaggacc aagccagctg    2100
gaccctggag gaactgagca aggcggtgaa gatgcccgtg gcgctgctgc ggcggcggat    2160
gtccgtgtgg ctgcagcagg gtgtgctgcg tgaggagccc cccggcacct tctctgtcat    2220
tgaggaggag cggcctcagg accgggacaa catggtgctc attgacagtg acgacgagag    2280
cgactccggc atggcctccc aggccgacca gaaggaggag gagctgctgc tcttctggac    2340
gtacatccag gccatgctga ccaacctgga gagcctctca ctggatcgta tctacaacat    2400
gctccgcatg tttgtggtga ctgggcctgc actggccgag attgacctgc aggagctgca    2460
gggctacctg cagaagaagg tgcgggacca gcagctcgtc tactcggccg gcgtctaccg    2520
cctgcccaag aactgcagct gacacatcgc ccgcccgccc gcccgccgc caggcgctgc    2580 cctgcaggtg ctctcgtcct cccgtgccag ccccgcccg ccgtgtccc agaatgcact    2640 gctgaggagc atgcccaccc ccaccccgc agtgtgcaga ttaaagcaag tcagatcatc    2700 aaaaaaaaa aaaaaaaaa aaaaaaaaaa aaa                                 2733
```

<210> SEQ ID NO 58
<211> LENGTH: 822
<212> TYPE: PRT
<213> ORGANISM: Homo sapiens
<220> FEATURE:
<221> NAME/KEY: MISC_FEATURE
<223> OTHER INFORMATION: GenBank Accession No.: NP_037498

<400> SEQUENCE: 58

```
Met Ala Ala Ala Val Val Ala Glu Gly Asp Ser Asp Ser Arg Pro
1               5                   10                  15

Gly Gln Glu Leu Leu Val Ala Trp Asn Thr Val Ser Thr Gly Leu Val
            20                  25                  30

Pro Pro Ala Ala Leu Gly Leu Val Ser Ser Arg Thr Ser Gly Ala Val
        35                  40                  45

Pro Pro Lys Glu Glu Leu Arg Ala Ala Val Glu Val Leu Arg Gly
    50                  55                  60

His Gly Leu His Ser Val Leu Glu Glu Trp Phe Val Glu Val Leu Gln
65                  70                  75                  80

Asn Asp Leu Gln Ala Asn Ile Ser Pro Glu Phe Trp Asn Ala Ile Ser
                85                  90                  95

Gln Cys Glu Asn Ser Ala Asp Glu Pro Gln Cys Leu Leu Leu Leu
            100                 105                 110

Asp Ala Phe Gly Leu Leu Glu Ser Arg Leu Asp Pro Tyr Leu Arg Ser
        115                 120                 125

Leu Glu Leu Leu Glu Lys Trp Thr Arg Leu Gly Leu Leu Met Gly Thr
```

-continued

```
            130                 135                 140
Gly Ala Gln Gly Leu Arg Glu Glu Val His Thr Met Leu Arg Gly Val
145                 150                 155                 160
Leu Phe Phe Ser Thr Pro Arg Thr Phe Gln Glu Met Ile Gln Arg Leu
                    165                 170                 175
Tyr Gly Cys Phe Leu Arg Val Tyr Met Gln Ser Lys Arg Lys Gly Glu
                180                 185                 190
Gly Gly Thr Asp Pro Glu Leu Glu Gly Glu Leu Asp Ser Arg Tyr Ala
                195                 200                 205
Arg Arg Arg Tyr Tyr Arg Leu Leu Gln Ser Pro Leu Cys Ala Gly Cys
            210                 215                 220
Ser Ser Asp Lys Gln Gln Cys Trp Cys Arg Gln Ala Leu Glu Gln Phe
225                 230                 235                 240
His Gln Leu Ser Gln Val Leu His Arg Leu Ser Leu Glu Arg Val
                    245                 250                 255
Ser Ala Glu Ala Val Thr Thr Thr Leu His Gln Val Thr Arg Glu Arg
                260                 265                 270
Met Glu Asp Arg Cys Arg Gly Glu Tyr Glu Arg Ser Phe Leu Arg Glu
            275                 280                 285
Phe His Lys Trp Ile Glu Arg Val Val Gly Trp Leu Gly Lys Val Phe
        290                 295                 300
Leu Gln Asp Gly Pro Ala Arg Pro Ala Ser Pro Glu Ala Gly Asn Thr
305                 310                 315                 320
Leu Arg Arg Trp Arg Cys His Val Gln Arg Phe Phe Tyr Arg Ile Tyr
                    325                 330                 335
Ala Ser Leu Arg Ile Glu Glu Leu Phe Ser Ile Val Arg Asp Phe Pro
                340                 345                 350
Asp Ser Arg Pro Ala Ile Glu Asp Leu Lys Tyr Cys Leu Glu Arg Thr
            355                 360                 365
Asp Gln Arg Gln Gln Leu Leu Val Ser Leu Lys Ala Ala Leu Glu Thr
        370                 375                 380
Arg Leu His Pro Gly Val Asn Thr Cys Asp Ile Ile Thr Leu Tyr
385                 390                 395                 400
Ile Ser Ala Ile Lys Ala Leu Arg Val Leu Asp Pro Ser Met Val Ile
                    405                 410                 415
Leu Glu Val Ala Cys Glu Pro Ile Arg Arg Tyr Leu Arg Thr Arg Glu
                420                 425                 430
Asp Thr Val Arg Gln Ile Val Ala Gly Leu Thr Gly Asp Ser Asp Gly
            435                 440                 445
Thr Gly Asp Leu Ala Val Glu Leu Ser Lys Thr Asp Pro Ala Ser Leu
        450                 455                 460
Glu Thr Gly Gln Asp Ser Glu Asp Ser Gly Glu Pro Glu Asp Trp
465                 470                 475                 480
Val Pro Asp Pro Val Asp Ala Asp Pro Gly Lys Ser Ser Lys Arg
                    485                 490                 495
Arg Ser Ser Asp Ile Ile Ser Leu Leu Val Ser Ile Tyr Gly Ser Lys
                500                 505                 510
Asp Leu Phe Ile Asn Glu Tyr Arg Ser Leu Leu Ala Asp Arg Leu Leu
            515                 520                 525
His Gln Phe Ser Phe Ser Pro Glu Arg Glu Ile Arg Asn Val Glu Leu
        530                 535                 540
Leu Lys Leu Arg Phe Gly Glu Ala Pro Met His Phe Cys Glu Val Met
545                 550                 555                 560
```

```
Leu Lys Asp Met Ala Asp Ser Arg Arg Ile Asn Ala Asn Ile Arg Glu
            565                 570                 575
Glu Asp Glu Lys Arg Pro Ala Glu Glu Gln Pro Pro Phe Gly Val Tyr
        580                 585                 590
Ala Val Ile Leu Ser Ser Glu Phe Trp Pro Phe Lys Asp Glu Lys
    595                 600                 605
Leu Glu Val Pro Glu Asp Ile Arg Ala Leu Glu Ala Tyr Cys Lys
    610                 615                 620
Lys Tyr Glu Gln Leu Lys Ala Met Arg Thr Leu Ser Trp Lys His Thr
625                 630                 635                 640
Leu Gly Leu Val Thr Met Asp Val Glu Leu Ala Asp Arg Thr Leu Ser
            645                 650                 655
Val Ala Val Thr Pro Val Gln Ala Val Ile Leu Leu Tyr Phe Gln Asp
            660                 665                 670
Gln Ala Ser Trp Thr Leu Glu Glu Leu Ser Lys Ala Val Lys Met Pro
        675                 680                 685
Val Ala Leu Leu Arg Arg Arg Met Ser Val Trp Leu Gln Gln Gly Val
    690                 695                 700
Leu Arg Glu Glu Pro Pro Gly Thr Phe Ser Val Ile Glu Glu Glu Arg
705                 710                 715                 720
Pro Gln Asp Arg Asp Asn Met Val Leu Ile Asp Ser Asp Glu Ser
            725                 730                 735
Asp Ser Gly Met Ala Ser Gln Ala Asp Gln Lys Glu Glu Glu Leu Leu
            740                 745                 750
Leu Phe Trp Thr Tyr Ile Gln Ala Met Leu Thr Asn Leu Glu Ser Leu
        755                 760                 765
Ser Leu Asp Arg Ile Tyr Asn Met Leu Arg Met Phe Val Val Thr Gly
    770                 775                 780
Pro Ala Leu Ala Glu Ile Asp Leu Gln Glu Leu Gln Gly Tyr Leu Gln
785                 790                 795                 800
Lys Lys Val Arg Asp Gln Gln Leu Val Tyr Ser Ala Gly Val Tyr Arg
            805                 810                 815
Leu Pro Lys Asn Cys Ser
            820

<210> SEQ ID NO 59
<211> LENGTH: 521
<212> TYPE: DNA
<213> ORGANISM: Homo sapiens
<220> FEATURE:
<221> NAME/KEY: misc_feature
<223> OTHER INFORMATION: GenBank Accession No.: NM_014248

<400> SEQUENCE: 59
agaccgtgtg tttccaaaat ggcggcagcg atggatgtgg ataccccgag cggcaccaac      60
agcggcgcgg gcaagaagcg ctttgaagtg aaaaagtgga atgcagtagc cctctgggcc     120
tgggatattg tggttgataa ctgtgccatc tgcaggaacc acattatgga tctttgcata     180
gaatgtcaag ctaaccaggc gtccgctact tcagaagagt gtactgtcgc atggggagtc     240
tgtaaccatg cttttcactt ccactgcatc tctcgctggc tcaaaacacg acaggtgtgt     300
ccattggaca cagagagtg ggaattccaa agtatgggc actaggaaaa gacttcttcc     360
atcaagctta attgttttgt tattcattta atgactttcc ctgctgttac ctaattacaa     420
attggatgga actgtgtttt tttctgcttt gttttttcag tttgctgttt ctgtagccat     480
```

```
attgtattct gtgtcaaata aagtccagtt ggattctgga a                              521
```

<210> SEQ ID NO 60
<211> LENGTH: 108
<212> TYPE: PRT
<213> ORGANISM: Homo sapiens
<220> FEATURE:
<221> NAME/KEY: MISC_FEATURE
<223> OTHER INFORMATION: GenBank Accession No.: NP_055063

<400> SEQUENCE: 60

```
Met Ala Ala Ala Met Asp Val Asp Thr Pro Ser Gly Thr Asn Ser Gly
1               5                   10                  15

Ala Gly Lys Lys Arg Phe Glu Val Lys Lys Trp Asn Ala Val Ala Leu
            20                  25                  30

Trp Ala Trp Asp Ile Val Val Asp Asn Cys Ala Ile Cys Arg Asn His
        35                  40                  45

Ile Met Asp Leu Cys Ile Glu Cys Gln Ala Asn Gln Ala Ser Ala Thr
    50                  55                  60

Ser Glu Glu Cys Thr Val Ala Trp Gly Val Cys Asn His Ala Phe His
65                  70                  75                  80

Phe His Cys Ile Ser Arg Trp Leu Lys Thr Arg Gln Val Cys Pro Leu
                85                  90                  95

Asp Asn Arg Glu Trp Glu Phe Gln Lys Tyr Gly His
            100                 105
```

<210> SEQ ID NO 61
<211> LENGTH: 2608
<212> TYPE: DNA
<213> ORGANISM: Homo sapiens
<220> FEATURE:
<221> NAME/KEY: misc_feature
<223> OTHER INFORMATION: GenBank Accession No.: NM_145803

<400> SEQUENCE: 61

```
agcagagaag gcggaagcag tggcgtccgc agctggggct tggcctgcgg gcggccagcg      60
aaggtggcga aggctcccac tggatccaga gtttgccgtc caagcagcct cgtctcggcg     120
cgcagtgtct gtgtccgtcc tctaccagcg ccttggctga gcggagtcgt gcggttggtg     180
ggggagccct gccctcctgg ttcggcctcc ccgcgcacta aacgatcat gaacttctga      240
agggacccag ctttctttgt gtgctccaag tgatttgcac aaataataat atatatattt     300
attgaaggag agaatcagag caagtgataa tcaagttact atgagtctgc taaactgtga     360
aaacagctgt ggatccagcc agtctgaaag tgactgctgt gtggccatgg ccagctcctg     420
tagcgctgta acaaaagatg atagtgtggg tggaactgcc agcacgggga acctctccag     480
ctcatttatg gaggagatcc agggatatga tgtagagttt gacccacccc tggaaagcaa     540
gtatgaatgc cccatctgct tgatggcatt acgagaagca gtgcaaacgc catgcggcca     600
taggttctgc aaagcctgca tcataaaatc aataagggat gcaggtcaca aatgtccagt     660
tgacaatgaa atactgctgg aaaatcaact atttccagac aattttgcaa acgtgagat      720
tctttctctg atggtgaaat gtccaaatga aggttgtttg cacaagatgg aactgagaca     780
tcttgaggat catcaagcac attgtgagtt tgctcttatg gattgtcccc aatgccagcg     840
tcccttccaa aaattccata ttaatattca cattctgaag gattgtccaa ggagacaggt     900
ttcttgtgac aactgtgctg catcaatggc atttgaagat aaagagatcc atgaccagaa     960
ctgtccttg gcaaatgtca tctgtgaata ctgcaatact atactcatca gagaaacagat    1020
```

-continued

```
gcctaatcat tatgatctag actgccctac agccccaatt ccatgcacat tcagtacttt      1080
tggttgccat gaaaagatgc agaggaatca cttggcacgc cacctacaag agaacaccca      1140
gtcacacatg agaatgttgg cccaggctgt tcatagtttg agcgttatac ccgactctgg      1200
gtatatctca gaggtccgga atttccagga aactattcac cagttagagg gtcgccttgt      1260
aagacaagac catcaaatcc gggagctgac tgctaaaatg gaaactcaga gtatgtatgt      1320
aagtgagctc aaacgaacca ttcgaaccct tgaggacaaa gttgctgaaa tcgaagcaca      1380
gcagtgcaat ggaatttata tttggaagat tggcaacttt ggaatgcatt tgaaatgtca      1440
agaagaggag aaacctgttg tgattcatag ccctggattc tacactggca aacccgggta      1500
caaactgtgc atgcgcttgc accttcagtt accgactgct cagcgctgtg caaactatat      1560
atcccttttt gtccacacaa tgcaaggaga atatgacagc cacctccctt ggcccttcca      1620
gggtacaata cgccttacaa ttcttgatca gtctgaagca cctgtaaggc aaaaccacga      1680
agagataatg gatgccaaac cagagctgct tgctttccag cgacccacaa tcccacggaa      1740
cccaaaaggt tttggctatg taacttttat gcatctggaa gccctaagac aaagaacttt      1800
cattaaggat gacacattat tagtgcgctg tgaggtctcc acccgctttg acatgggtag      1860
ccttcggagg gagggttttc agccacgaag tactgatgca ggggtatagc ttgccctcac      1920
ttgctcaaaa acaactacct ggagaaaaca gtgcctttcc ttgccctgtt ctcaataaca      1980
tgcaaacaaa caagccacgg gaaatatgta atatctacta gtgagtgttg ttagagaggt      2040
cacttactat ttcttcctgt tacaaatgat ctgaggcagt ttttcctgg gaatccacac      2100 gttccatgct ttttcagaaa tgttaggcct gaagtgcctg tggcatgttg cagcagctat      2160
tttgccagtt agtataccttc tttgttgtac tttcttgggc ttttgctctg gtgtatttta      2220
ttgtcagaaa gtccagactc aagagtacta aacttttaat aataatggat tttccttaaa      2280
acttcagtct ttttgtagta ttatatgtaa tatattaaaa gtgaaaatca ctaccgcctt      2340
gtgctagtgc cctcgagaag agttattgct ctagaaagtt gagttctcat tttttaacc      2400 tgttatagat ttcagaggat ttgaaccata atccttggaa aacttaagtt ctcattcacc      2460 ccagttttc ctccaggttg ttactaagga tattcaggga tgagtttaaa ccctaaatat      2520
aaccttaatt atttagtgta aacatgtctg ttgaataata cttgtttaag tgttaaaaaa      2580
aaaaaaaaaa agaaaaaaaa aaaaaaaa                                         2608
```

<210> SEQ ID NO 62
<211> LENGTH: 522
<212> TYPE: PRT
<213> ORGANISM: Homo sapiens
<220> FEATURE:
<221> NAME/KEY: MISC_FEATURE
<223> OTHER INFORMATION: GenBank Accession No.: NP_665802

<400> SEQUENCE: 62

```
Met Ser Leu Leu Asn Cys Glu Asn Ser Cys Gly Ser Ser Gln Ser Glu
1               5                   10                  15

Ser Asp Cys Cys Val Ala Met Ala Ser Ser Cys Ser Ala Val Thr Lys
            20                  25                  30

Asp Asp Ser Val Gly Gly Thr Ala Ser Thr Gly Asn Leu Ser Ser Ser
        35                  40                  45

Phe Met Glu Glu Ile Gln Gly Tyr Asp Val Glu Phe Asp Pro Pro Leu
    50                  55                  60

Glu Ser Lys Tyr Glu Cys Pro Ile Cys Leu Met Ala Leu Arg Glu Ala
65                  70                  75                  80
```

-continued

```
Val Gln Thr Pro Cys Gly His Arg Phe Cys Lys Ala Cys Ile Ile Lys
                85                  90                  95

Ser Ile Arg Asp Ala Gly His Lys Cys Pro Val Asp Asn Glu Ile Leu
            100                 105                 110

Leu Glu Asn Gln Leu Phe Pro Asp Asn Phe Ala Lys Arg Glu Ile Leu
        115                 120                 125

Ser Leu Met Val Lys Cys Pro Asn Glu Gly Cys Leu His Lys Met Glu
    130                 135                 140

Leu Arg His Leu Glu Asp His Gln Ala His Cys Glu Phe Ala Leu Met
145                 150                 155                 160

Asp Cys Pro Gln Cys Gln Arg Pro Phe Gln Lys Phe His Ile Asn Ile
                165                 170                 175

His Ile Leu Lys Asp Cys Pro Arg Arg Gln Val Ser Cys Asp Asn Cys
            180                 185                 190

Ala Ala Ser Met Ala Phe Glu Asp Lys Glu Ile His Asp Gln Asn Cys
        195                 200                 205

Pro Leu Ala Asn Val Ile Cys Glu Tyr Cys Asn Thr Ile Leu Ile Arg
    210                 215                 220

Glu Gln Met Pro Asn His Tyr Asp Leu Asp Cys Pro Thr Ala Pro Ile
225                 230                 235                 240

Pro Cys Thr Phe Ser Thr Phe Gly Cys His Glu Lys Met Gln Arg Asn
                245                 250                 255

His Leu Ala Arg His Leu Gln Glu Asn Thr Gln Ser His Met Arg Met
            260                 265                 270

Leu Ala Gln Ala Val His Ser Leu Ser Val Ile Pro Asp Ser Gly Tyr
        275                 280                 285

Ile Ser Glu Val Arg Asn Phe Gln Glu Thr Ile His Gln Leu Glu Gly
    290                 295                 300

Arg Leu Val Arg Gln Asp His Gln Ile Arg Glu Leu Thr Ala Lys Met
305                 310                 315                 320

Glu Thr Gln Ser Met Tyr Val Ser Glu Leu Lys Arg Thr Ile Arg Thr
                325                 330                 335

Leu Glu Asp Lys Val Ala Glu Ile Glu Ala Gln Gln Cys Asn Gly Ile
            340                 345                 350

Tyr Ile Trp Lys Ile Gly Asn Phe Gly Met His Leu Lys Cys Gln Glu
        355                 360                 365

Glu Glu Lys Pro Val Val Ile His Ser Pro Gly Phe Tyr Thr Gly Lys
    370                 375                 380

Pro Gly Tyr Lys Leu Cys Met Arg Leu His Leu Gln Leu Pro Thr Ala
385                 390                 395                 400

Gln Arg Cys Ala Asn Tyr Ile Ser Leu Phe Val His Thr Met Gln Gly
                405                 410                 415

Glu Tyr Asp Ser His Leu Pro Trp Pro Phe Gln Gly Thr Ile Arg Leu
            420                 425                 430

Thr Ile Leu Asp Gln Ser Glu Ala Pro Val Arg Gln Asn His Glu Glu
        435                 440                 445

Ile Met Asp Ala Lys Pro Glu Leu Leu Ala Phe Gln Arg Pro Thr Ile
    450                 455                 460

Pro Arg Asn Pro Lys Gly Phe Gly Tyr Val Thr Phe Met His Leu Glu
465                 470                 475                 480

Ala Leu Arg Gln Arg Thr Phe Ile Lys Asp Asp Thr Leu Leu Val Arg
                485                 490                 495
```

```
Cys Glu Val Ser Thr Arg Phe Asp Met Gly Ser Leu Arg Arg Glu Gly
                500                 505                 510

Phe Gln Pro Arg Ser Thr Asp Ala Gly Val
            515                 520

<210> SEQ ID NO 63
<211> LENGTH: 540
<212> TYPE: DNA
<213> ORGANISM: Homo sapiens
<220> FEATURE:
<221> NAME/KEY: misc_feature
<223> OTHER INFORMATION: GenBank Accession No.: NM_002954.2

<400> SEQUENCE: 63
cttttcgatc cgccatctgc ggtggagccg caaccaaaat gcagattttc gtgaaaaccc     60
ttacggggaa gaccatcacc ctcgaggttg aaccctcgga tacgatagaa aatgtaaagg    120
ccaagatcca ggataaggaa ggaattcctc ctgatcagca gagactgatc tttgctggca    180
agcagctaga agatggacgt actttgtctg actacaatat tcaaaaggag tctactcttc    240
atcttgtgtt gagacttcgt ggtggtgcta agaaaaggaa gaagaagtct tacaccactc    300
ccaagaagaa taagcacaag agaaagaagg ttaagctggc tgtcctgaaa tattataagg    360
tggatgagaa tggcaaaatt agtcgccttc gtcgagagtg cccttctgat gaatgtggtg    420
ctggggtgtt tatggcaagt cactttgaca gacattattg tggcaaatgt tgtctgactt    480
actgtttcaa caaaccagaa gacaagtaac tgtatgagtt aataaaagac atgaactaac    540

<210> SEQ ID NO 64
<211> LENGTH: 156
<212> TYPE: PRT
<213> ORGANISM: Homo sapiens
<220> FEATURE:
<221> NAME/KEY: MISC_FEATURE
<223> OTHER INFORMATION: GenBank Accession No.: NP_002945

<400> SEQUENCE: 64

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Ala Lys Lys Arg
65                  70                  75                  80

Lys Lys Lys Ser Tyr Thr Thr Pro Lys Lys Asn Lys His Lys Arg Lys
                85                  90                  95

Lys Val Lys Leu Ala Val Leu Lys Tyr Tyr Lys Val Asp Glu Asn Gly
            100                 105                 110

Lys Ile Ser Arg Leu Arg Arg Glu Cys Pro Ser Asp Glu Cys Gly Ala
        115                 120                 125

Gly Val Phe Met Ala Ser His Phe Asp Arg His Tyr Cys Gly Lys Cys
    130                 135                 140

Cys Leu Thr Tyr Cys Phe Asn Lys Pro Glu Asp Lys
145                 150                 155

<210> SEQ ID NO 65
<211> LENGTH: 605
```

```
<212> TYPE: DNA
<213> ORGANISM: Homo sapiens
<220> FEATURE:
<221> NAME/KEY: misc_feature
<223> OTHER INFORMATION: GenBank Accession No.: NM_006156.1

<400> SEQUENCE: 65
gaagtggccc ttgcaggcaa gagtgctgga gggcggcagc ggcgaccgga gcggtaggag      60
cagcaattta tccgtgtgca gccccaaact ggaaagaaga tgctaattaa agtgaagacg     120
ctgaccggaa aggagattga gattgacatt gaacctacag acaaggtgga gcgaatcaag     180
gagcgtgtgg aggagaaaga gggaatcccc ccacaacagc agaggctcat ctacagtggc     240
aagcagatga atgatgagaa gacagcagct gattacaaga ttttaggtgg ttcagtcctt     300
cacctggtgt tggctctgag aggaggaggt ggtcttaggc agtgatggac cctccatttt     360
acctctttac cctgtcgctc ataatgaggc atcatatatc ctctcactct ctgggacacc     420
atagccactg cccctcccc  tggatgccca gtaatgtatg tctactggtg ggagactgtg     480
aggatcccag gattcagtat tcctggccca gagggccttg ctggctactg ggtgttagtt     540
tgcagtcctg tgtgcttccc tctcttatga ctgtgtccct ggttgtcaat aaaatatttc     600
ctggc                                                                605

<210> SEQ ID NO 66
<211> LENGTH: 81
<212> TYPE: PRT
<213> ORGANISM: Homo sapiens
<220> FEATURE:
<221> NAME/KEY: MISC_FEATURE
<223> OTHER INFORMATION: GenBank Accession No.: NP_006147

<400> SEQUENCE: 66

Met Leu Ile Lys Val Lys Thr Leu Thr Gly Lys Glu Ile Glu Ile Asp
1               5                   10                  15

Ile Glu Pro Thr Asp Lys Val Glu Arg Ile Lys Glu Arg Val Glu Glu
            20                  25                  30

Lys Glu Gly Ile Pro Pro Gln Gln Gln Arg Leu Ile Tyr Ser Gly Lys
        35                  40                  45

Gln Met Asn Asp Glu Lys Thr Ala Ala Asp Tyr Lys Ile Leu Gly Gly
    50                  55                  60

Ser Val Leu His Leu Val Leu Ala Leu Arg Gly Gly Gly Leu Arg
65                  70                  75                  80

Gln

<210> SEQ ID NO 67
<211> LENGTH: 634
<212> TYPE: DNA
<213> ORGANISM: Homo sapiens
<220> FEATURE:
<221> NAME/KEY: misc_feature
<223> OTHER INFORMATION: GenBank Accession No.: NM_005101.1

<400> SEQUENCE: 67
cggctgagag gcagcgaact catctttgcc agtacaggag cttgtgccgt ggcccacagc      60
ccacagccca cagccatggg ctgggacctg acggtgaaga tgctggcggg caacgaattc    120
caggtgtccc tgagcagctc catgtcggtg tcagagctga aggcgcagat cacccagaag    180
attggcgtgc acgccttcca gcagcgtctg gctgtccacc cgagcggtgt ggcgctgcag    240
gacagggtcc cccttgccag ccagggcctg ggccctggca gcacggtcct gctggtggtg    300
```

```
gacaaatgcg acgaacctct gagcatcctg gtgaggaata acaagggccg cagcagcacc      360
tacgaggtcc ggctgacgca gaccgtggcc cacctgaagc agcaagtgag cgggctggag      420
ggtgtgcagg acgacctgtt ctggctgacc ttcgagggga agcccctgga ggaccagctc      480
ccgctggggg agtacggcct caagcccctg agcaccgtgt tcatgaatct gcgcctgcgg      540
ggaggcggca cagagcctgg cgggcggagc taagggcctc caccagcatc cgagcaggat      600
caagggccgg aaataaaggc tgttgtaaga gaat                                  634
```

<210> SEQ ID NO 68
<211> LENGTH: 165
<212> TYPE: PRT
<213> ORGANISM: Homo sapiens
<220> FEATURE:
<221> NAME/KEY: MISC_FEATURE
<223> OTHER INFORMATION: GenBank Accession No.: NP_005092.1

<400> SEQUENCE: 68

```
Met Gly Trp Asp Leu Thr Val Lys Met Leu Ala Gly Asn Glu Phe Gln
1               5                   10                  15

Val Ser Leu Ser Ser Ser Met Ser Val Ser Glu Leu Lys Ala Gln Ile
            20                  25                  30

Thr Gln Lys Ile Gly Val His Ala Phe Gln Gln Arg Leu Ala Val His
        35                  40                  45

Pro Ser Gly Val Ala Leu Gln Asp Arg Val Pro Leu Ala Ser Gln Gly
    50                  55                  60

Leu Gly Pro Gly Ser Thr Val Leu Leu Val Val Asp Lys Cys Asp Glu
65                  70                  75                  80

Pro Leu Ser Ile Leu Val Arg Asn Asn Lys Gly Arg Ser Ser Thr Tyr
                85                  90                  95

Glu Val Arg Leu Thr Gln Thr Val Ala His Leu Lys Gln Gln Val Ser
            100                 105                 110

Gly Leu Glu Gly Val Gln Asp Asp Leu Phe Trp Leu Thr Phe Glu Gly
        115                 120                 125

Lys Pro Leu Glu Asp Gln Leu Pro Leu Gly Glu Tyr Gly Leu Lys Pro
    130                 135                 140

Leu Ser Thr Val Phe Met Asn Leu Arg Leu Arg Gly Gly Thr Glu
145                 150                 155                 160

Pro Gly Gly Arg Ser
                165
```

<210> SEQ ID NO 69
<211> LENGTH: 473
<212> TYPE: DNA
<213> ORGANISM: Homo sapiens
<220> FEATURE:
<221> NAME/KEY: misc_feature
<223> OTHER INFORMATION: GenBank Accession No.: NM_004707.1

<400> SEQUENCE: 69

```
tcgagtgtct ccaagcaaga tggcggagga gccgcagtct gtgttgcagc ttcctacttc       60
aattgctgct ggaggggaag gacttacgga tgtctcccca gaaacaacca ccccggagcc      120
cccgtcttcc gctgcagttt ccccgggaac agaggaacct gctggcgaca ccaagaaaaa      180
aattgacatt ttgctaaagg ctgtgggaga cactccatat atgaaaacaa agaagtgggc      240
agtagagcga acacgaacca tccaaggact cattgacttc atcaaaaagt ttcttaaact      300
tgtggcctca gaacagttgt ttatttatgt gaatcagtcc tttgctccct ccccagacca      360
```

```
agaagttgga actctctatg agtgttttgg cagtgatggt aaactggttt tacattactg      420
caagtctcag gcgtggggat gaaccacaaa gaaaatcaac ttgctactac atg            473

<210> SEQ ID NO 70
<211> LENGTH: 140
<212> TYPE: PRT
<213> ORGANISM: Homo sapiens
<220> FEATURE:
<221> NAME/KEY: MISC_FEATURE
<223> OTHER INFORMATION: GenBank Accession No.: NP_004698.1

<400> SEQUENCE: 70

Met Ala Glu Glu Pro Gln Ser Val Leu Gln Leu Pro Thr Ser Ile Ala
1               5                   10                  15

Ala Gly Gly Glu Gly Leu Thr Asp Val Ser Pro Glu Thr Thr Thr Pro
            20                  25                  30

Glu Pro Pro Ser Ser Ala Ala Val Ser Pro Gly Thr Glu Glu Pro Ala
        35                  40                  45

Gly Asp Thr Lys Lys Lys Ile Asp Ile Leu Leu Lys Ala Val Gly Asp
    50                  55                  60

Thr Pro Ile Met Lys Thr Lys Lys Trp Ala Val Glu Arg Thr Arg Thr
65                  70                  75                  80

Ile Gln Gly Leu Ile Asp Phe Ile Lys Lys Phe Leu Lys Leu Val Ala
                85                  90                  95

Ser Glu Gln Leu Phe Ile Tyr Val Asn Gln Ser Phe Ala Pro Ser Pro
            100                 105                 110

Asp Gln Glu Val Gly Thr Leu Tyr Glu Cys Phe Gly Ser Asp Gly Lys
        115                 120                 125

Leu Val Leu His Tyr Cys Lys Ser Gln Ala Trp Gly
    130                 135                 140

<210> SEQ ID NO 71
<211> LENGTH: 2155
<212> TYPE: DNA
<213> ORGANISM: Homo sapiens
<220> FEATURE:
<221> NAME/KEY: misc_feature
<223> OTHER INFORMATION: GenBank Accession No.: NM_022818.2

<400> SEQUENCE: 71
attcgccgcc gcagcagccg ccgccccgg gagccgccgg gaccctcgcg tcgtcgccgc       60
cgccgccgcc cagatccccg caccatgccg tcggagaaga ccttcaagca gcgccgcacc      120
ttcgaacaaa gagtagaaga tgtccgactt attcgagagc agcatccaac caaaatcccg     180
gtgataatag aacgatacaa gggtgagaag cagcttcctg ttctggataa acaaagttc      240 cttgtacctg accatgtcaa catgagtgag ctcatcaaga taattagaag gcgcttacag      300
ctcaatgcta atcaggcctt cttcctgttg gtgaacggac acagcatggt cagcgtctcc      360
acaccaatct cagaggtgta tgagagtgag aaagatgaag atggattcct gtacatggtc      420
tatgcctccc aggagacgtt cgggatgaaa ttgtcagtgt aaaaccagaa aaaatgcatc      480
tcttctagaa ttgtttaaac ccttaccaag gaaaaaaaag gggtgttacc aactgagatc      540
gatcagttca tccaatcaca gatcatgaaa cagtagtgtt cccacctagg agtgttagga      600
agttgtgttt gtgtttcaag cagaaaaact gagctccaag tgagcacatt cagctttgga      660
aactatatta tttaatgtag gctagcttgt tttcaaattt taaagtttta aaataaaat      720 actttgcatt ctaagttgcc aataaaatag accttcaagt tattttaatg ctctttctc      780
```

```
actaatagga acttgtaatt ccagcagtaa tttaaaggct ttcagagaga ccctgagtct    840
tctcttcagg ttcacagaac ccgccgcctt tttgggtaga agttttctac tcagctagag    900
agatctccct aagaggatct ttaggcctga gttgtgaagc gcaaccccg caaaacgcat     960 ttgccatcac agttggcaca aacgcagggt aaacgggctg tgtgagaaaa cggccctgac   1020
tgtaaactgc tgaaggtccc tgactcctaa gagaaccaca cccaaagtcc tcactcttgc   1080
aggggtagac atttctggtt tggtttgttc tctagatagt tacacacata agacaccac    1140 tcaaaggaa acttgaataa tttataattt tgatcgagtt tcttaaaaga ccctggagaa    1200
agagtggcat ttcttctgtt tcaggttttg tctgagttca aactagtgcc tgtgttgtta   1260
cggaaagcag cagtgtacca gtgtcactct ggagtacagc gggagaaaca caaatagta    1320 taactgaaaa cattaacatt cagacacact cccttctgcc ttccggctta agctgtgga    1380 tgatccacgt ttttgttttt taatgttaa atgtgtaact cagtattact gaaaaggtac    1440
ccacattttg aatagtagtt atcactctta ggtcagacag ccatcagaat tctcccacac   1500
caagtgcatg tcagttgtgg agaaaacata gcaaaagag ccgtacgctc tttacagata    1560
ctaatgtcaa gagttaaacc tcctcaggtt caacctgtga taaaagacta gtgcttccca   1620
gtacttgcat ggggttcact atttatagtt ttcttgggag tatcacagga aaatcacaat   1680
tacaccactt tagaccctat gtgtagcagg tcacaactta cccttgtgtg tttagatgtg   1740
tatgaaatac ctgtatacgt tagtgaaagc tgtttactgt aacggggaaa accagattct   1800
ttgcatctgg gccctctact gattgttaaa ggagttcctg tcacctgctc cccccacccc   1860
cgcatgcgtc tgtccacttg gctaactttt aatatgtgta tttttacatt atgtatattc   1920
ttaactggac tgtctcgttt agactgtata catcatatct gacattattg taactaccgt   1980
gtgatcagta agattcctgt aagaaatact gcttttaag aaaaaaaata acatgctgag    2040
gggtgaccta tatcccatgt gagtggtcac tttatttata ggatctttaa aacattttta   2100
atgaactaag ttgaataaag gcacaattaa aaactgtcaa aaaaaaaaa aaaaa         2155
```

<210> SEQ ID NO 72
<211> LENGTH: 125
<212> TYPE: PRT
<213> ORGANISM: Homo sapiens
<220> FEATURE:
<221> NAME/KEY: MISC_FEATURE
<223> OTHER INFORMATION: GenBank Accession No.: NP_073729.1

<400> SEQUENCE: 72

```
Met Pro Ser Glu Lys Thr Phe Lys Gln Arg Arg Thr Phe Glu Gln Arg
1               5                   10                  15

Val Glu Asp Val Arg Leu Ile Arg Glu Gln His Pro Thr Lys Ile Pro
            20                  25                  30

Val Ile Ile Glu Arg Tyr Lys Gly Glu Lys Gln Leu Pro Val Leu Asp
        35                  40                  45

Lys Thr Lys Phe Leu Val Pro Asp His Val Asn Met Ser Glu Leu Ile
    50                  55                  60

Lys Ile Ile Arg Arg Arg Leu Gln Leu Asn Ala Asn Gln Ala Phe Phe
65                  70                  75                  80

Leu Leu Val Asn Gly His Ser Met Val Ser Val Ser Thr Pro Ile Ser
                85                  90                  95

Glu Val Tyr Glu Ser Glu Lys Asp Glu Asp Gly Phe Leu Tyr Met Val
            100                 105                 110

Tyr Ala Ser Gln Glu Thr Phe Gly Met Lys Leu Ser Val
        115                 120                 125
```

<210> SEQ ID NO 73
<211> LENGTH: 777
<212> TYPE: DNA
<213> ORGANISM: Homo sapiens
<220> FEATURE:
<221> NAME/KEY: misc_feature
<223> OTHER INFORMATION: GenBank Accession No.: NM_006398.1

<400> SEQUENCE: 73

```
ggcccttgt ctgcagagat ggctcccaat gcttcctgcc tctgtgtgca tgtccgttcc      60
gaggaatggg atttaatgac ctttgatgcc aacccatatg acagcgtgaa aaaaatcaaa    120
gaacatgtcc ggtctaagac caaggttcct gtgcaggacc aggttctttt gctgggctcc    180
aagatcttaa agccacggag aagcctctca tcttatggca ttgacaaaga gaagaccatc    240
caccttaccc tgaaagtggt gaagcccagt gatgaggagc tgcccttgtt tcttgtggag    300
tcaggtgatg aggcaaagag gcacctcctc caggtgcgaa ggtccagctc agtggcacaa    360
gtgaaagcaa tgatcgagac taagacgggg ataatccctg agacccagat tgtgacttgc    420
aatggaaaga gactggaaga tgggaagatg atggcagatt acggcatcag aaagggcaac    480
ttactcttcc tggcatctta ttgtattgga gggtgaccac cctggggatg gggtgttggc    540
aggggtcaaa aagcttattt cttttaatct cttactcaac gaacacatct tctgatgatt    600
tcccaaaatt aatgagaatg agatgagtag agtaagattt gggtgggatg gtaggatga    660
agtatattgc ccaactctat gtttctttga ttctaacaca attaattaag tgacatgatt    720
tttactaatg tattactgag actagtaaat aaatttttaa ggcaaaatag agcattc      777
```

<210> SEQ ID NO 74
<211> LENGTH: 165
<212> TYPE: PRT
<213> ORGANISM: Homo sapiens
<220> FEATURE:
<221> NAME/KEY: MISC_FEATURE
<223> OTHER INFORMATION: GenBank Accession No.: NP_006389.1

<400> SEQUENCE: 74

Met Ala Pro Asn Ala Ser Cys Leu Cys Val His Val Arg Ser Glu Glu
1               5                   10                  15

Trp Asp Leu Met Thr Phe Asp Ala Asn Pro Tyr Asp Ser Val Lys Lys
            20                  25                  30

Ile Lys Glu His Val Arg Ser Lys Thr Lys Val Pro Val Gln Asp Gln
        35                  40                  45

Val Leu Leu Leu Gly Ser Lys Ile Leu Lys Pro Arg Arg Ser Leu Ser
    50                  55                  60

Ser Tyr Gly Ile Asp Lys Glu Lys Thr Ile His Leu Thr Leu Lys Val
65                  70                  75                  80

Val Lys Pro Ser Asp Glu Glu Leu Pro Leu Phe Leu Val Glu Ser Gly
                85                  90                  95

Asp Glu Ala Lys Arg His Leu Leu Gln Val Arg Arg Ser Ser Ser Val
            100                 105                 110

Ala Gln Val Lys Ala Met Ile Glu Thr Lys Thr Gly Ile Ile Pro Glu
        115                 120                 125

Thr Gln Ile Val Thr Cys Asn Gly Lys Arg Leu Glu Asp Gly Lys Met
    130                 135                 140

Met Ala Asp Tyr Gly Ile Arg Lys Gly Asn Leu Leu Phe Leu Ala Ser
145                 150                 155                 160

Tyr Cys Ile Gly Gly
            165

<210> SEQ ID NO 75
<211> LENGTH: 574
<212> TYPE: DNA
<213> ORGANISM: Homo sapiens
<220> FEATURE:
<221> NAME/KEY: misc_feature
<223> OTHER INFORMATION: GenBank Accession No.: NM_001997.2

<400> SEQUENCE: 75
cagtgacgtg acacgcagcc cacggtctgt actgacgcgc cctcgcttct tcctctttct     60
cgactccatc ttcgcggtag ctgggaccgc cgttcagtcg ccaatatgca gctctttgtc    120
cgcgcccagg agctacacac cttcgaggtg accggccagg aaacggtcgc ccagatcaag    180
gctcatgtag cctcactgga gggcattgcc ccggaagatc aagtcgtgct cctggcaggc    240
gcgcccctgg aggatgaggc cactctgggc cagtgcgggg tggaggccct gactaccctg    300
gaagtagcag gccgcatgct tggaggtaaa gtccatggtt ccctggcccg tgctggaaaa    360
gtgagaggtc agactcctaa ggtggccaaa caggagaaga agaagaagaa gacaggtcgg    420
gctaagcggc ggatgcagta caaccggcgc tttgtcaacg ttgtgcccac ctttggcaag    480
aagaagggcc ccaatgccaa ctcttaagtc ttttgtaatt ctggctttct ctaataaaaa    540
agccacttag ttcagtcaaa aaaaaaaaaa aaaa                                574

<210> SEQ ID NO 76
<211> LENGTH: 133
<212> TYPE: PRT
<213> ORGANISM: Homo sapiens
<220> FEATURE:
<221> NAME/KEY: MISC_FEATURE
<223> OTHER INFORMATION: GenBank Accession No.: NP_001988.1

<400> SEQUENCE: 76

Met Gln Leu Phe Val Arg Ala Gln Glu Leu His Thr Phe Glu Val Thr
1               5                   10                  15

Gly Gln Glu Thr Val Ala Gln Ile Lys Ala His Val Ala Ser Leu Glu
            20                  25                  30

Gly Ile Ala Pro Glu Asp Gln Val Val Leu Leu Ala Gly Ala Pro Leu
        35                  40                  45

Glu Asp Glu Ala Thr Leu Gly Gln Cys Gly Val Glu Ala Leu Thr Thr
    50                  55                  60

Leu Glu Val Ala Gly Arg Met Leu Gly Gly Lys Val His Gly Ser Leu
65                  70                  75                  80

Ala Arg Ala Gly Lys Val Arg Gly Gln Thr Pro Lys Val Ala Lys Gln
                85                  90                  95

Glu Lys Lys Lys Lys Lys Thr Gly Arg Ala Lys Arg Arg Met Gln Tyr
            100                 105                 110

Asn Arg Arg Phe Val Asn Val Val Pro Thr Phe Gly Lys Lys Lys Gly
        115                 120                 125

Pro Asn Ala Asn Ser
    130

<210> SEQ ID NO 77
<211> LENGTH: 1227
<212> TYPE: DNA
<213> ORGANISM: Homo sapiens
<220> FEATURE:

<221> NAME/KEY: misc_feature
<223> OTHER INFORMATION: GenBank Accession No.: NM_003352.2

<400> SEQUENCE: 77

```
cgtagcggaa gttactgcag ccgcggtgtt gtgctgtggg aagggagaa ggatttgtaa      60
accccggagc gaggttctgc ttacccgagg ccgctgctgt gcggagaccc ccgggtgaag    120
ccaccgtcat catgtctgac caggaggcaa aaccttcaac tgaggacttg ggggataaga    180
aggaaggtga atatattaaa ctcaaagtca ttggacagga tagcagtgag attcacttca    240
aagtgaaaat gacaacacat ctcaagaaac tcaaagaatc atactgtcaa agacagggtg    300
ttccaatgaa ttcactcagg tttctctttg agggtcagag aattgctgat aatcatactc    360
caaaagaact gggaatggag gaagaagatg tgattgaagt ttatcaggaa caaacggggg    420
gtcattcaac agtttagata ttctttttat tttttttct tttccctcaa tccttttta     480
tttttaaaaa tagttctttt gtaatgtggt gttcaaaacg gaattgaaaa ctggcacccc    540
atctctttga acatctggt aatttgaatt ctagtgctca ttattcatta ttgtttgttt    600
tcattgtgct gatttttggt gatcaagcct cagtcccctt catattaccc tctccttttt    660
aaaaattacg tgtgcacaga gaggtcacct ttttcaggac attgcatttt caggcttgtg    720
gtgataaata agatcgacca atgcaagtgt tcataatgac tttccaattg gccctgatgt    780
tctagcatgt gattacttca ctcctggact gtgactttca gtgggagatg gaagtttttc    840
agagaactga actgtggaaa aatgaccttt ccttaacttg aagctacttt taaaatttga    900
gggtctggac caaaagaaga ggaatatcag gttgaagtca gatgacaga taaggtgaga      960
gtaatgacta actccaaaga tggcttcact gaagaaaagg catttaaga tttttaaaa     1020
atcttgtcag aagatcccag aaaagttcta attttcatta gcaattaata aagctataca   1080
tgcagaaatg aatacaacag aacactgctc tttttgattt tatttgtact ttttggcctg   1140
ggatatgggt tttaaatgga cattgtctgt accagcttca ttaaaataaa caatatttgt   1200
aaaaatcaaa aaaaaaaaaa aaaaaaa                                      1227
```

<210> SEQ ID NO 78
<211> LENGTH: 101
<212> TYPE: PRT
<213> ORGANISM: Homo sapiens
<220> FEATURE:
<221> NAME/KEY: MISC_FEATURE
<223> OTHER INFORMATION: GenBank Accession No.: NP_003343.1

<400> SEQUENCE: 78

```
Met Ser Asp Gln Glu Ala Lys Pro Ser Thr Glu Asp Leu Gly Asp Lys
1               5                   10                  15

Lys Glu Gly Glu Tyr Ile Lys Leu Lys Val Ile Gly Gln Asp Ser Ser
            20                  25                  30

Glu Ile His Phe Lys Val Lys Met Thr Thr His Leu Lys Lys Leu Lys
        35                  40                  45

Glu Ser Tyr Cys Gln Arg Gln Gly Val Pro Met Asn Ser Leu Arg Phe
    50                  55                  60

Leu Phe Glu Gly Gln Arg Ile Ala Asp Asn His Thr Pro Lys Glu Leu
65                  70                  75                  80

Gly Met Glu Glu Glu Asp Val Ile Glu Val Tyr Gln Glu Gln Thr Gly
                85                  90                  95

Gly His Ser Thr Val
            100
```

<210> SEQ ID NO 79
<211> LENGTH: 1733
<212> TYPE: DNA
<213> ORGANISM: Homo sapiens
<220> FEATURE:
<221> NAME/KEY: misc_feature
<223> OTHER INFORMATION: GenBank Accession No.: NM_006936.1
<220> FEATURE:
<221> NAME/KEY: misc_feature
<222> LOCATION: (19)..(19)
<223> OTHER INFORMATION: n is a, c, g, or t

<400> SEQUENCE: 79

```
ttcggcacag gcgggaganc ggcggggccg aagcgtgaac tcgcccgctc cggcttgctt      60
cccccgcgcc gcctcccgc gccgctcgga agccatgtcc gaggagaagc ccaaggaggg     120
tgtgaagaca gagaatgacc acatcaacct gaaggtggcc gggcaggacg gctccgtggt    180
gcagttcaag atcaagaggc acacgtcgct gagcaagctg atgaaggcct actgcgagag    240
gcagggcttg tcaatgaggc agatcagatt caggttcgac gggcagccaa tcaatgaaac    300
tgacactcca gcacagctga gaatggagga cgaggacacc atcgacgtgt ccagcagca    360
gacgggaggt gtgccggaga gcagcctggc agggcacagt ttctagaggg cccgtcccca    420
gcccgggccg tccatcctcg cattgctgtt gaatggtgag cacgtgacca tgccgaccac    480
aaaggtgtct gcggaaactc gaggacattc accacgatga ttttcctctc tttgatgtac    540
ttcaagtgca actcaaaact atatctgcag ggatgaatct gtaacttaaa ttgggccaat    600
cagaattgtt atctttgttc aggtaaaatg agttgcaaga tattgtgggt acttttgtgt    660
gctcatttgt gttttccccc cctcctacaa cattttttta accccaaaat tatagcctga    720
atgttcgctt ttagtctggc cagggatctg actcctgagt tggttgcctc tcccctgctc    780
actccagtca catagagaat tggtgtttcc cgcagtgggg attgcagctg ttggacaggt    840
attggggca aggttggtag ggaggacaga ctgtcacttg ctgttacagg cacaggtgat    900
taaaatgcta aatattgcaa atttaagctt tgtcagtata tggaaaagtt gaagggaaaa    960
tactggaatg cttcttcaaa ggttaaaaaa taaccgagtc ttttggtaat ttgaccccac   1020
gtgctctctg gccctcaagc atgtaacctc ggggtctgag gcccaggacc caccccctg   1080
ccaccctcc caccccactc cctgctcagt acctggcgtt ggtacacagg caaggattgg   1140
cacaaccaaa attggccttt ttctccctct taatattgaa gaaattccca catttctcat   1200
ttggtaatgg tgttgtggcc tcagatttct tctagtattt gcttctgatg aatgattatg   1260
gtctatacat aaaaaagtaa gactaagtat tgctgaattt gcagttatgt tgtcgtgtat   1320
aagagctact tccaagtgtg gttacaaatg aacccatgga atgatgactt catgttcttc   1380
tcgtgggttt gtgccgtgct gctttccaaa taggtattga atttatgcat tagtctggtg   1440
atttcagttc tgtgaaatat tttgggatct ataccaatta aacattttca tagttctgcc   1500
tattgtcctt ccctgaggct ccattgctgc ttggtggcca ttctctgcct ttttacagtc   1560
acctgaacaa tgacccatca tctcttgctt gcttgaaatc ttgctgaaat gttctcattt   1620
cctgtttgct gtatgggctc gggtgggatg tttgttggct ctgttgtgtt tattcaccaa   1680
tttgtacatt atttgttgtc ctttactact gtaaacagta aatatagttt ggt          1733
```

<210> SEQ ID NO 80
<211> LENGTH: 103
<212> TYPE: PRT
<213> ORGANISM: Homo sapiens
<220> FEATURE:

```
<221> NAME/KEY: MISC_FEATURE
<223> OTHER INFORMATION: GenBank Accession No.: NP_008867.1

<400> SEQUENCE: 80

Met Ser Glu Glu Lys Pro Lys Glu Gly Val Lys Thr Glu Asn Asp His
1               5                   10                  15

Ile Asn Leu Lys Val Ala Gly Gln Asp Gly Ser Val Val Gln Phe Lys
            20                  25                  30

Ile Lys Arg His Thr Ser Leu Ser Lys Leu Met Lys Ala Tyr Cys Glu
        35                  40                  45

Arg Gln Gly Leu Ser Met Arg Gln Ile Arg Phe Arg Phe Asp Gly Gln
    50                  55                  60

Pro Ile Asn Glu Thr Asp Thr Pro Ala Gln Leu Arg Met Glu Asp Glu
65                  70                  75                  80

Asp Thr Ile Asp Val Phe Gln Gln Gln Thr Gly Gly Val Pro Glu Ser
                85                  90                  95

Ser Leu Ala Gly His Ser Phe
            100

<210> SEQ ID NO 81
<211> LENGTH: 1478
<212> TYPE: DNA
<213> ORGANISM: Homo sapiens
<220> FEATURE:
<221> NAME/KEY: misc_feature
<223> OTHER INFORMATION: GenBank Accession No.: NM_006937.2

<400> SEQUENCE: 81
gtgcgcgcac cctctcccct cgtccaccgc tgccgcctcc ttcttctgcc gctcctggtg      60
ctgcttgtgt gctcgtttgg tgcggacctg gtacctcttt tgtgaagcgg cagctgagga     120
gactccggcg ctcgccatgg ccgacgaaaa gcccaaggaa ggagtcaaga ctgagaacaa     180
caatcatatt aatttgaagg tggcggggca ggatggttct gtggtgcagt ttaagattaa     240
gaggcataca ccacttagta aactaatgaa agcctattgt gaacgacagg gattgtcaat     300
gaggcagatc agattccgat tgacgggca accaatcaat gaaacagaca cacctgcaca     360
gttggaaatg gaggatgaag atacaattga tgtgttccaa cagcagacgg gaggtgtcta     420
ctgaaaaggg aacctgcttc tttactccag aactctgttc tttaaagacc aagattacat     480
tctcaattag aaaactgcaa tttggttcca ccacatcctg actactaccg tatagttttc     540
tctattcttt catttccccc ttccccattc ctttattgta cataaagtaa ctggtatatg     600
tgcacaagca tattgcattt tttttttttt taactaaaca gccaatggta tgttttgatt     660
gacatcaagt gggagacggga tggggaaaaa tactgattct gtgaaaatac ccctttctc     720 cattagtggc atgctcattc agctcttatc tttatattcc agtaagttat tttgctctca     780 ctgtttaac aaaaaaaaaa aacaacaaca taaaaatcct tgcataccctt gttcaattgg     840 agaattttaa tgttttcat ttatcattgt aaaaccaagg acaattttat aactttttg       900 tacgtagctg ttacatgtag ggcaatctgt ctttaagtag ggataaatta ctctaaaaca     960
aaaaagaatc ctagatagtt ttcccttcaa gtcaagcgtc ttgttgttta aataaacttc    1020
ttgtttaaaa tgagctgttt tctttattct gagaaatatt aaatagaaaa ttgaggctta    1080
gaaaaaacat aaataggcct gcttagaagt aacatttcaa gaaggaaata aagctacttg    1140
gtgtttctga cagactgata ctgatgccaa acaaagaata acagtttat aaatatcacc     1200 ttgttccaaa agtttctcta ggtcccatgt taatatgcaa gtatactagc agaaaaattg    1260
```

-continued

```
ggccatagta tcgtggattt ccaggtattt tctgtatatt aagtgaggca cggagcatag   1320
ggtatagggt agcacatgtg gcaaggaaaa agttctgatt ttgcctttgt tgctgataaa   1380
acactgaacc attctagcct gcacttatca taagtaaata ctccctaacc taaaataaag   1440
ttttcgttcc aaaaaaaaaa aaaaaaaaaa aaaaaaa                            1478

<210> SEQ ID NO 82
<211> LENGTH: 95
<212> TYPE: PRT
<213> ORGANISM: Homo sapiens
<220> FEATURE:
<221> NAME/KEY: MISC_FEATURE
<223> OTHER INFORMATION: GenBank Accession No.: NP_008868.2

<400> SEQUENCE: 82

Met Ala Asp Glu Lys Pro Lys Glu Gly Val Lys Thr Glu Asn Asn Asn
1               5                   10                  15

His Ile Asn Leu Lys Val Ala Gly Gln Asp Gly Ser Val Val Gln Phe
            20                  25                  30

Lys Ile Lys Arg His Thr Pro Leu Ser Lys Leu Met Lys Ala Tyr Cys
        35                  40                  45

Glu Arg Gln Gly Leu Ser Met Arg Gln Ile Arg Phe Arg Phe Asp Gly
    50                  55                  60

Gln Pro Ile Asn Glu Thr Asp Thr Pro Ala Gln Leu Glu Met Glu Asp
65                  70                  75                  80

Glu Asp Thr Ile Asp Val Phe Gln Gln Gln Thr Gly Gly Val Tyr
                85                  90                  95
```